(12) United States Patent
Puch-Solis

(10) Patent No.: US 8,121,795 B2
(45) Date of Patent: Feb. 21, 2012

(54) COMPUTING LIKELIHOOD RATIOS USING PEAK HEIGHTS

(75) Inventor: Roberto Puch-Solis, Solihull (GB)

(73) Assignee: Forensic Science Service Ltd., Birmingham (GB)

(*) Notice: Subject to any disclaimer, the term of this patent is extended or adjusted under 35 U.S.C. 154(b) by 381 days.

(21) Appl. No.: 12/273,951

(22) Filed: Nov. 19, 2008

(65) Prior Publication Data

US 2009/0132173 A1 May 21, 2009

(30) Foreign Application Priority Data

Nov. 19, 2007 (GB) .................................. 0722649.1
Mar. 13, 2008 (GB) .................................. 0804665.8
Jun. 11, 2008 (GB) .................................. 0810624.7
Aug. 21, 2008 (GB) .................................. 0815300.9

(51) Int. Cl.
*G01N 33/50* (2006.01)
(52) U.S. Cl. .......................................... 702/19; 702/20
(58) Field of Classification Search .................... 702/19, 702/20; 435/6
See application file for complete search history.

(56) References Cited

U.S. PATENT DOCUMENTS

2002/0007248 A1* 1/2002 Gill et al. ..................... 702/20

OTHER PUBLICATIONS

Balding et al., "Population genetics of STR loci in Caucasians," *Int. J. Legal. Med.* (1996) 108: 300-305.

Dempster et al., "Maximum likelihood from incomplete data via the EM algorithm," *Journal of the Royal Statistical Society* (1977) 39 (1): 1-38.
Casella, "Bivariate Transformation," (1990): 148-149.
Balding et al., "Population genetics of STR loci in Caucasians," *Int. J. Legal Med.* (1996) 108: 300-305.
McLachlan et al., *Finite Mixture Models*. New York: John Wiley & Sons, Inc., 2000.
Balding, D.J., *Weight-of-evidence for Forensic DNA Profiles*. West Sussex.: John Wiley & Sons Ltd., 2005.
Gill et al., "An Investigation of the rigor of interpretation rules for STRs derived from less than 100 pg of DNA," *Forensic Science International* (2000) 1112: 17-40.
Gill et al., "*LoComatioN*: A software tool for the analysis of low copy number DNA profiles," *Forensic Science International* (2007) 166: 128-138.
Buckleton et al., "An extended likelihood ratio framework for interpreting evidence," *Science & Justice* (2006) 46 (2) : 69-78.
Gill, P., "Letter to the Editor: National recommendations of the Technical UK DNA working group on mixture interpretation for the NDNAD and for court going purposes," *Forensic Science International: Genetics 2* (2008) 2: 76-82.
Dixon et al., "Validation of a 21-locus autosomal SNP multiplex for forensic identification purposes," *Forensic Science International* (2005) 154: 62-77.
International Search Report for corresponding PCT Application PCT/GB2008/003882 mailed Mar. 30, 2009.

(Continued)

*Primary Examiner* — John H Le
(74) *Attorney, Agent, or Firm* — Merchant & Gould P.C.

(57) ABSTRACT

Methods for comparing a first DNA profile with a second DNA profile are provided. The likelihood ratio for one hypothesis relative to another, as to the sources of the DNA, is conditioned on quantity of DNA in the test sample providing the first DNA profile and/or another sample providing the second DNA profile.

32 Claims, 12 Drawing Sheets

Estimation of a one dimensional pdf for peak heights in the interval $(30, \infty)$

OTHER PUBLICATIONS

Form PCT/ISA/237 for corresponding PCT Application PCT/GB2008/003882.

Form PCT/ISA/220 for corresponding PCT Application PCT/GB2008/003882.

Evett et al., "A guide to interpreting single locus profiles of DNA mixtures in forensic cases," *JFSS* (1991) 31 (1): 41-47.

Balding et al., "DNA profile match probability calculation: how to allow for population stratification, relatedness, database selection and single bands," *Forensic Science International* (1994) 64: 125-140.

Gill et al., "An investigation of the rigor of interpretation rules for STRs derived from less than 100 pg of DNA," *Forensic Science International* (2000) 112: 17-40.

Buckleton et al, "Forensic DNA evidence interpretation," Chapter 7: *CRC Press* (2005): 217-274.

Gill et al., "LoComatioN: A software tool for the analysis of low copy number DNA profiles," *Forensic Science International* (2007) 166: 128-138.

Evett et al., "Interpreting DNA evidence: Statistical Genetics for Forensic Scientists" Chapters 7 & 8: *Sinauer Associates*, Sunderland, MA. 188-216, Aug, 12, 1998.

* cited by examiner

A graphical representation of the sample space of peak heights

Estimation of a one dimensional pdf for peak heights in the interval $(30, \infty)$ Overall pdf for peak height of a homozygote donor An extrapolation of a one-dimensional pdf to two dimensions Extrapolated two-dimensional pdf. The x and y - axis display homozygote peak height A scatter plot of mean height and heterozygote balance in natural-logarithm scale Estimated and lognormal pdf's for mean height 50rfu Estimated and lognormal pdf's for mean height 100rfu Estimated & lognormal pdf's of heterozygote balance given mean height Estimated and lognormal pdf's for mean height 500rfu Estimated & lognormal pdf's of heterozygote balance given mean height Estimated and lognormal pdf's for mean height 1,000rfu Lognormal parameters computed from estimated pdf for heterozygote balance given mean height whilst setting $\mu = 0.1069$ Corrected $\sigma$ through an estimated linear trend Probability distribution for $H_1$ in region (1,0). The estimated parameter $\lambda_{(1,0)} = 26.24$. The estimation was done by subtraction 29 to the height values.

The state space of (M,N) is the area within the rectangle

Probability distribution for $H_1$ in region (1,0). The estimated parameter $\lambda_{(0,2)} = 25.30$. The estimation was done by subtraction 30 to the height values.

Probability of dropout as a function of peak height of the remaining allele

LR for locus D2 where the suspect is heterozygous and there is only one peak in the crime stain

COMPUTING LIKELIHOOD RATIOS USING PEAK HEIGHTS

This application is claims the benefit of Serial No. GB 0722649.1, filed Nov. 19, 2007 in Great Britain, and also of Serial No. GB 0804665.8, filed Mar. 13, 2008 in Great Britain, and also of Serial No. GB 0810624.7, filed Jun. 11, 2008, and also of Serial No. GB 0815300.9, filed Aug. 21, 2008 and which application(s) are incorporated herein by reference. A claim of priority to all, to the extent appropriate is made.

BACKGROUND OF THE INVENTION

This invention concerns improvements in and relating to the consideration of evidence, particularly, but not exclusively the consideration of DNA evidence.

In many situations, particularly in forensic science, there is a need to consider one piece of evidence against one or more other pieces of evidence.

For instance, it may be desirable to compare a sample collected from a crime scene with a sample collected from a person, with a view to linking the two by comparing the characteristics of their DNA. This is an evidential consideration. The result may be used directly in criminal or civil legal proceedings. Such situations include instances where the sample from the crime scene is contributed to by more than one person.

In other instances, it may be desirable to establish the most likely matches between examples of characteristics of DNA samples stored on a database with a further sample. The most likely matches or links suggested may guide further investigations. This is an intelligence consideration.

In both of these instances, it is desirable to be able to express the strength or likelihood of the comparison made, a so called likelihood ratio.

SUMMARY OF THE INVENTION

The present invention has amongst its possible aims to establish likelihood ratios. The present invention has amongst its possible aims to provide a more accurate or robust method for establishing likelihood ratios. The present invention has amongst its possible aims to provide probability distribution functions for use in establishing likelihood ratios, where the probability distribution functions are derived from experimental data.

According to a first aspect of the invention we provide a method of comparing a test sample result set with another sample result set, the method including:
  providing information for the first result set on the one or more identities detected for a variable characteristic of DNA;
  providing information for the second result set on the one or more identities detected for a variable characteristic of DNA.

The method of comparing may be used to considered evidence, for instance in civil or criminal legal proceedings. The comparison may be as to the relative likelihoods, for instance a likelihood ratio, of one hypothesis to another hypothesis. The comparison may be as to the relative likelihoods of the evidence relating to one hypothesis to another hypothesis. In particular, this may be a hypothesis advanced by the prosecution in the legal proceedings and another hypothesis advanced by the defence in the legal proceedings. The likelihood ratio may be of the form:

$$LR = \frac{Pr(C|S, H_p)}{Pr(C|S, H_d)}$$

where
  C is the first or test result set from a test sample, more particularly, the first result set taken from a sample recovered from a person or location linked with a crime, potentially expressed in terms of peak positions and/or heights;
  S is the second or another result set, more particularly, the second result set taken from a sample collected from a person, particularly expressed as a suspect's genotype;
  $H_p$ is one hypothesis, more particularly the prosecution hypothesis in legal proceedings stating "The suspect left the sample at the scene of crime";
  $H_d$ is an alternative hypothesis, more particularly the defence hypothesis in legal proceedings stating "Someone else left the sample at the crime scene".

The likelihood ratio may be defined as:

$$LR = \frac{Pr(C|S, H_p)}{\sum_i Pr(C|U_i, S, H_d) Pr(U_i|S, H_d)}$$

where $U_i$ is one of the supposed sources stated in $H_d$.

The likelihood ratio may be defined as:

$$LR = \frac{f(C|S, H_p)}{\sum_i f(C|U_i, S, H_d) Pr(U_i|S, H_d)}$$

where the f terms are factors that are likelihoods.

The factor $Pr(U_i|S,H_d)$ may be computed by using various methods, including those which may include consideration of relatedness between the suspect and the unknown contributor and/or those described in D. J. Balding (2005), "Weight-of-evidence for forensic DNA profiles", John Wiley & Sons Ltd and/or J. Buckleton, C. M. Triggs, S. J. Walsh (2005), "Forensic DNA evidence interpretation", CRC Press.

The factors $f(C|S,H_p)$ and/or $f(C|U_i,S,H_d)$ may be taken as statements of the same type of calculation. Those factors may be taken as definitions of the likelihood of observing the set of peak heights in C given a supposed donor.

The comparison may include the consideration of the term:

$$f(C|G)$$

where G denotes the supposed donor genotype. The comparison may include the consideration of this term as, or as a component of, the denominator of the likelihood ratio, and/or the consideration of this term as, or as a component of, the nominator of the likelihood ratio.

The term $f(C|G)$ may be an estimation. The term $f(C|G)$ may be derived from experimental data. The term $f(C|G)$ may be an estimation derived from experimentation data. The term $f(C|G)$ may be or include one or more probability distribution functions. The term $f(C|G)$ may be or include one or more probability distribution functions provided according to the seventh aspect of the invention. The term $f(C|G)$ may be or may be as further defined in the second aspect of the invention.

The method of comparing may involve a likelihood ratio which is not conditioned on quantity of DNA in the first and/or second sample.

The method of comparing may involve a likelihood ratio which is conditioned on quantity of DNA in the first and/or second sample.

The method of comparing may include defining the term f(C|G) as being defined by:

$$f(C\mid G) = \sum_j f(C\mid G, \chi_j) Pr(\chi_j \mid I(h))$$

where $Pr(\chi_j|I(h))$ is a probability distribution of DNA quantity given peak height information, I(h), preferably experimentally derived.

The term f(C|G) may be conditioned on DNA quantity in the test sample in this way. The term f(C|G) and/or $f(C|G,\chi_i)$ may be or may be as further defined in the third aspect of the invention.

The term $f(C|G,\chi_i)$ may be an estimation. The term $f(C|G,\chi_i)$ may be derived from experimental data. The term $f(C|G,\chi_i)$ may be an estimation derived from experimentation data. The term $f(C|G,\chi_i)$ may be or include one or more probability distribution functions. The term $f(C|G,\chi_i)$ may be or include one or more probability distribution functions provided according to the seventh aspect of the invention. The term $f(C|G,\chi_i)$ may be or may be as further defined in the third aspect of the invention.

The method of comparing may be used to gather information to assist further investigations or legal proceedings. The method of comparing may provide intelligence on a situation. The method of comparison may be of the likelihood of the information of the first or test sample result given the information of the second or another sample result. The method of comparison may provide a listing of possible another sample results, ideally ranked according to the likelihood. The method of comparison may seek to establish a link between a DNA profile from a crime scene sample and one or more DNA profiles stored in a database.

The method of comparison may consider a likelihood ratio. Preferably the likelihood ratio, more preferably the posterior probability, is defined as:

$$Pr(G_i\mid C) = \frac{f(C\mid G_i) Pr(G_i)}{\sum_i f(C\mid G_i) Pr(G_i)}$$

where:

C is the first or test result set from a test sample, more particularly, the first result set taken from a sample recovered from a person or location linked with a crime, potentially expressed in terms of peak positions and/or heights;

$G_i$ is the second or another result set, more particularly, the various members of an exhaustive list of potential donor genotypes; and $Pr(G_i)$ is a prior distribution for genotype $G_i$, preferably computed for a population, particularly the population from which the test sample under consideration comes. It can be computed using the formulae introduced by Balding et al. (1996).

The comparison may include consideration of the term: $f(C|G_i)$. The method may include any of the features, options or possibilities proposed for f(C|G) applying to $f(C|G_i)$.

The method of comparing may involve a likelihood ratio which is not conditioned on quantity of DNA in the first and/or second sample.

The method of comparing may involve a likelihood ratio which is conditioned on quantity of DNA in the first and/or second sample.

The method of comparing may include defining the term $Pr(G_i|C)$ as being defined by:

$$Pr(G_i\mid C) = \frac{\left[\sum_j f(C\mid G_i, \chi_j) Pr(\chi_j\mid I(h))\right] \times Pr(G_i)}{\sum_i \left[\sum_j f(C\mid G_i, \chi_j) Pr(\chi_j\mid I(h))\right] \times Pr(G_i)}$$

where $Pr(\chi_j|I(h))$ is a probability distribution of DNA quantity given information on peak heights.

The term $Pr(\chi_j|I(h))$ may be or may be as further defined in the fourth aspect of the invention.

The term $f(C|G_1,G_2)$ may be or may be as further defined in the fifth aspect of the invention.

The term $f(C|G_1,G_2,\chi_i)$ may be or may be as further defined in the sixth aspect of the invention.

The method of comparing may be used in one or more of the following situations:

1) in an evidential context, for a single source sample, without conditioning on DNA quantity;
2) in an evidential context, for a single source sample, with conditioning on DNA quantity;
3) in an intelligence context, for a single source sample, without conditioning on DNA quantity;
4) in an intelligence context, for a single source sample, with conditioning on DNA quantity;
5) in an evidential context, for a mixed source sample, without conditioning on DNA quantity;
6) in an evidential context, for a mixed source sample, with conditioning on DNA quantity;
7) in an intelligence context, for a mixed source sample, without conditioning on DNA quantity; and
8) in an intelligence context, for a mixed source sample, with conditioning on DNA quantity.

According to a second aspect of the invention we provide a method of comparing a first, potentially test, sample result set with a second, potentially another, sample result set, the method including:

providing information for the first result set on the one or more identities detected for a variable characteristic of DNA;

providing information for the second result set on the one or more identities detected for a variable characteristic of DNA; and wherein the method uses the factor f(C|G) or a factor incorporating that factor, where means f this is an expression of likelihood, C is the information of the first result set and G is the information of the second result set.

The factor f(C|G) may be an expression of the likelihood of observing the information of the first result set given that the information of the second result set. The factor f(C|G) may be an expression of the likelihood of observing the information from a sample taken from a crime scene given the information in a given genotype, particularly the genotype of a suspect and/or another person.

The comparison may include the consideration of this term as, or as a component of, the denominator of a likelihood ratio, and/or the consideration of this term as, or as a component of, the nominator of a likelihood ratio. The likelihood ratio may be of the form:

$$LR = \frac{Pr(C \mid S, H_p)}{Pr(C \mid S, H_d)}$$

where

C is the first result set from a test sample, more particularly, the first result set taken from a sample recovered from a person or location linked with a crime, potentially expressed in terms of peak positions and/or heights;

S is the second result set, more particularly, the second result set taken from a sample collected from a person, particularly expressed as a suspect's genotype;

$H_p$ is one hypothesis, more particularly the prosecution hypothesis in legal proceedings stating "The suspect left the sample at the scene of crime";

$H_d$ is an alternative hypothesis, more particularly the defence hypothesis in legal proceedings stating "Someone else left the sample at the crime scene".

The term f(C|G) may be an estimation. The term f(C|G) may be derived from experimental data. The term f(C|G) may be an estimation derived from experimentation data. The term f(C|G) may be or include one or more probability distribution functions. The estimation of the term f(C|G) may be provided by the consideration of dilution data, particularly data collected from heterozygous sources and/or, and preferably separately, from heterozygous sources. The estimation of f(C|G) may be provided by grouping control sample analysis data from one or more loci of interest together. A single estimation of f(C|G) covering all the loci for which information is stored in a database and/or which are analysed using an analysis method and/or which are analysed using a multiplex amplification product may be provided. A separate estimation of f(C|G) may be provided for each locus. The estimation of f(C|G) may be generated using two-dimensional density estimations and/or two-dimensional probability distribution functions.

The term f(C|G) may be or include, and/or be computed using, one or more probability distribution functions provided according to the seventh aspect of the invention.

The term f(C|G) may be used to calculate the term: $f(C|S, H_p)$ and/or the term $f(C|U_i, S, H_d)$.

The likelihood ratio of the form:

$$LR = \frac{Pr(C \mid S, H_p)}{Pr(C \mid S, H_d)}$$

may be defined as:

$$LR = \frac{Pr(C \mid S, H_p)}{\sum_i Pr(C \mid U_i, S, H_d) Pr(U_i \mid S)}$$

where $U_i$ is one of the supposed sources stated in $H_d$.

The likelihood ratio of the form:

$$LR = \frac{Pr(C \mid S, H_p)}{Pr(C \mid S, H_d)}$$

may be defined as:

$$LR = \frac{f(C \mid S, H_p)}{\sum_i f(C \mid U_i, S, H_d) Pr(U_i \mid S)}$$

where the f terms are factors that are likelihoods.

The factor $Pr(U_i|S)$ may be computed by using a subpopulation structure equation, such as the subpopulation structure equation described in D. J. Balding (2005), "Weight-of-evidence for forensic DNA profiles", John Wiley & Sons Ltd and/or J. Buckleton, C. M. Triggs, S. J. Walsh (2005), "Forensic DNA evidence interpretation. CRC Press".

The method of comparing may consider one or more of the following scenarios for the suspect and/or information observed in the analysis:

a) Suspect is heterozygous and crime profile has one peak;
b) Suspect is heterozygous and crime profile has two peaks;
c) Suspect is heterozygous and the crime profile contains no peaks;
d) Suspect is homozygous and crime profile contains one peak;
e) Suspect is homozygous and crime profile contains no peaks.

Where the suspect is heterozygous, stated as S={a,b}, and the test sample or first sample has one peak, stated as C={$h_b$}, the likelihood ratio may be defined as:

$$LR = \frac{f(C = \{h_b\} \mid S = \{a, b\}, H_p)}{f(C = \{h_b\} \mid S = \{a, b\}, H_d)}$$

Preferably the numerator in this likelihood ratio is defined as:

$$f(C = \{h_a < t, h_b\} \mid S = \{a, b\}, H_p) = f_{het}(h_a < t, h_b) = \int_0^t f_{het}(h_a, h_b) dh_a$$

where $h_a$ is a peak height or peak area or peak weight smaller than a detection threshold and so is not observed in the results.

Preferably the denominator in this likelihood ratio is defined as:

$$f(C=\{h_b\}|H_d)=f(C=\{h_b\}|U=\{b,b\},H_d)Pr(U=\{b,b\}|S=\{a,b\}H_d)+f(C=\{h_b\}|U=\{b,Q\}H_d)Pr(U=\{b,Q\}|S=\{a,b\}H_d).$$

where Q is any other allele identity than a.

The factors $Pr(U=\{b,b\}|S=\{a,b\}H_d)$ and $Pr(U=\{b,Q\}|S=\{a,b\} H_d)$, may be computed using the population substructure calculations described in D. J. Balding, M. Greenhalgh, R. A. Nichols (1996), "Population genetics of STR loci in Caucasians", 108:300-305.

The factor may consider:

$$Pr(C=\{h_b\}|U=\{b,b\},H_d)=f_{het}(0.5h_b,0.5h_b)$$

where $f_{het}$ is a two-dimensional pdf on pairs of heights originating from heterozygous donors.

The factor may consider the position as relating to or equating to the solution described below at the bottom of page 8.

The factor may consider the position as $f_{hom}$ and point to a description of solutions, for instance as:

$$Pr(C=\{h_b\}|U=\{b,b\},H_d)=f_{hom}(h_b)$$

The factor may consider:

$$f(C = \{h_b\} \mid U = \{b, Q\}, H_d) = f_{het}(h_b, h_Q < t) = \int_0^{Td} f_{het}(h_b, h_Q)\, dh_a$$

where $h_Q$ is smaller than the threshold t.

Where the suspect is heterozygous, stated as S={a,b}, and the first or test sample gives two peaks, stated as C={$h_a,h_b$}, the LR may be defined as:

$$LR = \frac{f(C = \{h_a, h_b\} \mid S = \{a, b\}, H_p)}{f(C = \{h_a, h_b\} \mid S = \{a, b\}, H_d)}$$

The numerator in this LR may be defined by:

$$f(C=\{h_a,h_b\}|S=\{a,b\},H_d)=f_{het}(h_a,h_b)$$

The denominator is given by:

$$f(C=\{h_a,h_b\}|S=\{a,b\},H_d)=f_{het}(h_a,h_b)Pr(U=\{a,b\}|S=\{a,b\},H_d)$$

The LR may be defined as:

$$LR = \frac{1}{Pr(U = \{a, b\} \mid S = \{a, b\}H_d)}$$

Where the suspect is heterozygous, stated as S={b,b}, and the first or test sample provides a profile containing one allele, stated as C={$h_b$}, the LR may be defined as:

$$LR = \frac{f(C = \{h_b\} \mid S = \{b, b\}, H_p)}{f(C = \{h_b\} \mid S = \{b, b\}, H_d)}$$

The numerator may be given by:
f(C={$h_b$}|S={b,b},$H_p$)=$f_{hom}(h_b)$ which may be a density function estimated for homozygous contributors.

The denominator may be given by:

$$f(C = \{h_b\} \mid S = \{b, b\}, H_d) =$$
$$f(C = \{h_b\} \mid U = \{b, b\}, H_d)Pr(U = \{b, b\} \mid S = \{b, b\}) +$$
$$f(C = \{h_b, h_Q < Td\} \mid U = \{b, Q\}, H_d)Pr(U = \{b, Q\} \mid S = \{b, b\}).$$

The term: f(C={$h_b$}|U={b,b},S={b,b},$H_d$)=$f_{hom}(h_b)$ is the same as the numerator.

The term:

$$f(C = \{h_b, h_Q < Td\} \mid U = \{b, Q\}, H_d) = \int_0^{Td} f_{het}(h_b, h_Q)\, dq$$

can be obtained by estimating a pdf for the peak heights.

Where the suspect is homozygous, stated as C={$h_b$}, and the test or first sample provides a profile containing one allele, $h_b$, the likelihood for a homozygous donor may be given by:

$$f(C=\{h_b\}|G=\{b,b\})=f_{hom}(h_b)$$

where $f_{hom}$ can be computed by several methods, for example by the method of rotation described elsewhere in this document and/or by the method:

$$f_{hom}(h_b) = \int_0^1 f_{het}(\alpha h_b, (1-\alpha)h_b) f(\alpha)\, d\alpha$$

where $f_{het}(\alpha h_b,(1-\alpha)h_b)$ is a two-dimensional probability density function computed for a heterozygote and $f(\alpha)$ is a probability density function for α, where α is the proportion of the homozygote given by one of the alleles of the homozygote and 1–α is the proportion accounted by the other allele of the homozygote.

The function may be approximated by:

$$f_{hom}(h_b)=f_{het}(\alpha h_b,(1-\alpha)h_b)$$

for an α close to 0.5.

The method of comparing may be used to gather information to assist further investigations or legal proceedings. The method of comparing may provide intelligence on a situation. The method of comparison may be of the likelihood of the information of the first or test sample result given the information of the second or another sample result. The method of comparison may provide a listing of possible another sample results, ideally ranked according to the likelihood. The method of comparison may seek to establish a link between a DNA profile from a crime scene sample and one or more DNA profiles stored in a database.

The method may include taking a crime scene DNA profile, C, and determining an ordered list of suspect's profiles, where the first profile in the list is the genotype of the most likely donor. The method may propose a list of genotypes {$G_1$, $G_2$, . . . ,$G_m$} and then rank those genotypes according the posterior probability of the genotype given the crime scene profile, C.

The method of comparison may consider a likelihood ratio or more preferably posterior probability. Preferably the likelihood ratio, more preferably posterior probability, is defined as:

$$Pr(G_i \mid C) = \frac{f(C \mid G_i)Pr(G_i)}{\sum_i f(C \mid G_i)Pr(G_i)}$$

where:

C is the first or test result set from a test sample, more particularly, the first result set taken from a sample recovered from a person or location linked with a crime, potentially expressed in terms of peak positions and/or heights;

$G_i$ is the second or another result set, more particularly, the various members of an exhaustive list of potential donor genotypes; and Pr($G_i$) is a prior distribution for genotype $G_i$, preferably computed for a population, particularly the population from which the test sample under consideration comes. It can be set to be a uniform distribution or computed using genotype probabilities formulae described in Blading (2005) and Buckleton et al. (2005), both referenced above.

The comparison may include consideration of the term: f(C|$G_i$). the method may include any of the features, options or possibilities proposed for f(C|G) applying to f(C|$G_i$). According to a third aspect of the invention we provide a method of comparing a first, potentially test, sample result set with a second, potentially another, sample result set, the method including:

providing information for the first result set on the one or more identities detected for a variable characteristic of DNA;

providing information for the second result set on the one or more identities detected for a variable characteristic of DNA; and wherein the method uses the factor f(C|G) or a factor incorporating that factor, where $$f(C \mid G) = \sum_j f(C \mid G, \chi_j) Pr(\chi_j \mid I(h))$$

where f means this is an expression of likelihood, C is the information of the first result set and G is the information of the second result set, where $Pr(\chi_j|I(h))$ is a probability distribution of DNA quantity, $\chi_j$, given a quantitative measure of the one or more identities considered in the first result set and/ort second result set, I(h).

Preferably $Pr(\chi_j|I(h))$ is a probability distribution of DNA quantity with peak height and/or peak area/and/or peak weight.

Preferably the factor $f(C|G,\chi_i)$ is computed by conditioning on DNA quantity.

The factor $f(C|G,\chi_i)$ may be an expression of the likelihood of observing the information of the first result set given that the information of the second result set. The factor $f(C|G,\chi_i)$ may be an expression of the likelihood of observing the information from a sample taken from a crime scene given the information in a given genotype, particularly the genotype of a suspect and/or another person.

The term $f(C|G,\chi_i)$ may be an estimation. The term $f(C|G,\chi_i)$ may be derived from experimental data. The term $f(C|G,\chi_i)$ may be an estimation derived from experimentation data. The term $f(C|G,\chi_i)$ may be or include one or more probability distribution functions. The estimation of the term $f(C|G,\chi_i)$ may be provided by the consideration of dilution data, particularly data collected from heterozygous sources and/or, and preferably separately, from heterozygous sources.

The estimation of $f(C|G,\chi_i)$ may be provided by grouping together control sample analysis data for the same quantity of DNA. A separate estimation of $f(C|G,\chi_i)$ may be provided for each quantity of DNA. The quantities of DNA for which the factor $f(C|G,\chi_i)$ is estimated may be spaced across a range, preferably evenly so.

The estimation of $f(C|G,\chi_i)$ may be provided by grouping control sample analysis data from one or more loci of interest together. A single estimation of $f(C|G,\chi_i)$ covering all the loci for which information is stored in a database and/or which are analysed using an analysis method and/or which are analysed using a multiplex amplification product may be provided. A separate estimation of $f(C|G,\chi_i)$ may be provided for each locus. The estimation of $f(C|G,\chi_i)$ may be generated using two-dimensional density estimations and/or two-dimensional probability distribution functions.

The term $f(C|G,\chi_i)$ may be or include, and/or be computed using, one or more probability distribution functions provided according to the seventh aspect of the invention.

The method of comparing may be used to gather information to assist further investigations or legal proceedings. The method of comparing may provide intelligence on a situation. The method of comparison may be of the likelihood of the information of the first or test sample result given the information of the second or another sample result. The method of comparison may provide a listing of possible another sample results, ideally ranked according to the likelihood. The method of comparison may seek to establish a link between a DNA profile from a crime scene sample and one or more DNA profiles stored in a database.

The method may include taking a crime scene DNA profile, C, and determining an ordered list of suspect's profiles, where the first profile in the list is the genotype of the most likely donor. The method may propose a list of genotypes $\{G_1, G_2, \ldots, G_m\}$ and then rank those genotypes according the posterior probability of the genotype given the crime scene profile, C.

The method of comparison may consider a likelihood ratio. Preferably the likelihood ratio is defined as:

$$Pr(G_i \mid C) = \frac{\left[\sum_j f(C \mid G_i, \chi_j) Pr(\chi_j \mid I(h))\right] \times Pr(G_i)}{\sum_i \left[\sum_j f(C \mid G_i, \chi_j) Pr(\chi_j \mid I(h))\right] \times Pr(G_i)}$$

where $Pr(\chi_j|I(h))$ is a probability distribution of DNA quantity, $\chi_j$, given a quantitative measure of the one or more identities considered in the first result set and/ort second result set, I(h), more preferably, where $Pr(\chi_j|I(h))$ is a probability distribution of DNA quantity given information on peak heights.

According to a fourth aspect of the invention we provide a method of comparing a first, potentially test, sample result set with a second, potentially another, sample result set, the method including:

providing information for the first result set on the one or more identities detected for a variable characteristic of DNA;

providing information for the second result set on the one or more identities detected for a variable characteristic of DNA; and wherein the method uses the factor $Pr(\chi_j|I(h))$ or a factor incorporating that factor, where $Pr(\chi_j|I(h))$ is a probability distribution of DNA quantity, $\chi_j$, given a quantitative measure of the one or more identities considered in the first result set and/ort second result set, I(h).

Preferably $Pr(\chi_j|I(h))$ is a probability distribution of DNA quantity with peak height and/or peak area and/or peak weight.

Preferably the probability distribution for $Pr(\chi_j|I(h))$ relates to a list of discrete probabilities for $\chi_1$ to $\chi_j$, where $\Sigma_i Pr(\chi_i)=1$. Preferably the distribution is obtained by considering the observed distribution obtained from the analysis of the control samples.

The quantitative measure may be the mean value for all observed values across all loci. The quantitative measure may be the mean of all values for a single locus. The quantitative measure may be the mean value for all the observed values for all loci for a given quantity of DNA. The quantitative measure may be the mean value for all the observed values for a single locus for a given quantity of DNA.

The quantitative measure may be peak height and/or peak area and/or peak weight.

A distribution may be estimated. The distribution may be of the form $f(\bar{h}|\chi_i)$ preferably where $\bar{h}$ is the mean conditional on a DNA quantity $\chi_i$.

The calculation of $Pr(X\chi_i|I(h))$ for a locus may be performed in a sequential fashion based on an ordering $L_1, L_2, \ldots, L_n$ of the loci. The calculation may begin by setting $Pr(X=\chi_i|I(h))$ for $L_1$ to a uniform distribution. Another assumed form for the distribution may be used. The calculation for the next locus, $L_2$, of $Pr(X=\chi_i|I(h))$ may be based on the assumption for I(h) from $L_1$. The subsequent calculations for the subsequent loci may be based upon the assumption for I(h) for all the loci which precede it in the calculation, for instance $Pr(X=\chi_a|I(h))$ for $L_n$ is computed based on I(h) from $L_1, L_2, \ldots, L_{n-1}$.

The term $Pr(X=\chi_a|I(h))$ may be an estimation. The term $Pr(X=\chi_a|I(h))$ may be derived from experimental data. The term $Pr(X=\chi_a|I(h))$ may be an estimation derived from experimentation data. The term $Pr(X=\chi_a|I(h))$ may be or include one or more probability distribution functions. The estimation of the term $Pr(X=\chi_a|I(h))$ may be provided by the consideration of dilution data, particularly data collected from heterozygous sources and/or, and preferably separately, from heterozygous sources.

The estimation of $Pr(X=\chi_a|I(h))$ may be provided by grouping together control sample analysis data for the same quantity of DNA. A separate estimation of $Pr(X=\chi_a|I(h))$ may be provided for each quantity of DNA. The quantities of DNA for which the factor $Pr(X=\chi_a|I(h))$ is estimated may be spaced across a range, preferably evenly so.

The estimation of $Pr(X=\chi_a|I(h))$ may be provided by grouping control sample analysis data from one or more loci of interest together. A single estimation of $Pr(X=\chi_a|I(h))$ covering all the loci for which information is stored in a database and/or which are analysed using an analysis method and/or which are analysed using a multiplex amplification product may be provided. A separate estimation of $Pr(X=\chi_a|I(h))$ may be provided for each locus. The estimation of $Pr(X=\chi_a|I(h))$ may be generated using two-dimensional density estimations and/or two-dimensional probability distribution functions.

The term $Pr(X=\chi_a|I(h))$ may be or include, and/or be computed using, one or more probability distribution functions provided according to the seventh aspect of the invention.

According to a fifth aspect of the invention we provide a method of comparing a first, potentially test, sample result set with a second, potentially another, sample result set, the method including:
- providing information for the first result set on the one or more identities detected for a variable characteristic of DNA;
- providing information for the second result set on the one or more identities detected for a variable characteristic of DNA; and
- wherein the method uses the factor $f(C|G_1,G_2)$ or a factor incorporating that factor, where preferably f means this is an expression of likelihood, C is the information of the first result set and where $G_1$ and $G_2$ is the information of the second result set.

The factor $f(C|G_1,G_2)$ may be used to calculate the factors $f(C|S,U_i,H_p)$ and $f(C|U_j,U_k,S,H_d)$. The factors $f(C|S,U_i,H_p)$ and $f(C|U_j,U_k,S,H_d)$ may be the expression of the likelihood of the crime profile C given two supposed sources or donors; potentially according to a hypothesis of the defence, $H_d$, and/or prosecution, $H_p$. $G_1$ and $G_2$ may be the genotypes of the supposed donors or sources.

The method may involve the consideration, particularly in an evidential context, particularly for a mixed source sample arising from two contributors, of the prosecution and defence hypotheses. The hypotheses may be: the prosecution hypothesis, $H_p$, that the suspect and someone else are the donors to the first result set, potentially a stain at the scene of crime; and/or the defence hypothesis, $H_d$, that two unknown people are the donors to the first result set, potentially a stain at the scene of crime. The hypotheses may be: the prosecution hypothesis, $H_p$, that the suspect and the victim are the donors to the first result set, and/or the defence hypothesis, $H_d$, that the victim and unknown person are the donors to the first result set. The hypotheses may be: the prosecution hypothesis, $H_p$, that the two suspects are the donors to the first result set, and/or the defence hypothesis, $H_d$, that the two unknown persons are the donors to the first result set. One or both hypotheses may involve statements of relatedness amongst the possible contributors.

The LR may be given by the formula:

$$LR = \frac{Pr(C|S, H_p)}{Pr(C|S, H_d)}$$

where
- C is the first result set from a test sample, more particularly, the first result set taken from a sample recovered from a person or location linked with a crime, potentially expressed in terms of peak positions and/or heights;
- S is the second result set, more particularly, the second result set taken from a sample collected from a person, particularly expressed as a suspect's genotype;
- $H_p$ is one hypothesis, more particularly the prosecution hypothesis in legal proceedings stating "The suspect left the sample at the scene of crime";
- $H_d$ is an alternative hypothesis, more particularly the defence hypothesis in legal proceedings stating "Someone else left the sample at the crime scene".

The LR formula can be written as:

$$LR = \frac{\sum_i f(C|S, U_i, H_p) Pr(U_i|S, H_p)}{\sum_j \sum_k f(C|U_j, U_k, S, H_d) Pr(U_j, U_k|S, H_d)}$$

where $f(C|S,U_i,H_p)$ is a density function of C given S and $U_i$ and $f(C|U_j,U_k,S,H_d)$ is a density function of C given $U_j$, $U_k$ and S.

The factors $Pr(U_i|S,H_p)$ and $Pr(U_j,U_k|S,H_d)$ may be computed using the formulae described in Balding (2005) and Buckleton (2005), referenced above, which may include considerations of relatedness between the unknown contributors and the suspect.

The factor $f(C|G_1,G_2)$ may be an expression of the likelihood of observing the information of the first result set given that the information of the second result set. The factor $f(C|G_1,G_2)$ may be an expression of the likelihood of observing the information from a sample taken from a crime scene given the information in a given genotype, particularly the genotype of a suspect and/or another person.

The term $f(C|G_1,G_2)$ may be an estimation. The term $f(C|G_1,G_2)$ may be derived from experimental data. The term $f(C|G_1,G_2)$ may be an estimation derived from experimentation data. The term $f(C|G_1,G_2)$ may be or include one or more probability distribution functions. The estimation of the term $f(C|G_1,G_2)$ may be provided by the consideration of dilution data, particularly data collected from heterozygous sources and/or, and preferably separately, from heterozygous sources.

The estimation of $f(C|G_1,G_2)$ may be provided by grouping together control sample analysis data for the same quantity of DNA. A separate estimation of $f(C|G_1,G_2)$ may be provided for each quantity of DNA. The quantities of DNA for which the factor $f(C|G_1,G_2)$ is estimated may be spaced across a range, preferably evenly so.

The estimation of $f(C|G_1,G_2)$ may be provided by grouping control sample analysis data from one or more loci of interest together. A single estimation of $f(C|G_1,G_2)$ covering all the loci for which information is stored in a database and/or which are analysed using an analysis method and/or which are analysed using a multiplex amplification product may be provided. A separate estimation of $f(C|G_1,G_2)$ may be provided for each locus. The estimation of $f(C|G_1,G_2)$ may be generated using two-dimensional density estimations and/or two-dimensional probability distribution functions.

The term $f(C|G_1,G_2)$ may be or include, and/or be computed using, one or more probability distribution functions provided according to the seventh aspect of the invention.

The method may involve a consideration of one or more of the following scenarios, particularly in an evidential context:
 a) Suspect and victim are heterozygous, with no overlapping alleles between them and only three peaks in the crime profile; and
 b) Suspect and victim are heterozygous, with one overlapping allele between them and only three peaks in the crime profile.

In both scenarios, where we are considering likelihood ratios for a locus, in respect of a sample from two sources, there are two basic hypotheses which may be considered:
 $H_p$: The suspect (S) and the victim (V) are the originators of the crime profile, the hypothesis of the prosecution; and
 $H_d$: The victim (V) and an unknown (U) are the originators of the crime profile, the hypothesis of the defence.

Where there is a heterozygous suspect and victim with no overlapping alleles and three peaks in the crime profile, then $H_p$ may be V+S, and $H_d$ may be V+U, $C=\{h_a,h_b,h_c\}$, $V=\{a,b\}$ and $S=\{c,d\}$. The LR may be given by:

$$LR = \frac{f(C=\{h_a, h_b, h_c\} \mid V=\{a,b\}, S=\{c,d\}, H_p)}{f(C=\{h_a, h_b, h_c\} \mid V=\{a,b\}, S=\{c,d\}, H_d)}$$

The numerator in this function may be given by:

$$f(C=\{h_a,h_b,h_c\}|V=\{a,b\},S=\{c,d\},H_p)=f_{het}(h_a,h_b) \times f_{het}(h_c,h_d)$$

The unknown contributors for the denominators can be $\{a,c\}$, $\{b,c\}$, $\{c,Q\}$. The denominator may be given by:

$$f(C=\{h_a,h_b,h_c\} \mid V=\{a,b\}, S=\{c,d\}, H_d) =$$
$$f(C=\{h_a,h_b,h_c\} \mid V=\{a,b\}, S=\{c,d\}, U=\{a,c\}, H_d)$$
$$Pr(U=\{a,c\} \mid S=\{a,b\}) +$$
$$f(C=\{h_a,h_b,h_c\} \mid V=\{a,b\}, S=\{c,d\}, U=\{b,c\}, H_d)$$
$$Pr(U=\{b,c\} \mid S=\{a,b\}) +$$
$$f(C=\{h_a,h_b,h_c\} \mid V=\{a,b\}, S=\{c,d\}, U=\{c,Q\}, H_d)$$
$$Pr(U=\{a,c\} \mid S=\{a,b\}).$$

The factor for $U=\{a,c\}$ may be computed with the formula:

$$f(C=\{h_a,h_b,h_c\}|V=\{a,b\},U=\{a,c\},H_d)=f_{het}(m_x h_a,h_b) \times f_{het}((1-m_x)h_a,h_c).$$

The factor for $U=\{b,c\}$ may be computed with the formula:

$$f(C=\{h_a,h_b,h_c\}|V=\{a,b\},U=\{b,c\},H_d)=f_{het}(h_a,m_x h_b) \times f_{het}(h_a,(1-m_x)h_c).$$

The factor for $U=\{c,Q\}$ may be computed with the formula:

$$f(C=\{h_a,h_b,h_c\}|V=\{a,b\},U=\{c,Q\},H_d)=f_{het}(h_a,h_b) \times f_{het}(h_c,h_Q).$$

Where the heterozygous suspect and victim are with one overlapping allele and three peaks in the crime profile, then $H_p$ may be V+S, and $H_d$ may be V+U, $C=\{h_a,h_b,h_c\}$, $V=\{a,b\}$ and $S=\{b,c\}$. The likelihood ratio may be given by:

$$LR = \frac{f(C=\{h_a, h_b, h_c\} \mid V=\{a,b\}, S=\{b,c\}, H_p)}{f(C=\{h_a, h_b, h_c\} \mid V=\{a,b\}, S=\{b,c\}, H_d)}$$

The numerator may be given by:

$$Pr(C=\{h_a,h_b,h_c\}|V=\{a,b\},S=\{b,c\},H_p)=f_{het}(h_a,m_x h_b) f_{het}((1-m_x)h_b,h_c).$$

The denominator may consider the following potential unknown contributors:

$$U \in \{\{a,c\},\{b,c\},\{c,c\},\{c,Q\}\}.$$

The function may be computed, where $U=\{a,c\}$, using:

$$Pr(C=\{h_a,h_b,h_c\}|V=\{a,b\},S=\{b,c\},U=\{a,c\},H_d)=f_{het}(m_x h_a,h_b) f_{het}((1-m_x)h_a,h_c)\pi(\ )$$

The function may be computed, where $U=\{b,c\}$ using:

$$f(C=\{h_a,h_b,h_c\}|V=\{a,b\},U=\{b,c\},H_d)=f_{het}(h_a,m_x h_b) f_{het}((1-m_x)h_b,h_c).$$

The function may be computed, where $U=\{c,c\}$ using:

$$f(C=\{h_a,h_b,h_c\}|V=\{a,b\},U=\{c,c\}H_d)=f_{het}(h_a,h_b) f_{het}(0.5h_c,0.5h_c)$$

The function may be computed, where $U=\{c,Q\}$, using:

$$f(C=\{h_a,h_b,h_c\}|V=\{a,b\},U=\{c,Q\}H_d)=f_{het}(h_a,h_b) f_{het}(h_c,h_Q).$$

The method of comparing may be used to gather information to assist further investigations or legal proceedings. The method of comparing may provide intelligence on a situation. The method of comparison may be of the likelihood of the information of the first or test sample result given the information of the second or another sample result. The method of comparison may provide a listing of possible another sample results, ideally ranked according to the likelihood. The method of comparison may seek to establish a link between a DNA profile from a crime scene sample and one or more DNA profiles stored in a database.

The method may include taking a crime scene DNA profile, C, and determining an ordered list of suspect's profiles, where the first profile in the list is the genotype of the most likely donor. The method may propose a list of genotypes $\{G_1, G_2, \ldots, G_m\}$ and then rank those genotypes according the posterior probability of the genotype given the crime scene profile, C.

The method of comparison may consider a posterior probability. Preferably posterior probability is defined as:

$$Pr(G_{1,i}, G_{2,i} \mid C) = \frac{f(C \mid G_{1,i}, G_{2,i}) Pr(G_{1,i}, G_{2,i})}{\sum_i f(C \mid G_{1,i}, G_{2,i}) Pr(G_{1,i}, G_{2,i})}$$

The method may propose an ordered list of pairs of genotypes $G_1$ and $G_2$ per locus, preferably so that the first pair in the list in the most likely donor of the crime stain.

The method may start with a first set of results, for instance, crime stain profile C. The method may then provide a list, potentially an exhaustive list $\{G_{1,i}, G_{2,i}\}$, of pairs of potential donors is generated. Preferably for each of theses pairs, a probability distribution for the genotypes is calculated using the formula:

$$Pr(G_{1,i}, G_{2,i} \mid C) = \frac{f(C \mid G_{1,i}, G_{2,i}) Pr(G_{1,i}, G_{2,i})}{\sum_i f(C \mid G_{1,i}, G_{2,i}) Pr(G_{1,i}, G_{2,i})}$$

where $Pr(G_{1,i},G_{2,i})$ is a prior distribution for the pair of genotypes inside the brackets that can be set to be a uniform distribution or computed using the probabilities of genotypes described in Balding (2005) and Buckleton et al. (2005), referenced above.

According to a sixth aspect of the invention we provide a method of comparing a first, potentially test, sample result set with a second, potentially another, sample result set, the method including:

providing information for the first result set on the one or more identities detected for a variable characteristic of DNA;
  providing information for the second result set on the one or more identities detected for a variable characteristic of DNA; and
  wherein the method uses the factor $f(C|G_1,G_2,\chi_i)$ or a factor incorporating that factor, where preferably f means this is an expression of likelihood, C is the information of the first result set and where $G_1$ and $G_2$ is the information of the second result set, $\chi_i$ is a quantitative measure of the one or more identities considered in the first result set and/or second result set.

The factor $f(C|G_1,G_2,\chi_i)$ may be used to calculate the factors $f(C|S,U_i,H_p)$ and $f(C|U_j,U_k,S,H_d)$. The factors $f(C|S,U_i,H_p)$ and $f(C|U_j,U_k,S,H_d)$ may be the expression of the likelihood of the crime profile C given two supposed sources or donors; potentially according to a hypothesis of the defence, $H_d$, and/or prosecution, $H_p$. $G_1$ and $G_2$ may be the genotypes of the supposed donors or sources.

The method may involve the consideration, particularly in an evidential context, particularly for a mixed source sample arising from two contributors, of the prosecution and defence hypotheses. The hypotheses may be: the prosecution hypothesis, $H_p$, that the suspect and someone else are the donors to the first result set, potentially a stain at the scene of crime; and/or the defence hypothesis, $H_d$, that two unknown people are the donors to the first result set, potentially a stain at the scene of crime.

The LR may be given by the formula:

$$LR = \frac{Pr(C \mid S, H_p)}{Pr(C \mid S, H_d)}$$

where

C is the first result set from a test sample, more particularly, the first result set taken from a sample recovered from a person or location linked with a crime, potentially expressed in terms of peak positions and/or heights;
  S is the second result set, more particularly, the second result set taken from a sample collected from a person, particularly expressed as a suspect's genotype; and/or
  $H_p$ is one hypothesis, more particularly the prosecution hypothesis in legal proceedings stating "The suspect is one of the contributors of the crime stain obtained";
  $H_d$ is an alternative hypothesis, more particularly the defence hypothesis in legal proceedings stating "Two unknown persons are the donors of the crime stain".

The LR formula can be written as:

$$LR = \frac{\sum_i f(C \mid S, U_i, H_p) Pr(U_i \mid S)}{\sum_j \sum_k f(C \mid U_j, U_k, S, H_d) Pr(U_j, U_k \mid S)}$$

where $f(C|S,U_i,H_p)$ is a density function of C given S and $U_i$ and $f(C|U_j,U_k,S,H_d)$ is a density function of C given $U_j$, $U_k$ and S.

The factors $Pr(U_i|S,H_p)$ and $Pr(U_j,U_k|S,H_d)$ may be computed by the methods described in Balding (2005) and Buckleton (2005), referenced above, which may include considerations of relatedness.

The factor $f(C|G_1,G_2,\chi_i)$ may be an expression of the likelihood of observing the information of the first result set given that the information of the second result set. The factor $f(C|G_1,G_2,\chi_i)$ may be an expression of the likelihood of observing the information from a sample taken from a crime scene given the information in a given genotype, particularly the genotype of a suspect and/or another person.

The term $f(C|G_1,G_2,\chi_i)$ may be an estimation. The term $f(C|G_1,G_2,\chi_i)$ may be derived from experimental data. The term $f(C|G_1,G_2,\chi_i)$ may be an estimation derived from experimentation data. The term $f(C|G_1,G_2,\chi_i)$ may be or include one or more probability distribution functions. The estimation of the term $f(C|G_1,G_2,\chi_i)$ may be provided by the consideration of dilution data, particularly data collected from heterozygous sources and/or, and preferably separately, from heterozygous sources.

The estimation of $f(C|G_1,G_2,\chi_i)$ may be provided by grouping together control sample analysis data for the same quantity of DNA. A separate estimation of $f(C|G_1,G_2,\chi_i)$ may be provided for each quantity of DNA. The quantities of DNA for which the factor $f(C|G_1,G_2,\chi_i)$ is estimated may be spaced across a range, preferably evenly so.

The estimation of $f(C|G_1,G_2,\chi_i)$ may be provided by grouping control sample analysis data from one or more loci of interest together. A single estimation of $f(C|G_1,G_2,\chi_i)$ covering all the loci for which information is stored in a database and/or which are analysed using an analysis method and/or which are analysed using a multiplex amplification product may be provided. A separate estimation of $f(C|G_1,G_2,\chi_i)$ may be provided for each locus. The estimation of $f(C|G_1,G_2,\chi_i)$ may be generated using two-dimensional density estimations and/or two-dimensional probability distribution functions.

The term $f(C|G_1,G_2,\chi_i)$ may be or include, and/or be computed using, one or more probability distribution functions provided according to the seventh aspect of the invention.

According to a seventh aspect of the invention we provide a method for generating one or more probability distribution functions relating to the detected level for a variable characteristic of DNA, the method including:

a) providing a control sample of DNA;
  b) analysing the control sample to establish the detected level for the at least one variable characteristic of DNA;
  c) repeating steps a) and b) for a plurality of control samples to form a data set of detected levels;
  d) defining a probability distribution function for at least a part of the data set of detected levels.

The method may be used to provide a probability distribution function for the detected level for control samples from heterozygous persons.

The method may be used to provide a probability distribution function for the detected level for control samples from homozygous persons.

Preferably the method is used to provide a probability distribution function for the detected level for control samples from heterozygous persons and to provide a probability distribution function for the detected level for control samples from homozygous persons. Preferably the performance of the method to provide the probability distribution function for the heterozygous persons is a separate performance to that used to provide the probability distribution function for the homozygous persons.

The detected level for the variable characteristic may be a peak height. The detected level may be a peak area. The detected level for the variable characteristic may be a peak weight. A peak weight may be defined as the molecular weight of the allele multiplied by the peak height or peak area for that allele.

The characteristic may be the allele identity or identities at a locus known to have variable short tandem repeat alleles.

The probability distribution function may be a 2-dimensional probability distributional function. The probability distribution function may be formed as a 2-dimensional probability distribution function or may be converted thereto, for instance from a one-dimensional probability distribution function or from a three-dimensional probability distribution function.

Steps a) and b) may be performed on control samples from one person, preferably a plurality of different persons and ideally at least four different persons.

Steps a) and b) may be performed on at least 20 control samples, preferably at least 100 control samples, more preferably at least 200 control samples and ideally on at least 500 control samples. These numbers of control samples may be the total number or the number for each different person from whom control samples are considered.

Steps a) and b) may be performed on one example of each control sample. Steps a) and b) may be performed on a plurality of examples of each control sample, for instance at least 20 examples of each control sample. These numbers of control samples may be the total number or the number for each different person from whom control samples are considered.

The person's who are the source of the control samples may be selected to be heterozygous with respect to the variable characteristic, particularly to generate a probability distribution function for heterozygotes.

The person's who are the source of the control samples may be selected to be homozygous with respect to the variable characteristic, particularly to generate a probability distribution function for homozygotes.

The method may be applied to one or more control samples which include different quantities of DNA. The quantities of DNA may be provided across a range of quantities, for instance at regular intervals across the range. The range may have a lower limit of 10 pg and more preferably 50 pg. The range may have an upper limit of 1000 pg and more preferably of 500 pg. The interval may be every 10 to 50 pg or potentially every 25 pg.

The analysis of the detected level for the variable characteristic is preferably provided in respect of more than one variable characteristic. The variable characteristic(s) are preferably the allele identity or allele identities present at a locus. Preferably the control samples are considered in respect of one or more loci, preferably at least 8 loci.

The probability distribution function, pdf, may be formed of one or more probability distribution functions. A probability distribution function may be provided for a group of control samples, with the control samples being divided into more than one group of control samples. The probability distribution function may be formed of four probability distribution functions, particularly in the context of the consideration of test samples from two different people.

The detected levels for the characteristic may be divided into one or more groups. One group may be those control samples whose detected level is at and/or above a threshold value. One group may be those control samples whose detected level is at and/or below a threshold value.

Where the control samples are from homozygous persons, the detected levels are preferably divided into two groups, most preferably relative to a threshold. The division of the detected levels into two groups may provide a 1-dimensional probability distribution function. It is preferred that the 1 dimensional pdf be converted to a 2-dimensional pdf.

The method used to convert a 1-dimensional pdf to a 2-dimensional pdf may include treating the pdf for a homozygous sample with height $h_1$ is being defined by the pdf for a heterozygous sample with heights $0.5h_1$ and $0.5h_2$.

Alternatively, the 1-dimensional pdf may be converted into a 2-dimensional pdf by mathematically rotating the distribution through an angle, particularly 90°. The method may include the use of a 1-dimensional pdf estimating by two components. One of the components may be a uniform distribution for the height interval. One of the components may be a probability distribution that takes positive values within that height interval range, for example an exponential distribution. The one-dimensional pdf may be defined by the formula, $$f_H(h) = \begin{cases} p_0 \times \frac{1}{t} & \text{if } h \in (0, t] \\ p_1 \times f_{H|H>t} & \text{if } h \in (t, \infty) \end{cases} \quad (3)$$

where $p_0$ is the proportion of heights in the range;

$p_1$ is the proportion of heights above the range;

t is the detection threshold, for instance 30 rfu's.

The surface of the distribution obtained by rotation may be normalised so that the volume under the surface is 1.

The calculation of a pdf value for homozygote peak height h for a likelihood ratio calculation may be given by:

$$(1/V) \times f_H. \quad (4)$$

where V is the volume under the surface obtained by rotation of the one-dimensional pdf.

One group may those control samples whose detected level is at and/or above a threshold value in respect of a first variable characteristic, such as a higher weight characteristic, and is at and/or above a threshold value in respect of a second variable characteristic, such as a lower weight characteristic. One group may be those control samples whose detected level is at and/or below a threshold value in respect of a first variable characteristic, such as a higher weight characteristic, and is at and/or below a threshold value in respect of a second variable characteristic, such as a lower weight characteristic. One group may those control samples whose detected level is at and/or above a threshold value in respect of a first variable characteristic, such as a higher weight characteristic, and is at and/or below a threshold value in respect of a second variable characteristic, such as a lower weight characteristic. One group may be those control samples whose detected level is at and/or below a threshold value in respect of a first variable characteristic, such as a higher weight characteristic, and is at and/or above a threshold value in respect of a second variable characteristic, such as a lower weight characteristic.

Where the control samples are from heterozygous persons, the detected levels may be divided into four groups, particularly where the test sample to be considered is from two sources.

The threshold may be a detection level at which detection of the characteristic relative to the detection of noise signals is not possible or is impaired. The threshold may be between 10 random fluorescence units and 70 rfu's, more preferably less than 60 rfu's, still more preferably 50 rfu's or less or even less than 40 rfu's.

The threshold may be different for different variable characteristics at a locus, but is preferably the same. The threshold may be different or the same for different loci.

Where the one group is those control samples whose detected level is at and/or above a threshold value in respect of a first variable characteristic, such as a higher weight characteristic, and is at and/or above a threshold value in respect of a second variable characteristic, such as a lower weight characteristic, the detected level for each variable may be the values contributing to the probability distribution function defined.

Where the one group is those control samples whose detected level is at and/or below a threshold value in respect of a first variable characteristic, such as a higher weight characteristic, and is at and/or below a threshold value in respect of a second variable characteristic, such as a lower weight characteristic, the detected level for the first characteristic and a value of zero for the second characteristic may be the values contributing to the probability distribution function.

Where the one group is those control samples whose detected level is at and/or above a threshold value in respect of a first variable characteristic, such as a higher weight characteristic, and is at and/or below a threshold value in respect of a second variable characteristic, such as a lower weight characteristic, the detected level for the second characteristic and a value of zero for the first characteristic may be the values contributing to the probability distribution function.

Where the one group is those control samples whose detected level is at and/or below a threshold value in respect of a first variable characteristic, such as a higher weight characteristic, and is at and/or above a threshold value in respect of a second variable characteristic, such as a lower weight characteristic, a value of zero for the first characteristic and a value of zero for the second characteristic may be the values contributing to the probability distribution function.

The probability distribution function, particularly for a heterozygous source, may be provided by four probability functions.

The probability distribution function may be, or more preferably include a probability distribution function, that function relating to, or being:

$$p_{1,1} \times \frac{1}{t^2}$$

where $p_{1,1}$ is the proportion of data where $h_1 < t$ and $h_2 < t$ where t is the detection threshold, particularly where the one group is those control samples whose detected level is at and/or above a threshold value in respect of a first variable characteristic, such as a higher weight characteristic, and is at and/or above a threshold value in respect of a second variable characteristic, such as a lower weight characteristic, the detected level for each variable may be the values contributing to the probability distribution function defined.

The probability distribution function may be, or more preferably include a probability distribution function, that function relating to, or being:

$$p_{1,2} \times g_{1,2}(h_1,h_2)$$

where $p_{1,2}$ is the proportion of points where $h_1 \geq t$ and $h_2 < t$, $g_{1,2}$ is a 2-dimensional probability density function for the region where $h_1 \geq t$ and $h_2 < t$, $h_1$ is the height of the low-molecular allele, $h_2$ is the height of the high-molecular allele, particularly where the one group is those control samples whose detected level is at and/or below a threshold value in respect of a first variable characteristic, such as a higher weight characteristic, and is at and/or below a threshold value in respect of a second variable characteristic, such as a lower weight characteristic, the detected level for the first characteristic and a value of zero for the second characteristic may be the values contributing to the probability distribution function. The probability distribution may be, or more preferably include a probability distribution function, that function relating to, or being:

$$g_{1,2}(h_1,h_2) = g_{1,2}(h_1|h_2)g_{1,2}(h_2)$$

where $g_{1,2}(h_1|h_2)$ is estimated from experimental data where $h_1 \geq t$ and $h_2 < t$, and:

$$g_{1,2}(h_2) = \frac{1}{t}.$$

The probability distribution function may be, or include, particularly for this group, an exponential distribution.

The probability distribution function may be, or more preferably include a probability distribution function, that function relating to, or being:

$$p_{2,1} \cdot g_{2,1}(h_1,h_2).$$

where $p_{2,1}$ is the proportion of pairs of heights in the region where $h_1 < t$ and $h_2 \geq t$, $g_{2,1}$ is a 2-dimensional probability density function for the region where $h_1 < t$ and $h_2 \geq t$, $h_1$ is the height of the low-molecular allele, $h_2$ is the height of the high-molecular allele particularly where the one group is those control samples whose detected level is at and/or above a threshold value in respect of a first variable characteristic, such as a higher weight characteristic, and is at and/or below a threshold value in respect of a second variable characteristic, such as a lower weight characteristic, the detected level for the second characteristic and a value of zero for the first characteristic may be the values contributing to the probability distribution function. The probability distribution may be, or more preferably include a probability distribution function, that function relating to, or being:

$$g_{2,1}(h_1,h_2) = g_{2,1}(h_2|h_1)g_{2,1}(h_1) \qquad (A.5)$$

where $g_{2,1}(h_2|h_1)$ is estimated from experimental data where $h_1 < t$ and $h_2 > t$ and:

$$g_{2,1}(h_1) = \frac{1}{t}. \qquad (A.6)$$

The probability distribution function may be, or include, particularly for this group, an exponential distribution.

The probability distribution function may be, or more preferably include a probability distribution function, that function relating to, or being:

$$p_{2,2} \times g_{2,2}(h_1,h_2)$$

where $p_{2,2}$ is the proportion of height pairs $(h_1, h_2)$ that fall in the region where $h_1 \geq t$ and $h_2 \geq t$, $g_{2,2}$ is a 2-dimensional probability density function for the region where $h_1 \geq t$ and $h_2 \geq t$, $h_1$ is the height of the low-molecular-weight allele, $h_2$ is the height of the high-molecular-weight allele, particularly where the one group is those control samples whose detected level is at and/or below a threshold value in respect of a first variable characteristic, such as a higher weight characteristic, and is at and/or above a threshold value in respect of a second variable characteristic, such as a lower weight characteristic, a value of zero for the first characteristic and a value of zero for the second characteristic may be the values contributing to the probability distribution function.

One or more of the probability distribution functions may be a uniform distribution. One or more of the distribution functions may be a triangular distribution. One or more of the distribution functions may be an exponential distribution.

The probability distribution function, particularly for a heterozygous source, may be defined as $$f(h_1, h_2) = \qquad (A.7)$$

$$\begin{cases} p_{1,1} \times \frac{1}{t^2} & \text{if } h_1 < t \, \& \, h_2 < t \\ p_{1,2} \times k_{1,2}(h1 - t | l_{12}) \times \frac{1}{t} & \text{if } h_1 \geq t \, \& \, h_2 < t \\ p_{2,1} \times k_{2,1}(h2 - t | l_{21}) \times \frac{1}{t} & \text{if } h_1 < t \, \& \, h_2 \geq t \\ p_{2,2} \times k_{2,2}\left(\frac{h_1 - t + h_2 - t}{2}, \log\left(\frac{h_1 - t}{h_2 - t}\right)\right) \times \\ \qquad \frac{1}{2}\left(\frac{1}{h_1 - t} + \frac{1}{h_2 - t}\right) & \text{if } h_1 \geq t \, \& \, h_2 \geq t \end{cases}$$

where, $k_{1,2}$ is an exponential probability density function, $k_{2,1}$ is an exponential probability density function, $l_{1,2}$ and $l_{2,1}$ are parameters of the exponential distribution, and preferably where:

$$k_{1,2}(x | l_{12}) = \frac{1}{l_{12}} \times \exp\left\{-\frac{x}{l_{12}}\right\}, \qquad (A.8)$$

is the pdf of an exponential distribution with parameter $l_{1,2}$, where x is a variable representing $h_{1-t}$, and preferably where:

$$k_{2,1}(x | l_{2,1}) = \frac{1}{l_{2,1}} \times \exp\left\{-\frac{x}{l_{2,1}}\right\}. \qquad (A.9)$$

and $k_{2,2}$ is preferably given by a mixture of two-dimensional normal distributions:

$$k_{2,2}(x, y) = \sum_i p_i \times n\left([x, y] | [\mu_{x,i}, \mu_{y,i}], \sum_i\right) \qquad (A.10)$$

where $p_i$ is the mixing proportion and n is a 2-dimensional probability density function of a normally distributed random variably, preferably where:

$$\sum_i = \begin{bmatrix} \sigma_{x,i}^2 & \rho\sigma_{x,i}\sigma_{y,i} \\ \rho\sigma_{x,i}\sigma_{y,i} & \sigma_{y,i}^2 \end{bmatrix} \qquad (A.11)$$

and preferably:

$$n\left([x, y] | [\mu_{x,i}, \mu_{y,i}], \sum_i\right) = \qquad (A.12)$$

$$\frac{1}{2\pi\sigma_{x,i}\sigma_{y,i}} \times \exp\left\{-\frac{1}{2}\left(\frac{(x - \mu_{x,i})^2}{\sigma_{x,i}^2} + \frac{(y - \mu_{y,i})^2}{\sigma_{y,i}^2}\right)\right\}.$$

where correlation coefficient $\rho = 0$.

Where the one group is those control samples whose detected level is at and/or above a threshold value in respect of a first variable characteristic, such as a higher weight characteristic, and is at and/or above a threshold value in respect of a second variable characteristic, such as a lower weight characteristic, the probability distribution function may be fitted to the detected levels observed for the control samples.

Where the one group is those control samples whose detected level is at and/or below a threshold value in respect of a first variable characteristic, such as a higher weight characteristic, and is at and/or below a threshold value in respect of a second variable characteristic, such as a lower weight characteristic, the probability distribution function may be provided by fitting a 2 dimensional planar distribution to the group and/or a distribution function whose shape represents a transition from values at the junction with the adjoining groups and/or whose shape provides a probability value of zero at zero value for detected level for both the first and second characteristic.

Where the one group is those control samples whose detected level is at and/or above a threshold value in respect of a first variable characteristic, such as a higher weight characteristic, and is at and/or below a threshold value in respect of a second variable characteristic, such as a lower weight characteristic, the probability distribution function may be provided by fitting a 2 dimensional planar distribution to the group and/or a distribution function whose shape represents a transition from values at the junction with the adjoining groups.

Where the one group is those control samples whose detected level is at and/or below a threshold value in respect of a first variable characteristic, such as a higher weight characteristic, and is at and/or above a threshold value in respect of a second variable characteristic, such as a lower weight characteristic, the probability distribution function may be provided by fitting a 2 dimensional planar distribution to the group and/or a distribution function whose shape represents a transition from values at the junction with the adjoining groups.

The probability distribution function, particularly for a heterozygous source, may be provided by estimating a two dimensional pdf for a pair of heights $h_1$ and $h_2$, for instance in the space defined by mean heights, m, and heterozygote imbalance, r. The method may include each pair of heights being transformed by $$(h_1, h_2) \mapsto \left(m = \frac{h_1 + h_2}{2}, r = \frac{h_1}{h_2}\right). \qquad (5)$$

Given a pdf $f_{M,R}$, a pdf in the space of pairs of heights may be obtained with the formula:

$$f_{H_1,H_2}(h_1, h_2) = \frac{1}{h_2^2}\left(\frac{h_1+h_2}{2}\right) \times f_{M,R}(m, r) \quad (6)$$

where the first factor is the Jacobian of the transformation, G. Casella & R. L. Berger (1990). Statistical Inference. Wadsworth & Brooks/Cole Advanced Books Software, Pacific Grove, Calif., USA, page 148 and the second factor can be estimated from experimental data. The estimation may be provided by obtaining the conditional distribution of heterozygous imbalance given mean height:

$$f_{H_1,H_2}(h_1, h_2) = \frac{1}{h_2^2}\left(\frac{h_1+h_2}{2}\right) \times f_{R|M}(r|m)f_M(m) \quad (7)$$

The method may use this approach, and particularly this function, to provide one pdf $f_{R|M}$ for all four regions, for example as shown in FIG. 2. The method may provide that there will be one marginal for each of the four regions, for instance marginal pdf's $f_M$ for each of the regions.

The method may provided that the conditional pdf $f_{R|M}$ can be obtained using data from region (1,2) and extrapolate to a pdf $f_{R|M}$ for all regions. The method may provide that a simulation is provided for the material which is missing in each of these three zones. The method may include a joint pdf $f_{ln(M),ln(R)}$ for variables ln(M) and ln(R) is obtained first. The method may include a conditional pdf $f_{R|M}$ being calculated from $f_{ln(M),ln(R)}$. The method may include correcting the biasing of pdf $f_{R|M}$ by the biased introduced by the threshold, for instance 30 rfu. The method may provide that the bias is removed by replacing each $f_{R|M}$ with a Log normal pdf and correcting in the space of parameters mean, μ, and variance, σ, of the Log normal pdf's.

The method may include estimating the two-dimensional pdf $f_{ln(M),ln(R)}$ for variables ln(M) and ln(R) using the EM-algorithm, where each Gaussian has zero correlation; A. Dempster, N. Laird, and D. Rubin (1977). "Maximum likelihood from incomplete data via the EM algorithm". Journal of the Royal Statistical Society, Series B, 39(1):1-38, 1977; G. Mclachlan, D. Peel (2000). Finite mixture models. John Wiley & Sons, Inc.

The method may include a conditional distribution of R given M being calculated from the estimated $f_{ln(M),ln(R)}$ using the formula:

$$f_{R|M}(r|m) = \frac{f_{M,R}(m,r)}{f_M(m)} \quad (8)$$

$$= \frac{\frac{1}{mr}f_{ln(M),ln(R)}(m,r)}{\frac{1}{m}f_{ln(M)}(m)}$$

$$= \frac{f_{ln(M),ln(R)}(m,r)}{r \times f_{ln(M)}(m)}.$$

The method may include the pdf $f_{ln(M)}$ being a mixture of one-dimensional Gaussian distribution with the same mixing proportions as $f_{ln(M),ln(R)}$ and mean and variances given by the corresponding mean and variances. The method may include several conditional pdf's being computed. The method may include providing Lognormal distributions to simulate the conditional pdf for R given M. The method may include the pdf of the lognormal distribution being given by:

$$f_R(r) = \frac{1}{r \times \sigma\sqrt{2\pi}} \exp\frac{-(ln(r)-\mu)^2}{2\sigma^2}. \quad (9)$$

The method may include correcting the bias in the space of parameters (μ,σ) of the Log normal pfd's. The method may include a number of iterations of the values for μ and/or σ. In particular, the method may included two or more iterations of the value for μ and the estimation procedure for σ.

The pdf for a value of M may be obtained by extrapolate the trend defined by two or more values of M to lower values of M. One or more, preferably several, polynomials may be fitted to values of σ in the regions of the higher M values, for instance from 80 to 200 rfu. The trend may be a line, spline or straight line.

The method may include obtaining a family of Lognormal distributions of defined by:

$$f_{R|M}(r|m) = \frac{1}{r \times \sigma(m)\sqrt{2\pi}} \exp\frac{-(ln(r)-\mu)^2}{2[\sigma(m)]^2} \quad (10)$$

The method may include defining another component in the proposed two-dimensional distribution for peak height as pdf's for mean in each of the four regions.

For region (0,0) a uniform distribution may be defined. The pdf for mean height may be:

$$f_M(m) = p_{(0,0)} \times \frac{1}{t} \quad (11)$$

where $p_{(0,0)}$ is the proportion of pair of heights that fall in region (0,0) and t is the threshold and can be 30 rfu's or can be replaced by another rfu value as desired.

For region (1,0), the method may include obtaining a distribution for peak height ($h_1,h_2$) in this region. The method may then calculate a distribution for mean height. The method may include extracting a pdf for mean height and used the extrapolated distribution and transformed back to the space of ($h_1,h_2$). The method may include defining a joint distribution in this region by assuming that the variables $h_1$ and $h_2$ are independent. A uniform distribution may be assumed for ($h_1,h_2$). A pdf for region (1,0) may be given by:

$$f_{H_1,H_2}(h_1, h_2) = p_{(1,0)} \times \frac{1}{30} \times \frac{1}{\lambda_{(1,0)}} \exp\left\{-\frac{h_1-30}{\lambda_{(1,0)}}\right\} \quad (12)$$

where $p_{(0,0)}$ is the proportion of pair of heights that fall in region (0,0) and 30 can be replaced by another rfu value as desired.

The method may include obtaining a pdf for mean height M by first using the transformation:

$$(h_1, h_2) \mapsto \left(m = \frac{h_1+h_2}{2}, n = \frac{h_1-h_2}{2}\right). \quad (13)$$

and then use the Jacobian of the transformation to obtain a two-dimensional pdf for (M,N). The method may include obtaining the marginal pdf for m through integration. The two-dimensional pdf for (M,N) may be given by:

$$f_{M,N}(m,n) = 2 \times f_{H_1,H_2}(h_1, h_2). \tag{14}$$

The two-dimensional pdf for (M,N) may be given by:

$$f_{M,N}(m,n) = p_{(1,0)} \times \frac{1}{15} \times \frac{1}{\lambda_{(1,0)}} \exp\left\{-\frac{m+n-30}{\lambda_{(1,0)}}\right\}. \tag{15}$$

The method may provide that the pdf for M is given by:

$$f_M(m) = p_{(1,0)} \times \frac{1}{15} \times \left[1 - \exp\left\{-\frac{2m-30}{\lambda_{(1,0)}}\right\}\right] \tag{16}$$

where 15 is the lower quantity proportion and can be replaced by another value and 30 is the higher peal quantity proportion and can be replaced by another value. The method may include that the pdf for M is given by:

$$f_M(m) = p_{(1,0)} \times \frac{1}{15} \times \left[\exp\left\{-\frac{2(m-30)}{\lambda_{(1,0)}}\right\} - \exp\left\{-\frac{2m-30}{\lambda_{(1,0)}}\right\}\right] \tag{17}$$

where 15 is the lower quantity proportion and can be replaced by another value and 30 is the higher peal quantity proportion and can be replaced by another value.

The method may use the same methodology or a methodology as described above for region (1,0) to obtain a pdf for mean height in region (0,2). The method may provide that the pdf for $(H_1, H_2)$ is given by:

$$f_{H_1,H_2}(h_1, h_2) = p_{(0,2)} \times \frac{1}{30} \times \frac{1}{\lambda_{(0,2)}} \exp\left\{-\frac{h_2 - 30}{\lambda_{(0,2)}}\right\}. \tag{18}$$

where $p_{(0,2)}$ is the proportion of height pairs that fall in region (0,2) and 30 can be replaced by another rfu value as desired and constant $\lambda_{(0,2)}$ is the parameter of an exponential pdf estimated from values of $h_2$.

The method for calculating a marginal for M in region (0,2) may be the same as, or provided according to the possibilities for, region (1,0). The pdf may be given by:

$$f_M(m) = p_{(0,2)} \times \frac{1}{15} \times \left[1 - \exp\left\{-\frac{2m-30}{\lambda_{(0,2)}}\right\}\right] \tag{19}$$

if m ∈ [15,30), and $$f_M(m) = p_{(0,2)} \times \frac{1}{15} \times \left[\exp\left\{-\frac{2(m-30)}{\lambda_{(0,2)}}\right\} - \exp\left\{-\frac{2m-30}{\lambda_{(0,2)}}\right\}\right] \tag{20}$$

if m≧30, where 15 is the lower quantity proportion and can be replaced by another value and 30 is the higher peal quantity proportion and can be replaced by another value.

The method may provide that the pdf $f_M$ for region (1,2) can be obtained from the two-dimensional pdf estimated for (ln (M),ln(R)). The result may be a mixture of one-dimensional Gaussians. The method may provide that the pdf for M in region (1,2) is given by:

$$f_M(m) = p_{(1,2)} \times \sum_{i=1}^{4} p_i \times f(m | \mu_i, \sigma_i) \tag{21}$$

where $p_{(1,2)}$ is the proportion of height pairs that fall in region (1,2) and $p_i$ is the mixing proportion of the Gaussian components and $f(m|\mu_i,\sigma_i)$ are the Gaussian pdf's.

The method may provide for the generation of a probability distribution function for a given locus. The method may provide for the generation of a probability distribution function for each of a plurality of loci. The method may provide for the generation of a probability distribution function for a combination of loci. The combination of loci may correspond to those analysed using a PCR amplification multiplex, such as SGMplus. A plurality of different probability distribution functions may be provided for different combinations of loci. Probability distribution functions may be generated for a number of combinations corresponding to the combinations of loci analysed in different PCR amplification multiplexes.

The method may provide for the generation of a probability distribution function for a given DNA quantity. The method may provide for the generation of a probability distribution function for each of a number of different DNA quantities. Probability distribution functions may be provided for different values of DNA quantity provided across a range of DNA quantities. The different values may be evenly spaced throughout the range.

The method may provide for the generation of a probability distribution function for a given DNA quantity in respect of one locus and/or for a combination of loci. The method may provide for the generation of a probability distribution function for each of a number of different DNA quantities for one locus and/or for a combination of loci.

The one or more generated probability distribution functions may be stored for later use, for instance in a computer implemented database. The one or more generated probability distribution functions may be stored in an electronic or solid state memory. The method may include providing the one or more probability distribution functions in a computer implemented database and/or electronic memory device and/or solid state memory device. The one or more probability distribution functions may be stored at a location remote from the location of use and/or location of the device using the one or more probability distribution functions, for instance by storing on a remote access unit, for instance accessible via the Internet.

The later use of one or more probability distribution functions may in a method according to the first aspect of the invention or its features or possibilities. The memory may be provided as a part of, in permanent connection with or in temporary connection with a device according to the second aspect of the invention or any of the possibilities provided therefore.

The one or more stored probability distribution functions may be used one or more times in subsequent method steps, such as those of the first aspect of the invention.

Any of the proceeding aspects of the invention may include the following features, options or possibilities or those set out elsewhere in this document.

The method may be a computer implemented method.

The method may involve the display of information to a user, for instance in electronic form or hardcopy form.

The test sample, may be a sample from an unknown source. The test sample may be a sample from a known source, particularly a known person. The test sample may be analysed to establish the identities present in respect of one or more variable parts of the DNA of the test sample. The one or more variable parts may be the allele or alleles present at a locus. The analysis may establish the one or more variable parts present at one or more loci.

The test sample may be contributed to by a single source. The test sample may be contributed to by an unknown number of sources. The test sample may be contributed to by two or more sources. One or more of the two or more sources may be known, for instance the victim of the crime.

The test sample may be considered as evidence, for instance in civil or criminal legal proceedings. The evidence may be as to the relative likelihoods, a likelihood ratio, of one hypothesis to another hypothesis. In particular, this may be a hypothesis advanced by the prosecution in the legal proceedings and another hypothesis advanced by the defence in the legal proceedings.

The test sample may be considered in an intelligence gathering method, for instance to provide information to further investigative processes, such as evidence gathering. The test sample may be compared with one or more previous samples or the stored analysis results therefore. The test sample may be compared to establish a list of stored analysis results which are the most likely matches therewith.

The test sample and/or control samples may be analysed to determine the peak height or heights present for one or more peaks indicative of one or more identities. The test sample and/or control samples may be analysed to determine the peak area or areas present for one or more peaks indicative of one or more identities. The test sample and/or control samples may be analysed to determine the peak weight or weights present for one or more peaks indicative of one or more identities. The test sample and/or control samples may be analysed to determine a level indicator for one or more identities.

BRIEF DESCRIPTION OF THE DRAWINGS

Various embodiments of the invention will now be described, by way of example only, and with reference to the accompanying drawings in which:

FIG. 7b is an illustration of the fitting of one distribution type to the data below the detection threshold of FIG. 7a;

FIG. 7c is an illustration of the fitting of an alternative distribution type to the data below the detection threshold of FIG. 7a;

DETAILED DESCRIPTION OF THE PREFERRED EMBODIMENT(S)

Figure 1:
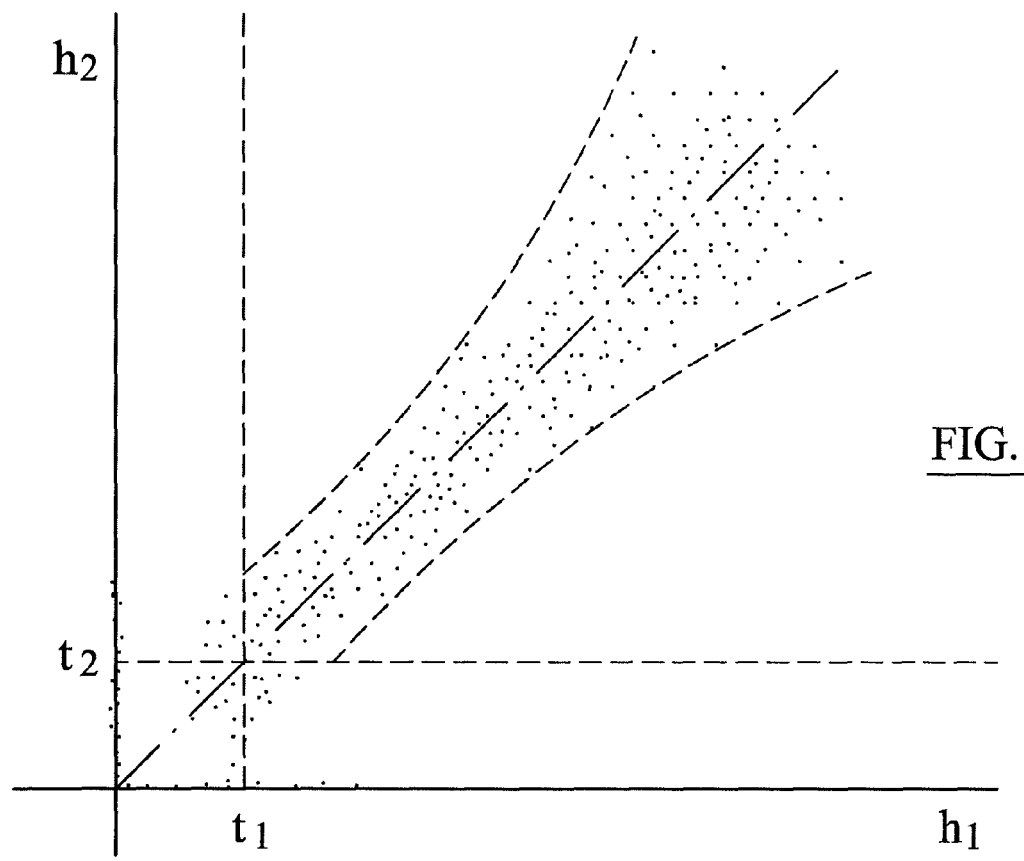
FIG. 1 is a plot of the peak height for the low molecular weight allele against peak height for the high molecular weight allele for a series of control samples.

The present invention is concerned with improving the interpretation of DNA analysis. Basically, such analysis involves taking a sample of DNA and analysing the variations present at a number of loci. The identities of the variations give rise to a profile which is then interpreted. The extent of interpretation required can be extensive and/or introduce uncertainties. This is particularly so where the DNA sample contains DNA from more than one person, a mixture.

There is often a need to consider various hypotheses for the identities of the persons responsible for the DNA and evaluate the likelihood of those hypotheses, evidential uses.

There is often a need to consider the analysis genotype against a database of genotypes, so as to establish a list of stored genotypes that are likely matches with the analysis genotype, intelligence uses.

The present invention provides a mathematical specification of a model for computing likelihood ratios (LRs) that uses peak heights taken from such DNA analysis.

The approach of the present invention draws on an estimation of a two-dimensional, 2D, probability density function, pdf, which is estimated from the heights, or areas, of peaks observed after the analysis of control samples. Such pdf's may be generated from heterozygous donors and separately from homozygous donors.

The invention goes on to use the approach to calculate the probability of dropout and achieve other benefits.

As a first part of the explanation, exemplary methods for generating the pdf's are discussed.

Generating a 2D Probability Distribution Function for Heterozygous Donors—Method One A key part of the present invention is the generation and then use of a 2D probability distribution function, pdf's, relating to peak heights. This is obtained through the analysis of a large number of control samples.

The analyses of the control samples used to support the present approach needs to consider the presence of a variety of levels of DNA within the control samples because those various levels, and others, are encountered in unknown source samples of interest. When an unknown source sample is collected for DNA analysis, there is an aim to collect a given amount of DNA. However, the amount actually present in the unknown source sample varies around that amount because of a variety of factors.

To account for this, control pre-samples from a number of heterozygous donors were obtained and then a variety of control samples with different DNA amounts in them were generated from these pre-control samples. The control samples were then analysed to establish the alleles present and the peak heights therefore. This control sample investigation process was repeated for each locus of interest in the DNA analysis or comparison process to be improved upon by the invention. Thus different loci will need to be considered for different analysis approaches and/or for databases which store information on different loci.

Separate pdf's are beneficially generated for heterozygous and homozygous situations.

As an example of the control sample investigation process, four heterozygous donors may be used. Control samples having different amounts of DNA present are then generated over the range 50 pg to 500 pg in 25 pg steps. 200 repeats of the pre-control samples were provided from each donor and used to form the control sample sets.

The results of the analysis of these control samples can be considered by plotting:
- on one axis the amount of DNA detected in the analysis, expressed as the peak height for the lower molecular weight allele at the locus which is observed, $h_1$; and
- on the other axis the amount of DNA detected in the analysis, expressed as the peak height for the higher molecular weight allele at the locus which is observed, $h_2$.

A set of results using this approach is shown schematically in FIG. 1. As a general observation, the $h_1$ and $h_2$ levels are distributed around an equivalent level, (the 45° dot-dash-dot line) with the peak height increasing as the amount of DNA in the sample increases.

When considering the peak heights, the detection of a height relative to the noise signal in the analysis becomes difficult below a threshold level. As a result, it is normal to discount peak heights below a predetermined threshold, t, as being unreliable to consider further. As we known the control samples are from people who are heterozygous for the locus in question, we know that these non-observed peaks correspond to dropout of the allele from the analysis results. The allele is present in the DNA, but not present in the analysis results for the DNA.

The use of these thresholds, t, is provided for in the FIG. 1 plot. When the value for one of the $h_1$ or $h_2$ values is below the threshold, then the point is plotted on the relevant axis as a zero value. When both are below the threshold, the point is plotted at the junction of the axes; a zero value for both.

Figure 2:
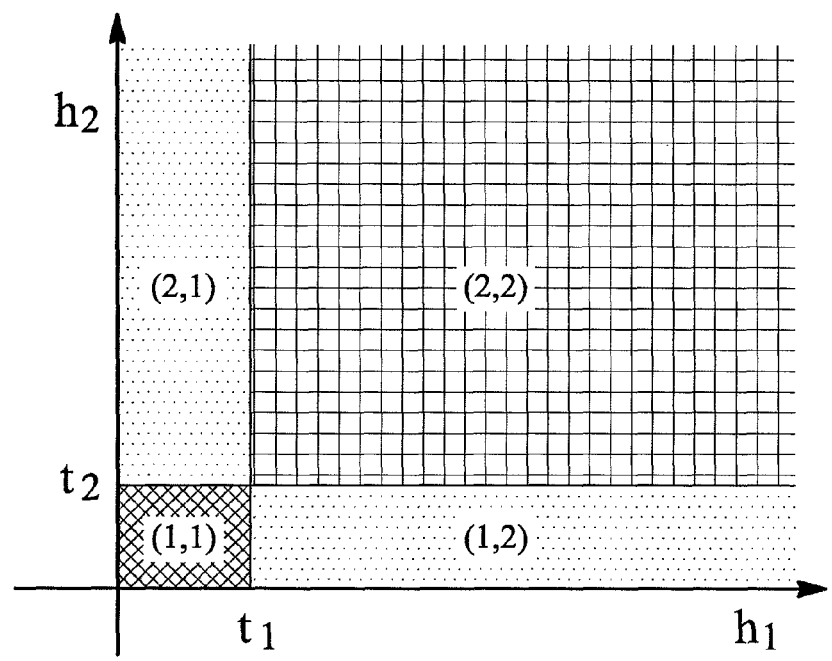
FIG. 2 is a graphical representation of the sample space of peak heights based upon the data of FIG. 1.

The distribution of FIG. 1 can be considered further in the schematic form illustrated in FIG. 2. This divides the results of the analysis of the control samples into four blocks which are defined by the axes and the threshold values, $t_1$ and $t_2$. The region (1,1) defines that block in which neither $h_1$ or $h_2$ are above the threshold t. The region (1,2) defines that block in which the higher molecular weight allele, $h_2$, is observed below the threshold t, but the lower molecular weight allele, $h_1$, is above the threshold, t. The region (2,1) defines that block in which the lower molecular weight allele, $h_1$, is observed below the threshold t, but the higher molecular weight allele, $h_2$, is above the threshold, t. The region (2,2) defines that block in which both the alleles, $h_1$ and $h_2$, are both above their respective thresholds $t_1$ and $t_2$.

In further considerations, both $t_1$ and $t_2$ have the same value and are represented as t, but different values could be used for the lower and higher weight alleles and/or between loci. The threshold could be 50 random fluorescence units, rfu's, or as low as 20 rfu's.

The 2D pdf's for peak heights, $f_{het}(h_1,h_2)$, where that function is a probability density function of heterozygous alleles with height values $h_1$ and $h_2$, can be defined piece-wise according to the four different regions identified above; $p_{1,1}$ being for region (1,1); $p_{1,2}$ for region (1,2); $p_{2,1}$ for region (2,1); and $p_{2,2}$ for region (2,2).

This approach gives the following definitions for the four regions of FIG. 2.

$$f_{het}(h_1, h_2) = \begin{cases} p_{1,1} \times \frac{1}{t^2} & \text{if } h_1 < t \text{ \& } h_2 < t \\ p_{1,2} \times g_{1,2}(h_1, h_2) & \text{if } h_1 > t \text{ \& } h_2 < t \\ p_{2,1} \times g_{2,1}(h_1, h_2) & \text{if } h_1 < t \text{ \& } h_2 > t \\ p_{2,2} \times g_{2,2}(h_1, h_2) & \text{if } h_1 > t \text{ \& } h_2 > t \end{cases} \quad (A.1)$$

The form of these definitions are now considered further:
Definition of $g_{1,2}(h_1,h_2)$
This is the joint distribution of $h_1$ and $h_2$ in region (1,2) of FIG. 2. The definition of $g_{1,2}(h_1,h_2)$ is provided through factorising the distribution as follows:

$$g_{1,2}(h_1,h_2) = g_{1,2}(h_1|h_2) g_{1,2}(h_2) \quad (A.2)$$

where $g_{1,2}(h_1|h_2)$ is estimated from experimental data where $h_1 > t$ and $h_2 < t$, and:

$$g_{1,2}(h_2) = \frac{1}{t}. \quad (A.3)$$

The reasoning behind this definition of $g_{1,2}$ follows from the calculation:

$$Pr(h_2 < t) = \int_0^t p_{1,2} g_{1,2}(h_2) \, dh_2 = p_{1,2} \int_0^t \frac{1}{t} \, dh_1 = p_{1,2} \frac{t}{t} = p_{1,2}. \quad (A.4)$$

The interpretation is that we only know that the peak height $h_2$ is below the threshold, t, and so they have equal probability in the interval (0,t).
Definition of $g_{2,1}(h_1,h_2)$
This is the joint probability of $h_1$ and $h_2$ in region (2,1) and follows a matching form to the previous definition. Hence, it is provided through factorising the distribution in a similar manner and as follows:

$$g_{2,1}(h_1,h_2) = g_{2,1}(h_2|h_1) g_{2,1}(h_1) \quad (A.5)$$

where $g_{2,1}(h_2|h_1)$ is estimated from experimental data where $h_1 < t$ and $h_2 > t$ and:

$$g_{2,1}(h_1) = \frac{1}{t}. \quad (A.6)$$

Definition of $g_{2,2}(h_1,h_2)$

This is the joint probability of $h_1$ and $h_2$ in region (2,2), this is provided by an estimate of a 2D pdf from experimental data where $h_1 > t$ and $h_2 > t$.

For the three regions and their distributions, the following distributions are presently estimated as applying:

$g_{1,2}(h_1,h_2)$—as a preliminary estimation we use an exponential distribution.

$g_{2,1}(h_1,h_2)$—as a preliminary estimation we use an exponential distribution.

$g_{2,2}(h_1,h_2)$—use a transformation of the data and then a 2D estimation.

The overall result of these definitions is that the 2D pdf for peak heights, $f_{het}(h_1,h_2)$, is given by:

$$f_{het}(h_1, h_2) = \begin{cases} p_{1,1} \times \frac{1}{t^2} & \text{if } h_1 < t \text{ \& } h_2 < t \\ p_{1,2} \times k_{1,2}(h1-t \mid l_{12}) \times \frac{1}{t} & \text{if } h_1 \geq t \text{ \& } h_2 < t \\ p_{2,1} \times k_{2,1}(h2-t \mid l_{21}) \times \frac{1}{t} & \text{if } h_1 < t \text{ \& } h_2 \geq t \\ p_{2,2} \times k_{2,2}\left(\frac{h_1-t+h_2-t}{2}, \log\left(\frac{h_1-t}{h_2-t}\right)\right) \times \frac{1}{2}\left(\frac{1}{h_1-t}+\frac{1}{h_2-t}\right) & \text{if } h_1 \geq t \text{ \& } h_2 \geq t \end{cases} \quad (A.7)$$

where, $k_{1,2}$; $k_{2,1}$; $l_{12}$; $l_{21}$; are described above, and where:

$$k_{1,2}(x \mid l_{12}) = \frac{1}{l_{12}} \times \exp\left\{-\frac{x}{l_{12}}\right\}, \quad (A.8)$$

is the pdf of an exponential distribution with parameter $l_{1,2}$, where x is the mixing proportion and:

$$k_{2,1}(x \mid l_{2,1}) = \frac{1}{l_{2,1}} \times \exp\left\{-\frac{x}{l_{2,1}}\right\}. \quad (A.9)$$

and $k_{2,2}$ is described above and the function $k_{2,2}$ is given by a mixture of two-dimensional normal distributions:

$$k_{2,2}(x, y) = \sum_i p_i \times n\left([x, y] \mid [\mu_{x,i}, \mu_{y,i}], \sum_i\right) \quad (A.10)$$

where y and n are described above, where:

$$\sum_i = \begin{bmatrix} \sigma_{x,i}^2 & \rho\sigma_{x,i}\sigma_{y,i} \\ \rho\sigma_{x,i}\sigma_{y,i} & \sigma_{y,i}^2 \end{bmatrix} \quad (A.11)$$

and:

$$n\left([x, y] \mid [\mu_{x,i}, \mu_{y,i}], \sum_i\right) = \quad (A.12)$$
$$\frac{1}{2\pi\sigma_{x,i}\sigma_{y,i}} \times \exp\left\{-\frac{1}{2}\left(\frac{(x-\mu_{x,i})^2}{\sigma_{x,i}^2}+\frac{(y-\mu_{y,i})^2}{\sigma_{y,i}^2}\right)\right\}.$$

where $\rho=0$.

Once determined, the 2D pdf for peak heights, $f_{het}(h_1,h_2)$, can be stored and made use of in a large number of subsequent considerations of likelihood ratios. As previously mentioned, such pdf's may be generated for each locus under consideration or potential consideration. In some cases, it may be necessary to determine a particular 2D pdf for peak heights, $f_{het}(h_1,h_2)$, for a particular situation, as part of the analysis process Generating a 2D Probability Distribution Function for Homozygous Donors—Method One In the previous section, an illustrative method for estimate a 2D pdf for the case where the source is heterozygote was provided. In this section we deal with the situation where the source is homozygote.

In this case, the probability distribution function, pdf, starts out as a 1D plot. There is only a value for $h_1$ as only one peak is observed. Thus above the threshold, t, this has a value and below it is represented at the zero value.

To enable compatibility between situations where the likelihood is being considered in 2D (based on the pdf's developed in the section above and the likelihood evaluation discussed in sections which follow below) the pdf for the homozygous situation also has to be defined in 2D. Otherwise, the likelihoods in the 2D heterozygous approach will be inherently less likely than in a 1D homozygous approach.

A number of methods for converting 1D pdf's to 2D pdf's exist and can be used.

The basis for this method is the observation that a homozygous sample with height $h_1$ is similar to observing a heterozygous sample with approximate heights $0.5h_1$ and $0.5h_1$.

Generating a 2D Probability Distribution Function for Homozygous Donors—Method Two—Approach a It is also possible to convert the 1D pdf into a 2D pdf by mathematically rotating the distribution through say 90°. The result is a pdf in 2D which can be used in the manner described below for homozygous donors and as an alternative to method 1 for homozygous donors.

Figure 3:
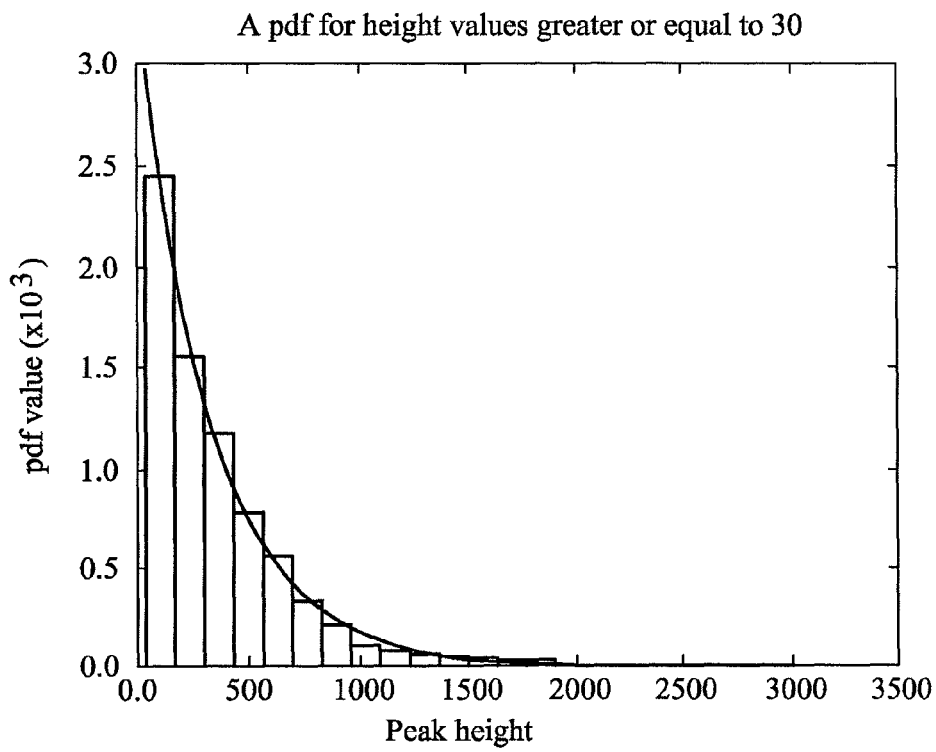
FIG. 3 is a statistical histogram of peak heights according to an exponential distribution.

The estimation of a one-dimensional pdf has two components. A uniform distribution for the interval, for instance height values in the range 0 to 30 and a probability distribution that takes positive values within that range, for example the exponential distribution of FIG. 3. FIG. 3 shows a statistical histogram of the peak heights. The plot line represents an exponential pdf estimated from the data as an example.

Figure 4:
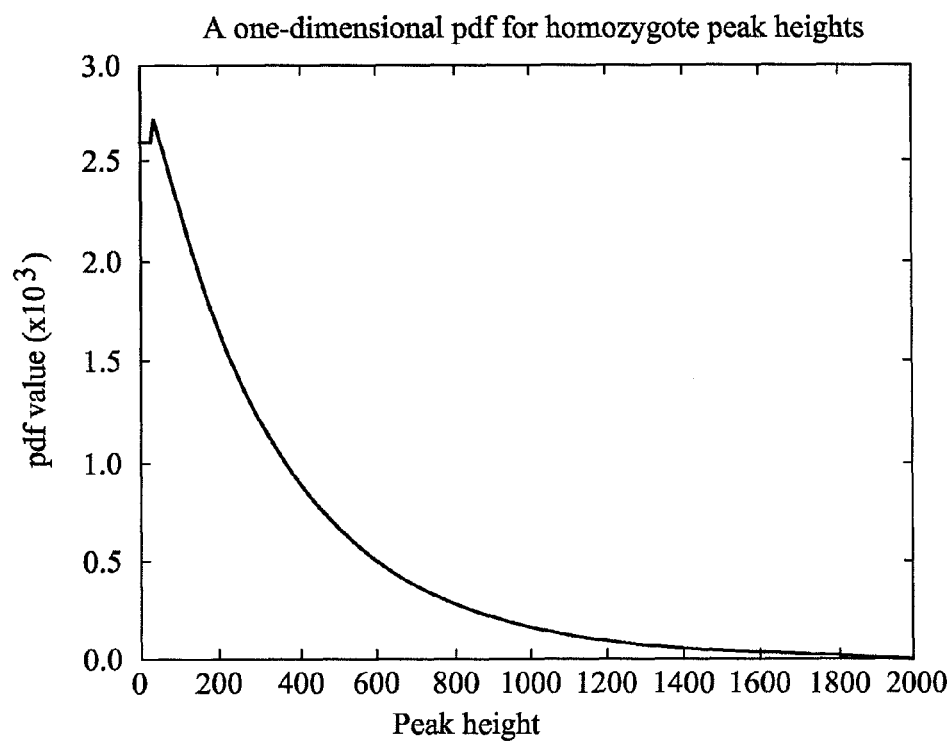
FIG. 4 is a probability distribution function for an example.

The one-dimensional pdf is given by the formula, $$f_H(h) = \begin{cases} p_0 \times \frac{1}{30} & \text{if } h \in (0, 30] \\ p_1 \times f_{H|H>30} & \text{if } h \in (30, \infty) \end{cases} \quad (22)$$

where $p_0$ is the proportion of heights in (0, 30];

$p_1$ is the proportion of heights in (30, ∞);

For example if $f_{H|H>30}$ is a exponential pdf, then $$f_H(h) = \begin{cases} p_0 \times \dfrac{1}{30} & \text{if } h \in (0, 30] \\ p_1 \times \dfrac{1}{\lambda}\exp\left\{-\dfrac{h-30}{\lambda}\right\} & \text{if } h \in (30, \infty) \end{cases} \quad (23)$$

where $\lambda$ is the estimated parameter for the exponential distribution using known methods of estimation, e.g. maximum likelihood estimation methods ready available in statistical packages. The overall pdf of an example for case when $f_{H|H>30}$ is an exponential distribution is plotted in FIG. 4.

Figure 5:
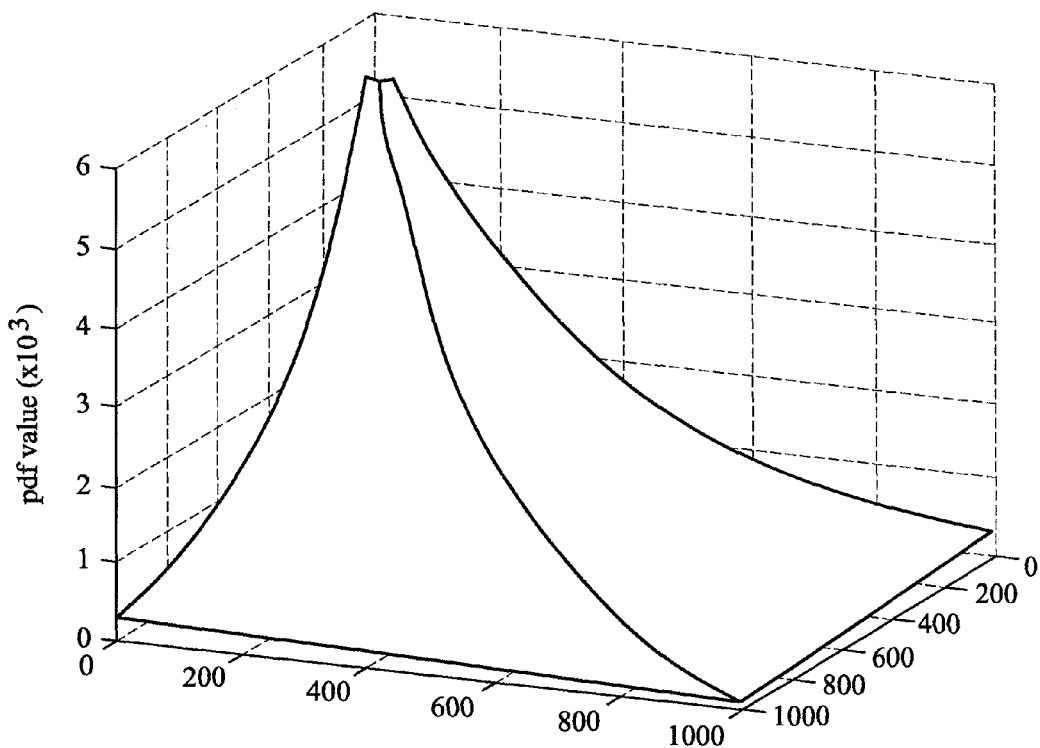
FIG. 5 is a two-dimensional pdf obtained from the example of FIG. 4.

The idea is to rotate the one-dimensional pdf above to take non-zero values in $R^+ \times R^+$. The surface obtained in this manner needs to be normalised so that the volume under the surface is one. FIG. 5 shows a two-dimensional pdf obtained from the example using an exponential distribution.

The calculation of a pdf value for homozygote peak height h for a likelihood ratio calculation is given by $$(1/V) \times f_H. \quad (24)$$

where V is the volume under the surface obtained by rotation of the one-dimensional pdf.

Generating a 2D Probability Distribution Function for Homozygous Donors—Method Two—Approach b That part of the distribution which relates to data left-censored by the rfu threshold, t, is discussed in approach a, with approach b offering an alternative.

In this approach, a family of distributions is chosen, $f(h|\theta)$, where $\theta$ represents the parameters determining the distributions and the parameters encoded in $\theta$ can be either one-dimensional or multi-dimensional. The type of distribution chosen can be one of numerous possibilities, such as Exponential, Weibull, Gamma or other distributions with positive support H. For example an Exponential distribution might be chosen where, thus providing:

$f(h|\theta) = \theta e^{-\theta h}$ where the $\theta$ can have different values, for instance 0.1, 0.11 etc to provide the family.

The Likelihood of the censored data can then be established by the function:

$$L(\theta | \{h_i: i=1,2,\ldots,n\}) = n_1 \times F(t|\theta) \times \prod_{i=1}^{m} f(h_i|\theta),$$
where there are $n_1$ heights recorded as zero due to left-censoring, and F is the cumulative probability distribution and f is the probability density function of the Exponential distribution and t is the detection threshold.

The family member for $\theta$ which gives the maximum value of the likelihood is chosen, that is, the maximum likelihood estimate (MLE) for $\theta$.

Generating a 2D Probability Distribution Function for Heterozygous Donors—Method Two—Approach a An alternative method for establishing a 2D pdf in the context of heterozygous donors is now described, starting with an explanation in using a 1D analogy, followed by an expansion of the approach to detail its working in 2D.

Figure 6:
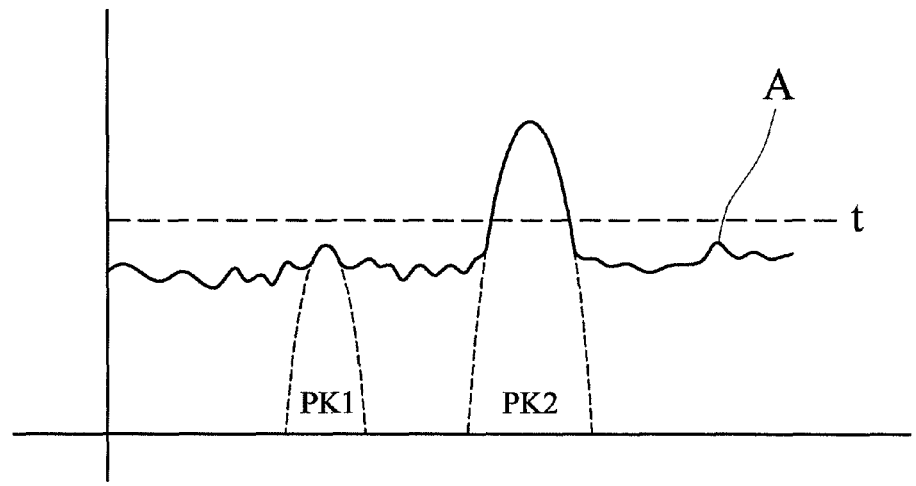
FIG. 6 is an illustration of the peak heights in a crime profile relative to a threshold.

In the consideration of heterozygous analysis results for the control samples, the two alleles may result in peaks of different heights. As previously described, there is a chance that one or both peaks may be below a threshold level, t, at which the peak can safely be identified or even identified at all. FIG. 6 illustrates a full analysis signal, A, and includes a representation of the two peaks, PK1 and PK2, which are actually present. In the case of PK2, sufficient signal is detected to discern and call that peak as "observed". However, in the case of peak PK1, the signal is so close to and mixed in with the noise signal that no peak can be discerned. This is the natural cut off at 20 to 30 rfu's mentioned above. A 50 rfu cut off is often applied to exclude peaks which may be discernable, but which cannot be absolutely distinguished from noise.

Figure 7A:
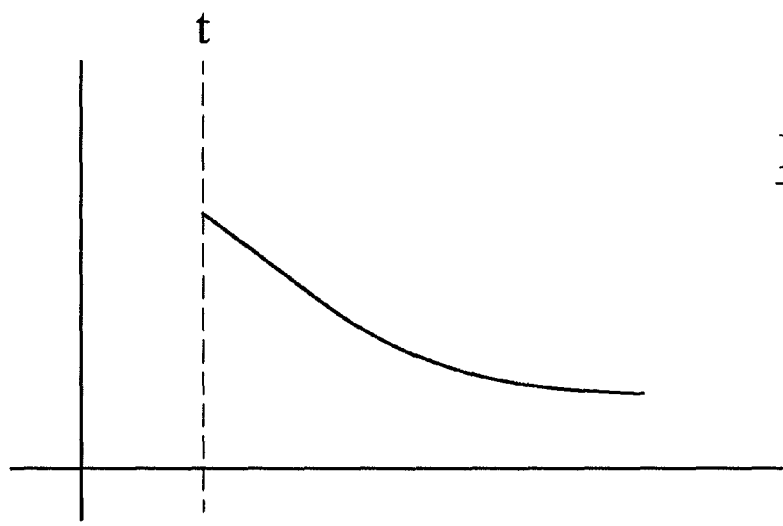
FIG. 7a is an illustration of a frequency distribution for allele peak height, including a detection threshold.

The result is that a distribution of data above the threshold, t, is established, but that the form of the distribution below the threshold, t, is not know. The position of the frequency distribution of FIG. 7a applies.

Figure 7B:
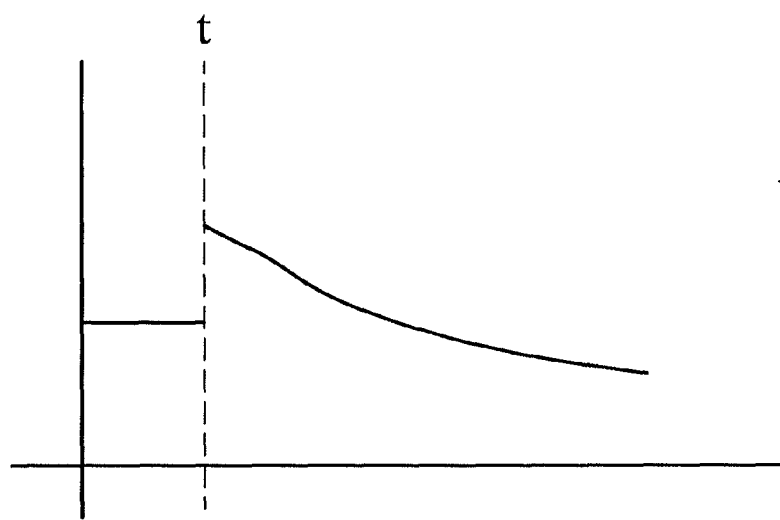
Figure 7C:
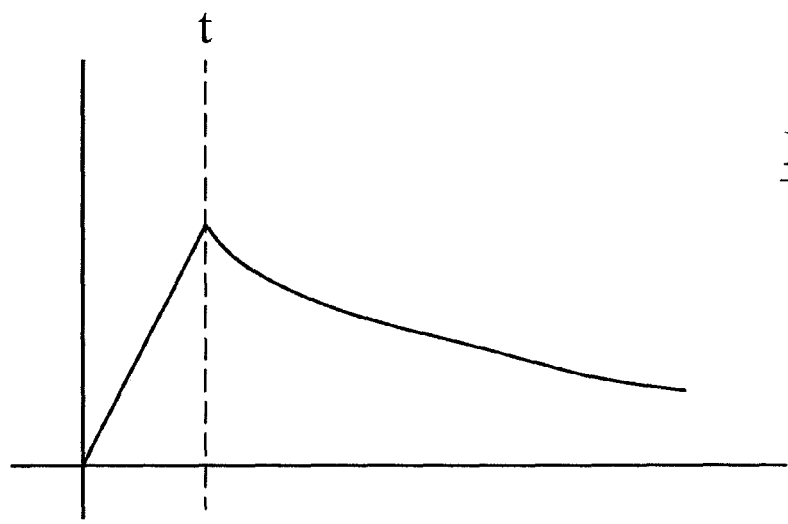

In the case of method 1 above, a uniform frequency for the distribution is applied to the unknown section below the threshold, see FIG. 7b.

In this alternative approach, a non-uniform distribution is applied to the region below the threshold, t. In the illustrated example of FIG. 4c, a triangular distribution is employed. Other distribution shapes can be applied to this region.

This approach can now be extending to the four regions describe in the context of FIG. 2 and hence into 2D.

The region (2,2) has a distribution which is fully known from the analysis results for the control samples. For the region (1,1) it is possible to use a 2D plane or other distribution shape which represents a transition from the region (2,2) distribution at $h_1=t$, $h_2=t$ down to zero at the junction of the axes and which also provides a transition from the values of region (1,2) along junction $h_1=t$, $h_2=0$ to t and from the values of region (2,1) along the junction $h_2=t$, $h_1=0$ to t. The regions (1,2) and (2,1) themselves can be further distributions representing a combination of the distribution applied in region (2,2) and that applied in region (1,1).

Generating a 2D Probability Distribution Function for Heterozygous Donors—Method Two—Approach b As described above, a profile from a heterozygous donor in a locus typically consists of two peaks. However if a profile is obtained from small amounts of DNA, it may contain either one peak or no peaks in the observed result. This is because a peak cannot be detected if is low and close to the baseline. In this example we use 30 rfu as the minimum detection limit, but other detection limits can be applied to the observed results.

The support of two-dimensional pdf is $R^+_\upsilon\{0\} \times R^+_\upsilon\{0\}$. The pair of heights $(h_1, h_2)$ are in effect censored by the threshold of t, for instance 30 rfu, that divides the support in four regions, see FIG. 2. The peak height $h_1$ of the low molecular weight allele is plotted in the x-axis and the peak height $h_2$ of the high molecular weight allele is plotted in the y-axis. In region (0,0) both peaks are below t, for instance 30 rfu; in region (1,0) $h_1$ is greater than or equal to t, for instance 30 rfu, whilst $h_2$ is less than t, for instance 30 rfu; in region (0,2) is the opposite case; and in region (1,2) both peak are greater than or equal to t, for instance 30 rfu.

The estimation of a two dimensional pdf is done in the space defined by mean heights, m, and heterozygote imbalance, r. Each pair of heights are transformed by $$(h_1, h_2) \mapsto \left(m = \frac{h_1 + h_2}{2}, r = \frac{h_1}{h_2}\right). \quad (25)$$

Given a pdf $f_{M,R}$, a pdf in the space of pairs of heights can be obtained with the formula:

$$f_{H_1, H_2}(h_1, h_2) = \frac{1}{h_2^2}\left(\frac{h_1 + h_2}{2}\right) \times f_{M,R}(m, r) \quad (26)$$

where the first factor is the Jacobian of the transformation, G. Casella & R. L. Berger (1990). Statistical Inference. Wadsworth & Brooks/Cole Advanced Books Software, Pacific Grove, Calif., USA, page 148 and the second factor can be estimated from experimental data. The estimation is done through by first obtaining the conditional distribution of heterozygous imbalance given mean height:

$$f_{H_1,H_2}(h_1, h_2) = \frac{1}{h_2^2}\left(\frac{h_1 + h_2}{2}\right) \times f_{R|M}(r|m)f_M(m) \qquad (27)$$

This will provide one pdf $f_{R|M}$ for all regions, but there will be one marginal for each of the regions. In the rest of the section the estimation of the conditional pdf $f_{R|M}$ and then the estimation of the marginal pdf's $f_M$ for each of the regions is illustrated.

A conditional pdf $f_{R|M}$ can be obtained using data from region (1,2) and extrapolate to a pdf $f_{R|M}$ for all regions. In effect, a simulation is provided for the material which is missing in each of these three zones. A joint pdf $f_{ln(M),ln(R)}$ for variables ln(M) and ln(R) is obtained first. A conditional pdf $f_{R|M}$ is calculated from $f_{ln(M),ln(R)}$. The pdf $f_{R|M}$ is affected by the biased introduced by the threshold of 30 rfu. This bias is removed by replacing each $f_{R|M}$ with a Log normal pdf and correcting in the space of parameters mean, μ, and variance, σ, of the Log normal pdf's.

Figure 8:
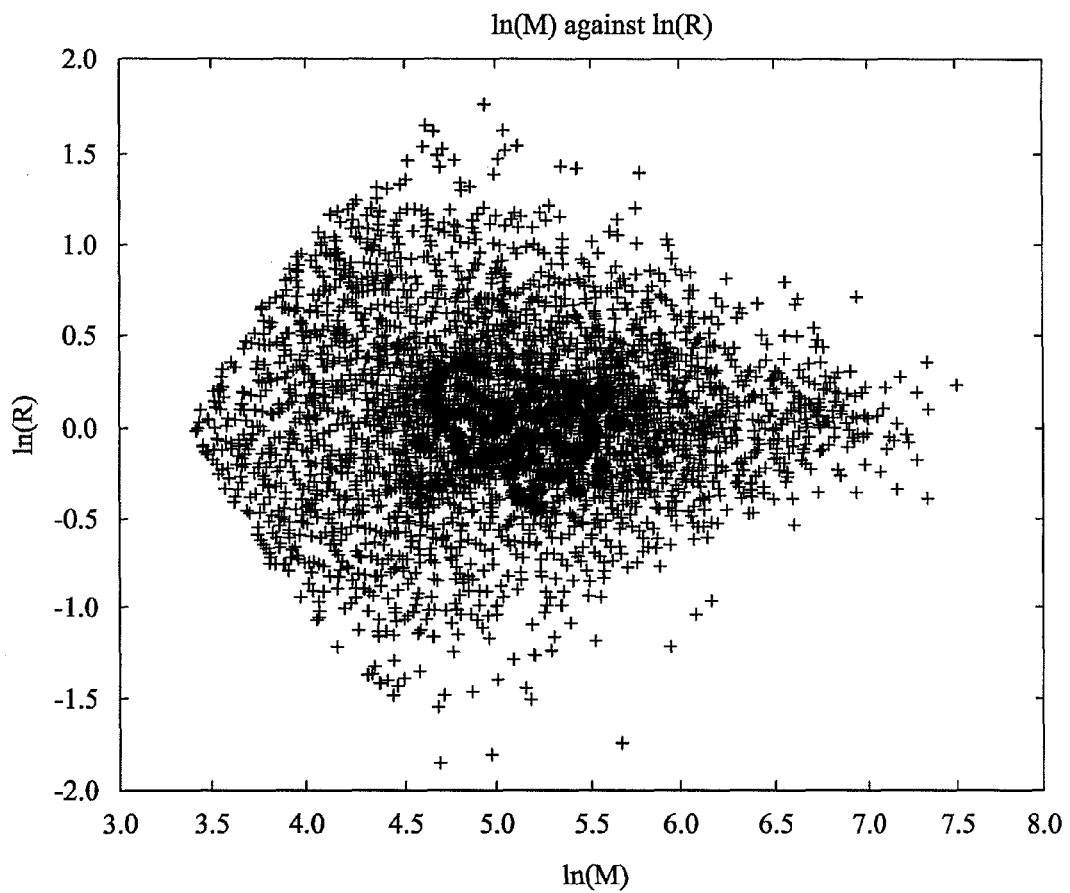
FIG. 8 is a scatter plot of mean height and heterozygote balance in a natural logarithm scale.

A two-dimensional pdf $f_{ln(M),ln(R)}$ for variables ln(M) and ln(R) is estimated using the EM-algorithm, where each Gaussian pdf has zero correlation; A. Dempster, N. Laird, and D. Rubin (1977). "Maximum likelihood from incomplete data via the EM algorithm". Journal of the Royal Statistical Society, Series B, 39(1):1-38, 1977; G. Mclachlan, D. Peel (2000). Finite mixture models. John Wiley & Sons, Inc. A scatter plot of mean height and heterozygous balance in natural logarithm scales is shown in FIG. 8. The components of the estimated mixture of Gaussians are given in Table 1.

TABLE 1

Parameters of mixture of Gaussians for an estimated pdf ln(M), ln(R)

| Component | Proportion | Mean 1 | Mean 2 | Variance 1 | Variance 2 |
|---|---|---|---|---|---|
| 1 | 0.2505 | 4.5791 | −0.0963 | 0.2581 | 0.2147 |
| 2 | 0.2528 | 4.4672 | 0.1929 | 0.2158 | 0.2203 |
| 3 | 0.2573 | 5.4292 | 0.1041 | 0.1550 | 0.1407 |
| 4 | 0.2393 | 5.7499 | 0.0585 | 0.3454 | 0.0546 |

The goodness of fit is assessed by ascertaining that the data is a likely sample of the estimated pdf. By computing one thousand samples of the same size as the data, computing the negative log-likelihood for each sample and also computing the negative log-likelihood of the data in the estimated pdf verification can be provided. The negative log-likelihood of the data falls within the range of values of the negative log-likelihoods of samples of the same size as the data. It indicates that the mixture fits the data well.

A conditional distribution of R given M can be calculated from the estimated $f_{ln(M),ln(R)}$ using the formula:

$$f_{R|M}(r|m) = \frac{f_{M,R}(m,r)}{f_M(m)} = \frac{\frac{1}{mr}f_{ln(M),ln(R)}(m,r)}{\frac{1}{m}f_{ln(M)}(m)} = \frac{f_{ln(M),ln(R)}(m,r)}{r \times f_{ln(M)}(m)}. \qquad (28)$$

The pdf $f_{ln(M)}$ is in fact a mixture of one-dimensional Gaussian distribution with the same mixing proportions as $f_{ln(M),ln(R)}$ and mean and variances given by the corresponding mean and variances. These are reported in Table 1 above.

Figure 9A:
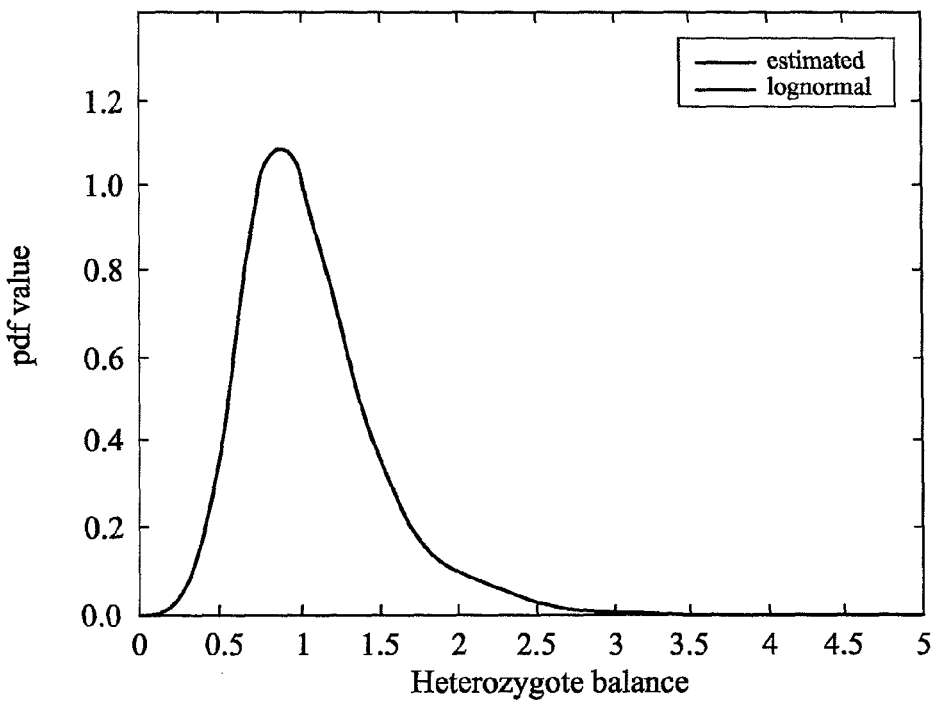
FIG. 9a shows estimated and Log normal pdf's for mean heights with rfu threshold valued at 50 rfu.
Figure 9B:
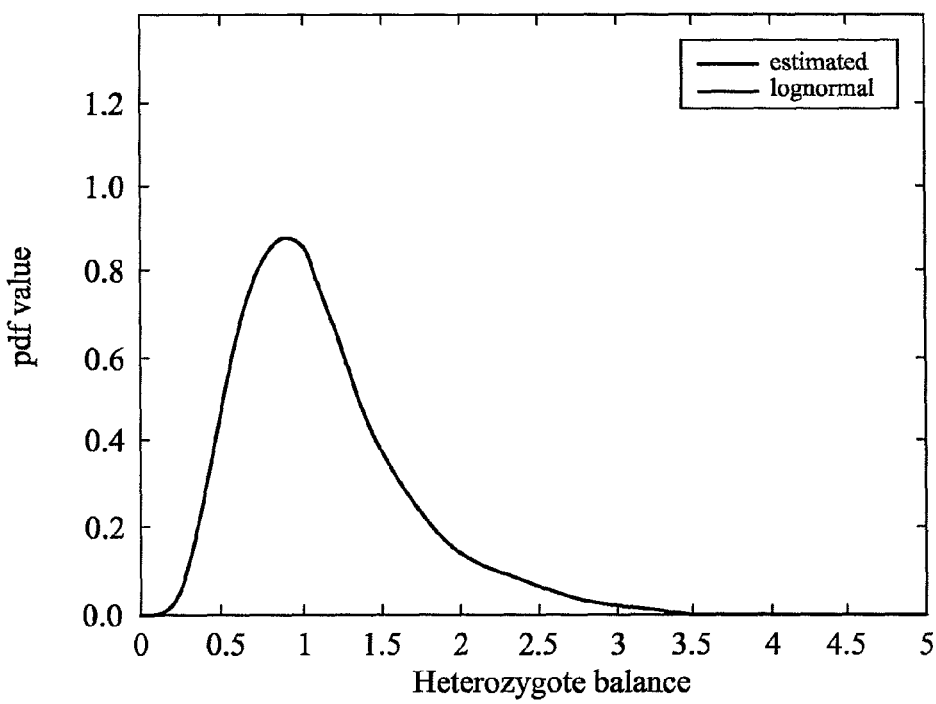
FIG. 9b shows estimated and Log normal pdf's for mean heights with rfu threshold valued at 100 rfu.
Figure 9C:
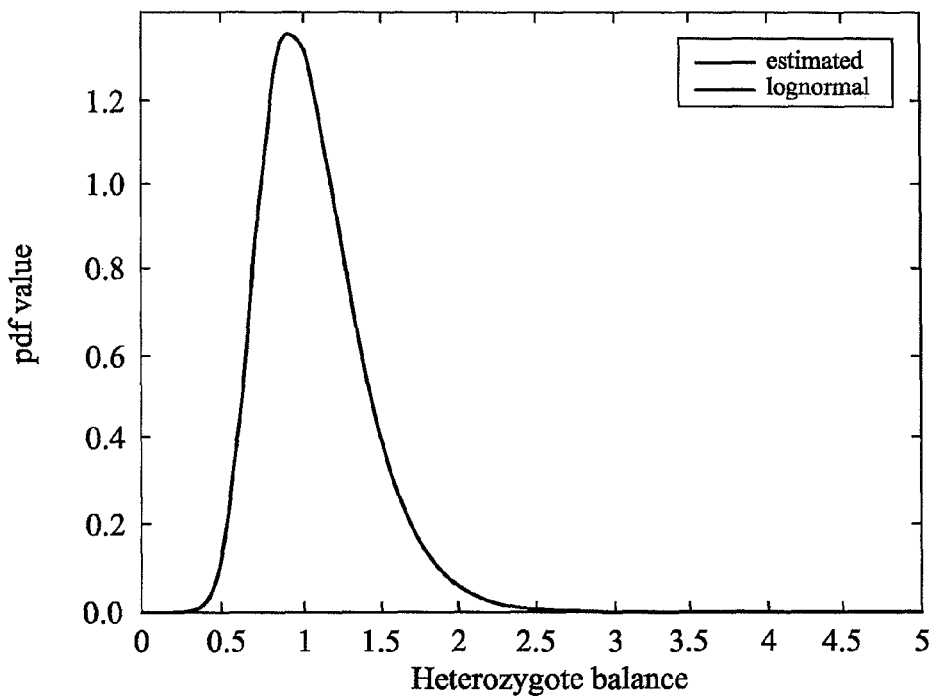
FIG. 9c shows estimated and Log normal pdf's for mean heights with rfu threshold valued at 500 rfu.
Figure 9D:
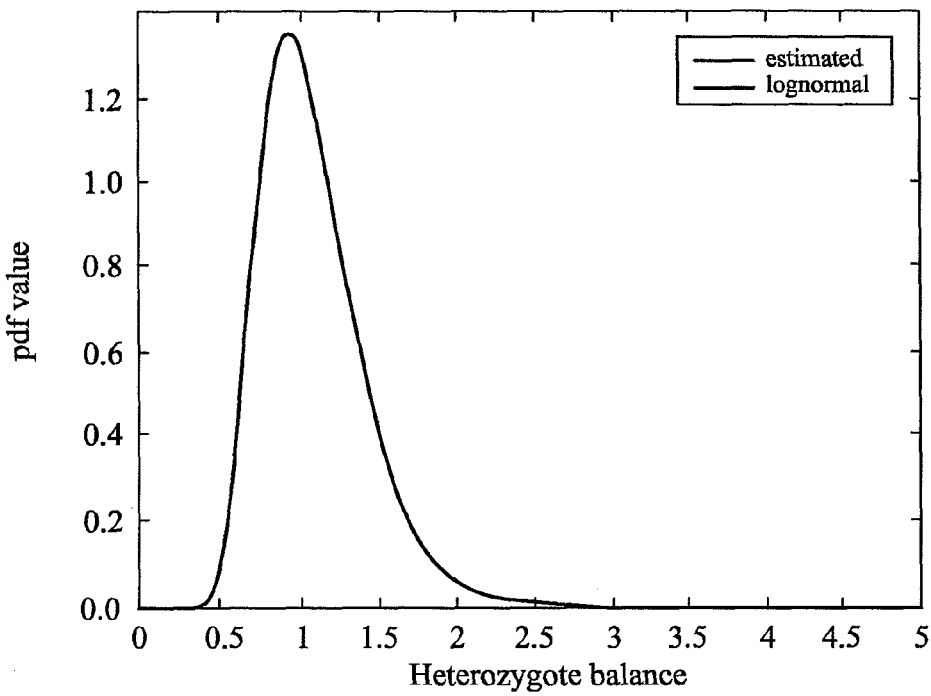
FIG. 9d shows estimated and Log normal pdf's for mean heights with rfu threshold valued at 1,000 rfu.

Several conditional pdf's are computed using the formula above. Estimated Log normal distributions are shown in FIGS. 9a, 9b, 9c and 9d. For the time being, the focus is on the estimated pdf's. Notice that the heterozygote imbalance pdf given a mean height of 50 rfu, FIG. 9a, appears to have less variability than the pdf conditional on 100 rfu, FIG. 9b. This is an effect of the bias introduced by the dropout region. Notice as well that the pdf for a mean height of 500, FIG. 9c, is very similar to the pdf for 1,000 rfu, FIG. 9d, suggesting that the variability does not significantly decrease after 500 rfu in mean height.

In FIG. 9a-d Log normal distributions that closely resemble the conditional pdf for R given M have been plotted. The pdf of the lognormal distribution is given by:

$$f_R(r) = \frac{1}{r \times \sigma \sqrt{2\pi}} \exp \frac{-(ln(r)-\mu)^2}{2\sigma^2}. \qquad (29)$$

Figures 10A, 10B:
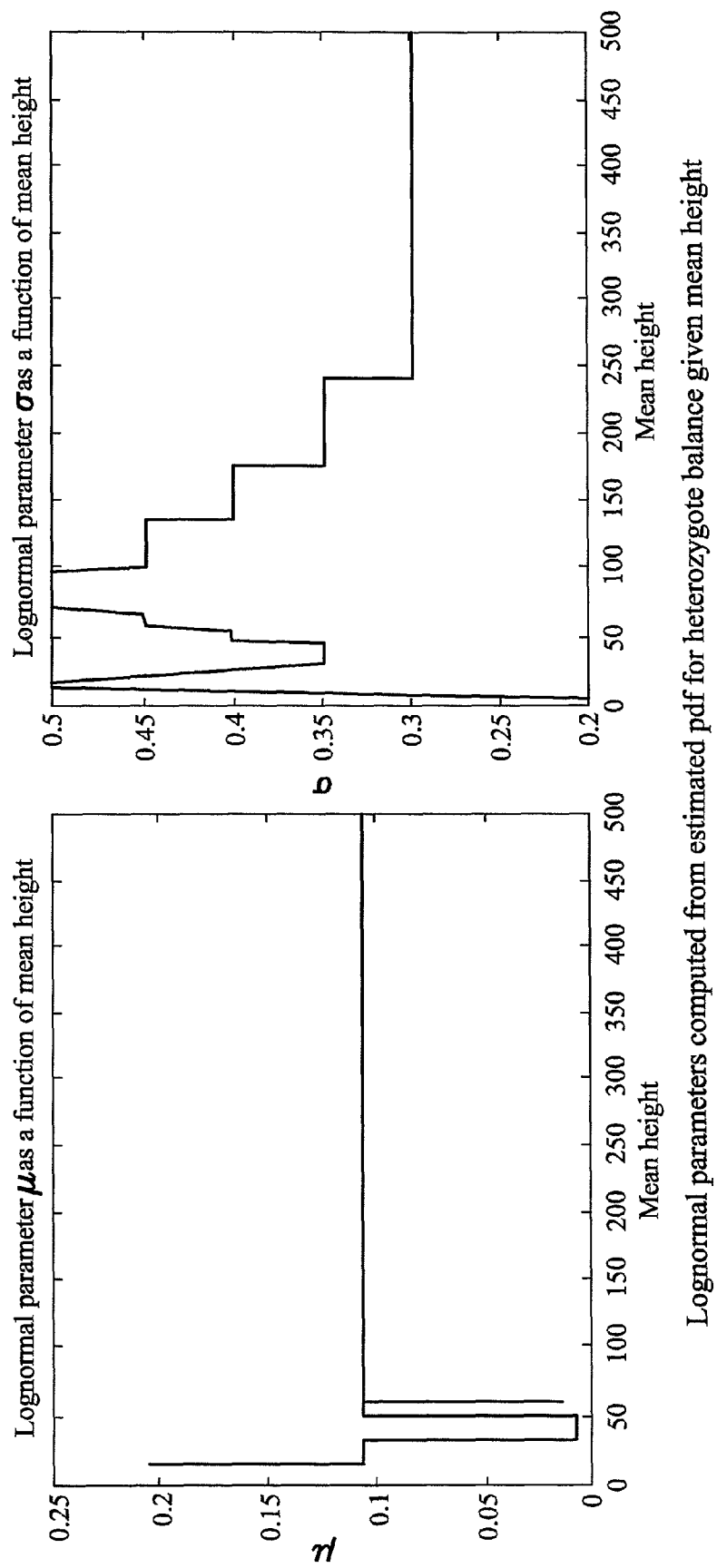
FIGS. 10a and 10b shows Log normal parameters computed from estimated pdf for heterozygote balance given mean height.

Notice that the Log normal distributions are a good fit. These can therefore correct the bias in the space of parameters (μ,σ) of the Log normal pfd's. FIGS. 10a and 10b show a plot of estimated parameters for the Log normal distribution that closely fit $f_{R|M}$ for each value of M=m. Notice that in the region M≧100 where the effect of the threshold is not present, the value of μ is constant while σ decreases as m increases.

Figures 11A, 11B:
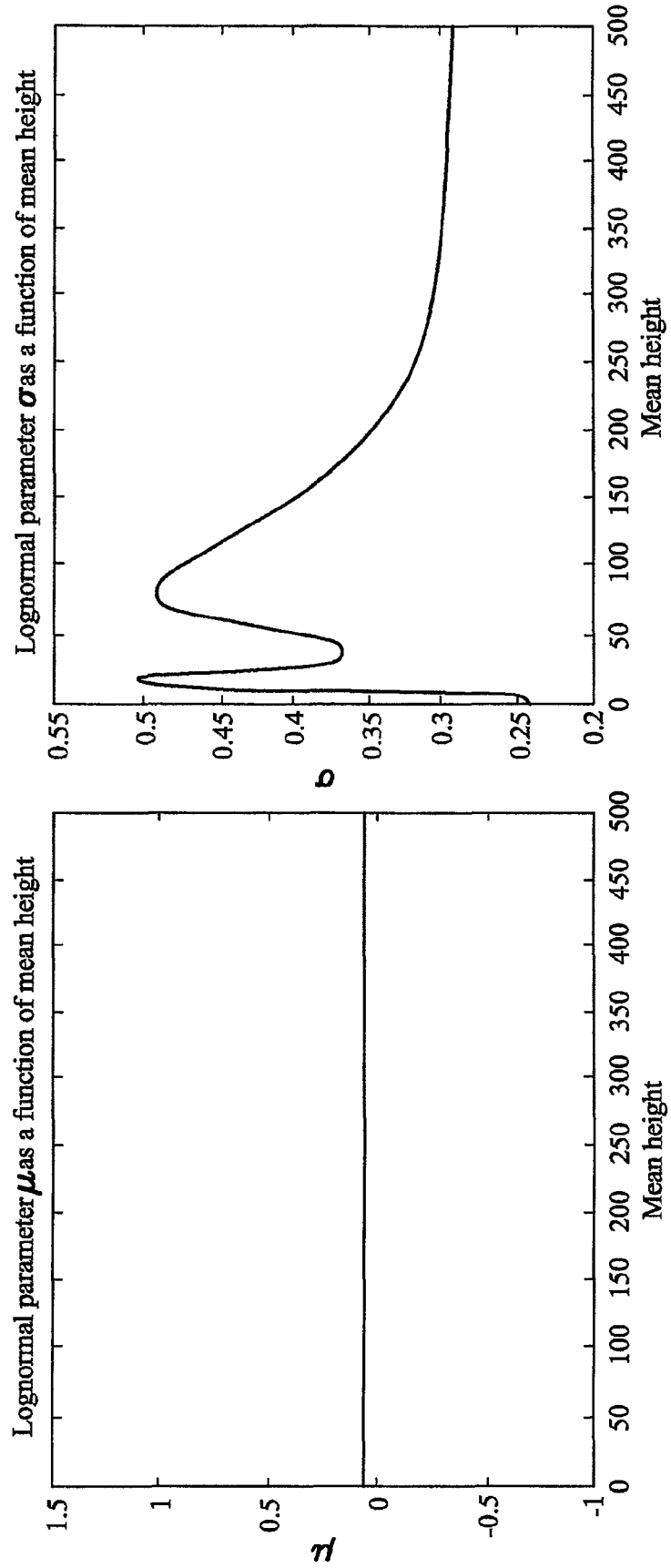
FIGS. 11a and 11b shows Log normal parameters computed from estimated pdf for heterozygote balance given mean height whilst setting $\mu=0.1069$.

In a second iteration we set μ=0.1069 corresponding to heterozygote imbalance R=1.11. In fact, this number is expected as height of the low-molecular allele tends to be larger than the height of the high-molecular weight allele. We then run the estimation procedure for σ again. FIG. 11 shows the estimated values of σ for each value of m.

Figure 12:
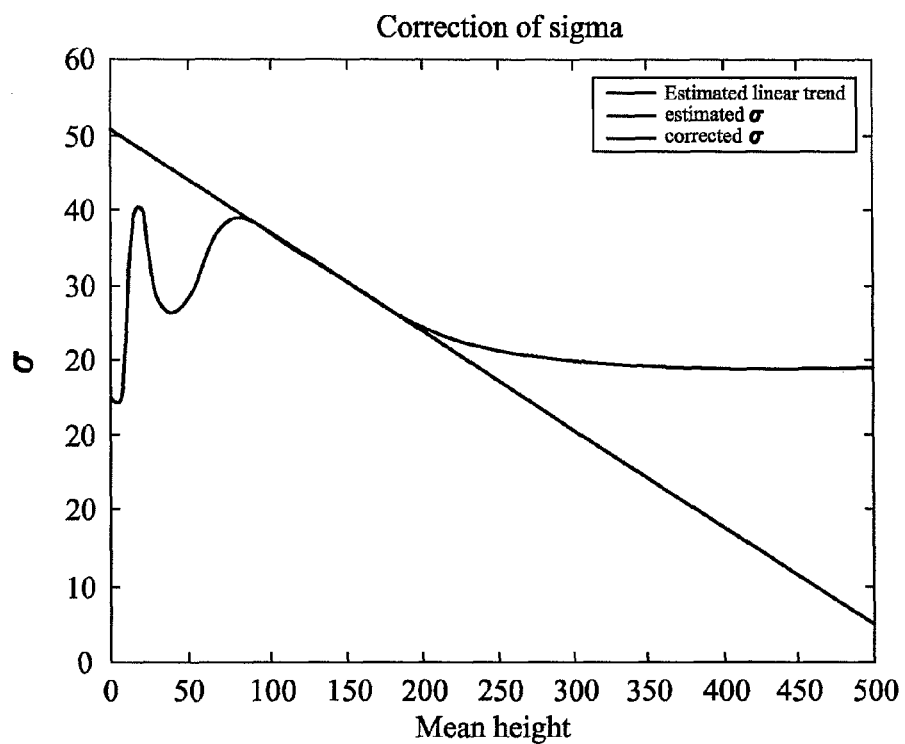
FIG. 12 shows corrected $\sigma$ through a estimated linear trend.

To extrapolate the increasing trend to lower values of M, several polynomials were fitted to values of σ in region from 80 to 200 rfu. A line was the best fit and it was chosen for extrapolating σ in region (0,80). FIG. 12 displays the estimated line and the extrapolated values.

In these examples, Log normal distributions are used, but other extrapolatable distributions, such as gamma distributions can be used.

From this a family of Log normal distributions have been obtained:

$$f_{R|M}(r|m) = \frac{1}{r \times \sigma(m)\sqrt{2\pi}} \exp \frac{-(ln(r)-\mu)^2}{2[\sigma(m)]^2} \qquad (30)$$

where μ=0.1069 and σ(m) is given by the corrected σ value in FIG. 12.

Other components in the proposed two-dimensional distribution for peak height are pdf's for mean in each of the four regions. For region (0,0) both peak heights are not known and thus follow a uniform distribution in the interval [0,30]. A pdf for mean height is therefore also a uniform distribution in this interval, i.e.

$$f_M(m) = p_{(0,0)} \times \frac{1}{30} \qquad (31)$$

where $p_{(0,0)}$ the proportion of pair of heights that fall in region $(0,0)$ and takes the value 0.1012. Of course, other values than 30 rfu's for the threshold t can be employed.

Obtaining a pdf for region $(1,0)$ requires more effort. First a distribution for peak height $(h_1,h_2)$ in this region is obtained and them used to calculate a distribution for mean height. Although the goal is to obtain a pdf for $(h_1,h_2)$, this distribution does not have the extrapolated pdf for heterozygote imbalance given mean height. A pdf for mean height is therefore extracted and used the extrapolated distribution and transformed back to the space of $(h_1,h_2)$.

Figure 13:
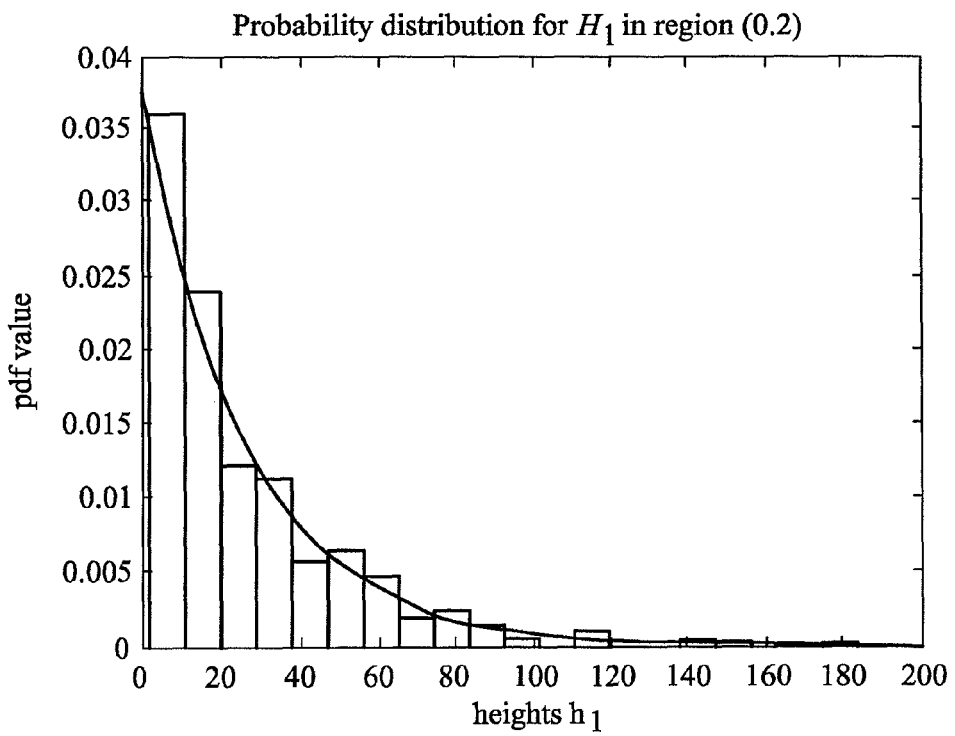
FIG. 13 is a probability distribution for $H_1$ in region $(1,0)$. The estimated parameter $\lambda_{(1,0)}=26.24$; the estimation was done by subtraction 29 to the height values.

A joint distribution can be defined in this region by assuming that the variables $h_1$ and $h_2$ are independent. Given that we do not know the value of $h_2$, we can assume that they follow a uniform distribution in the interval (0,30). The values that variable $h_2$ follow is an exponential distribution, see FIG. 13. The goodness of fit was further corroborated with a Kolmogorov-Smirnoff test.

A pdf for region $(1,0)$ is given by $$f_{H_1,H_2}(h_1,h_2) = p_{(1,0)} \times \frac{1}{30} \times \frac{1}{\lambda_{(1,0)}} \exp\left\{-\frac{h_1-30}{\lambda_{(1,0)}}\right\} \qquad (32)$$

where $p_{(1,0)}$ is the proportion of height pairs that fall in region $(1,0)$ and take the value of 0.0448.

A pdf for mean height M can be obtained by first using the transformation $$(h_1, h_2) \mapsto \left(m = \frac{h_1+h_2}{2}, n = \frac{h_1-h_2}{2}\right). \qquad (33)$$

and then use the Jacobian of the transformation to obtain a two-dimensional pdf for (M,N). The marginal pdf for m can be obtained through integration. The two-dimensional pdf for (M,N) is given by:

$$f_{M,N}(m,n) = 2 \times f_{H_1,H_2}(h_1,h_2). \qquad (34)$$

It can be re-written as $$f_{M,N}(m,n) = p_{(1,0)} \times \frac{1}{15} \times \frac{1}{\lambda_{(1,0)}} \exp\left\{-\frac{m+n-30}{\lambda_{(1,0)}}\right\}. \qquad (35)$$

Before we integrate N to obtain a pdf or M, we need to describe the sample space for (M,N). It is the area in the rectangle.

The resulting pdf for M is given by:

$$f_M(m) = p_{(1,0)} \times \frac{1}{15} \times \left[1 - \exp\left\{-\frac{2m-30}{\lambda_{(1,0)}}\right\}\right] \qquad (36)$$

if $m \in [15,30)$, and $$f_M(m) = p_{(1,0)} \times \frac{1}{15} \times \left[\exp\left\{-\frac{2(m-30)}{\lambda_{(1,0)}}\right\} - \exp\left\{-\frac{2m-30}{\lambda_{(1,0)}}\right\}\right] \qquad (37)$$

if $m \geq 30$.

Figure 14:
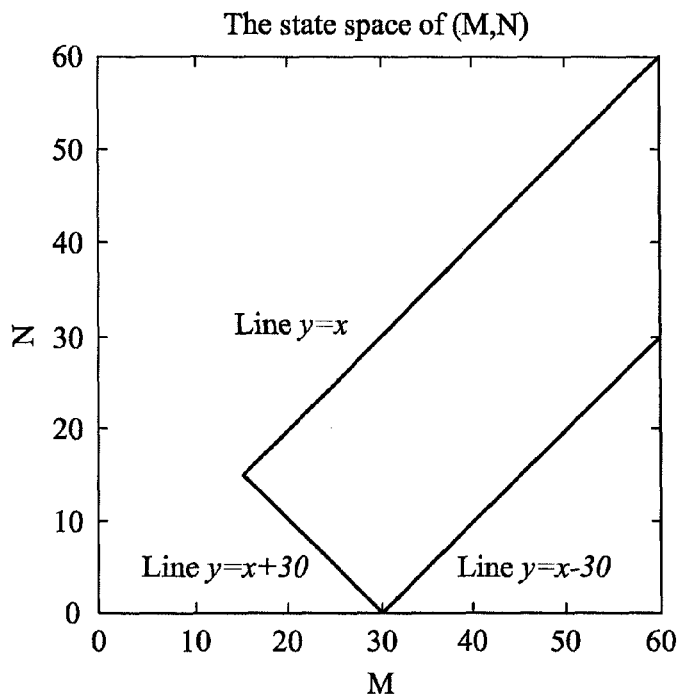
FIG. 14 shows the state space of (M,N) is the area within the rectangle.
Figure 15:
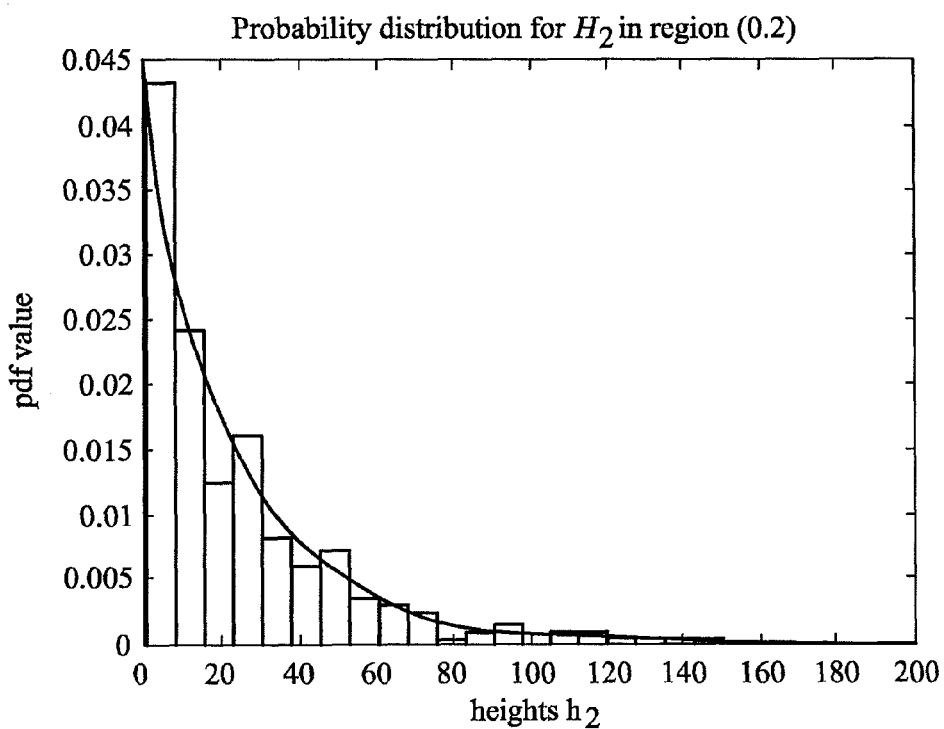
FIG. 15 is a probability distribution for $H_1$ in region $(1,0)$; the estimated parameter $\lambda_{(0,2)}=25.30$; the estimation was done by subtraction 30 to the height values.

The methodology for obtaining a pdf for mean height in region $(0,2)$ is the same as for region $(1,0)$. A pdf for $(H_1,H_2)$ is given by:

$$f_{H_1,H_2}(h_1,h_2) = p_{(0,2)} \times \frac{1}{30} \times \frac{1}{\lambda_{(0,2)}} \exp\left\{-\frac{h_2-30}{\lambda_{(0,2)}}\right\}. \qquad (38)$$

where $p_{(0,2)}$ is the proportion of height pairs that fall in region $(0,2)$ and is equal to 0.0325. Constant $\lambda_{(0,2)}$ is the parameter of an exponential pdf estimated from values of $h_2$ translated by 30, see FIG. 14. The goodness of fit was further corroborated with a Kolmogorov-Smirnoff test.

The method for calculating a marginal for M in region $(0,2)$ is the same as for region $(1,0)$. The resulting pdf is given by:

$$f_M(m) = p_{(0,2)} \times \frac{1}{15} \times \left[1 - \exp\left\{-\frac{2m-30}{\lambda_{(0,2)}}\right\}\right] \qquad (39)$$

if $m \in [15,30)$, and $$f_M(m) = p_{(0,2)} \times \frac{1}{15} \times \left[\exp\left\{-\frac{2(m-30)}{\lambda_{(0,2)}}\right\} - \exp\left\{-\frac{2m-30}{\lambda_{(0,2)}}\right\}\right] \qquad (40)$$

if $m \geq 30$.

Finally, a pdf $f_M$ for region $(1,2)$ can be obtained from the two-dimensional pdf estimated for $(\ln(M),\ln(R))$. The resulting is a mixture of one-dimensional Gaussians where the mixture proportion is the same as those reported in Table 1. The means are given in the column with heading "Mean 1" and the variances are given in the column with heading "Variance 1"[1]. A pdf for M in region $(1,2)$ is given by:

[1]Matlab: fitMeanHeightPDF.m $$f_M(m) = p_{(1,2)} \times \sum_{i=1}^{4} p_i \times f(m \mid \mu_i, \sigma_i) \qquad (41)$$

where $p_{(1,2)}$ is the proportion of height pairs that fall in region $(1,2)$ and $p_i$ is the mixing proportion of the Gaussian components and $f(m|\mu_i,\sigma_i)$ are the Gaussian pdf's.

We have defined all the components of a two-dimensional pdf for pair of heights for all regions as defined in Equation (27). The conditional pdf $f_{R|M}$ is given by the family of Log-normal pdf's with a fixed value of $\mu$ and values of $\sigma(m)$ given in FIG. 12. The marginal distributions $f_M$ have been given for all regions above. This pdf form is one of the building blocks in the calculation of LRs in subsequent sections.

Generating a 2D Probability Distribution Function for Heterozygous Donors—Method Two—Approach c In approach b above, an approach for dealing with the censoring of the peaks by the rfu limit imposed was discussed. This approach provides a further variant to that manner of dealing with the left censored peaks.

In approach b, a pdf $f_{M,R}$, a pdf in the space of pairs of heights, was described as being obtained with the formula:

$$f_{H_1,H_2}(h_1, h_2) = \frac{1}{h_2^2}\left(\frac{h_1+h_2}{2}\right) \times f_{M,R}(m, r)$$

where the first factor is the Jacobian of the transformation and the second factor was estimated from experimental data. The estimation was done through by first obtaining the conditional distribution of heterozygous imbalance given mean height:

$$f_{H_1,H_2}(h_1, h_2) = \frac{1}{h_2^2}\left(\frac{h_1+h_2}{2}\right) \times f_{R|M}(r|m)f_M(m)$$

This provided one pdf $f_{R|M}$ for all regions, but with one marginal for each of the regions. Approach b then described the estimation of the conditional pdf $f_{R|M}$ and then the estimation of the marginal pdf's $f_M$ for each of the regions illustrated.

In approach c, the same approach is taken to that of approach b in the use of the formula:

$$f_{H_1,H_2}(h_1, h_2) = \frac{1}{h_2^2}\left(\frac{h_1+h_2}{2}\right) \times f_{R|M}(r|m)f_M(m)$$

and in the estimation of the conditional pdf $f_{R|M}$. The variation is in the manner by which the estimation of the marginal pdf's $f_M$ is provided. In this further approach, consideration of the possible range for the values of the peak-heights, even those recorded as zero, are taken into account.

The first step is the selection of a family of probability distributions $f(m|\theta)$ where c is the set of parameters specifying the family of distributions. Variable m is the mean height $(h_1+h_2)/2$. The values of $h_1$ and $h_2$ are affected by the threshold t and thus $h_1$ can be either greater than or equal to t or recorded as zero if it is smaller than t. The values of m are affected by left-censoring of $h_1$ and $h_2$ and the definition of the likelihood of $\theta$ given the observation on M are affected accordingly.

If $h_1<t$ and $h_2<t$, the m<t. In this case m is left-censored and the likelihood function for these m's as $F(t|\theta)$ where F is the cumulative probability distribution (CDF) of the previously chosen family of distributions. If $h_1<t$ and $h_2\geq t$, then m is interval-censored, that is it falls in the interval from 0.5t to $0.5(t+h_2)$. The likelihood for the m's is $F(0.5(t+h_2)|\theta)-F(0.5t|\theta)$. Similarly for the contrary case where $h_2<t$ and $h_1\geq t$ the likelihood of m is $F(0.5(t+h_1)|\theta)-F(0.5t|\theta)$. If $h_1\geq t$ and $h_2\geq t$, then there is no censoring and the likelihood is given by $f(m|\theta)$. The overall likelihood is given by multiplying the likelihood for each pair of heights $h_1$ and $h_2$, including those that fall below the threshold t and are recorded as zero:

$$L(\theta|m) = \Pi\{F(t|\theta) : h_1 < t, h_2 < t\} \times$$

$$\Pi\{F(0.5(t+h_2)|\theta) - F(0.5t|\theta) : h_1 < t, h_2 \geq t\} \times$$

$$\Pi\{F(0.5(t+h_1)|\theta) - F(0.5t|\theta) : h_1 \geq t, h_2 < t\} \times$$

$$\Pi\{f(0.5(h_1+h_2)|\theta) : h_1 \geq t, h_2 \geq t\}$$

The parameters encoded in $\theta$ are choose to maximise the likelihood given above.

Establishing Likelihood Ratios

Having established the underlying 2D pdf for peak heights in the heterozygous case, $f_{het}(h_1,h_2)$, and 2D pdf for peak height in the homozygous case, $f_{hom}(h_1)$, it is possible to move on to establish the likelihood ratios in various situations of interest.

These situations considered in turn and in detail are a variety of situations that are encountered, particularly in the context of forensic science.

The various situations are:
1) in an evidential context, a single source sample, without conditioning on DNA quantity;
2) in an evidential context, a single source sample, with conditioning on DNA quantity;
3) in an intelligence context, a single source sample, without conditioning on DNA quantity;
4) in an intelligence context, a single source sample, with conditioning on DNA quantity;
5) in an evidential context, a mixed source sample, without conditioning on DNA quantity;
6) in an evidential context, a mixed source sample, with conditioning on DNA quantity;
7) in an intelligence context, a mixed source sample, without conditioning on DNA quantity; and
8) in an intelligence context, a mixed source sample, with conditioning on DNA quantity.

Situation 1—An Evidential Context—A Single Source Sample—Without Conditioning on DNA Quantity In an evidential context, the relative likelihood's of two hypotheses are normally being considered. Generally, these will be a prosecution hypothesis and a defence hypothesis. The consideration, the likelihood ratio, can be generally expressed as:

$$LR = \frac{Pr(C|S, H_p)}{Pr(C|S, H_d)} \quad (42)$$

where
C is the crime profile consisting of peak heights, for example $C=\{h_1,h_2\}$ or $C=\{h_1\}$, $h=\{h_1,h_2<t\}$, $h=\{h_1<t\}$
S is the suspect's genotype, for example S={1,2}, or S={1, 1}.
$H_p$ is the prosecution hypothesis stating "The suspect left the stain at the scene of crime";
$H_d$ is the defence hypothesis stating "Someone else left the stain in the crime scene. This includes a defence hypothesis of a putative donor; that is either related or unrelated to the suspect, and from the same ethnicity or different ethnicity.

The LR can be expanded as:

$$LR = \frac{Pr(C|S, H_p)}{\sum_i Pr(C|U_i, S, H_d)Pr(U_i, S, H_d)} \quad (43)$$

where $U_i$ is one of the supposed donor stated in $H_d$. Given that the quantities in C are continuous, the LR is written as:

$$LR = \frac{f(C|S, H_p)}{\sum_i f(C|U_i, S, H_d)Pr(U_i, S, H_d)} \quad (44)$$

where the f means that these factors are likelihoods and not probabilities.

There are a number of ways in which the second factor $Pr(U_i|S)$ can be computed using the method given by Balding et al. (2005) and Buckleton et al.(2005), referenced above, which may include considerations of relatedness between the unknown contributor and the suspect.

The factors $f(C|S,H_p)$ and $f(C|U_i,S,H_d)$ state the same type of calculation: the likelihood of observing the set of peak heights in C given a supposed donor. Therefore the discussion for their calculation is simplified as:

$$f(C|G) \tag{45}$$

where G denotes the supposed donor genotype.

This general form of the likelihood is key to the operation of the invention and its benefits.

The estimation of $f(C|G)$ from experimental data, as provided in the pdf forming methods discussed above, has not previously been envisaged or provided.

The estimation can come from the dilution data approach of heterozygous sources, method 1, in particular. The homozygous source methods could be used for homozygous situations.

As far as the estimation of $f(C|G)$ is concerned, this can be done by grouping data from all loci to general a single estimation of $f(C|G)$ covering all the loci considered. It is equally possible to provide a separate estimation of $f(C|G)$ for each locus. A variety of ways for generating the estimation of $f(C|G)$ using two-dimensional density estimations apply.

In the following sections a more detailed application of the approach to evidential contexts is provided for the four scenarios:

a) Suspect is heterozygous and crime profile has one peak;
b) Suspect is heterozygous and crime profile has two peaks;
c) Suspect is heterozygous and crime profile contains no peaks;
d) Suspect is homozygous and crime profile contains one peak;
e) Suspect is homozygous and crime profile contains one peak.

Suspect is Heterozygous and Crime Profile has One Peak

In this situation, $C=\{h_b\}$ and $S=\{a,b\}$. The likelihood ratio is given, consistent with equation 1 above, by, $$LR = \frac{f(h_b \mid S = \{a, b\}, H_p)}{f(h_b \mid S = \{a, b\}, H_d)}. \tag{1.1}$$

Figure 17:
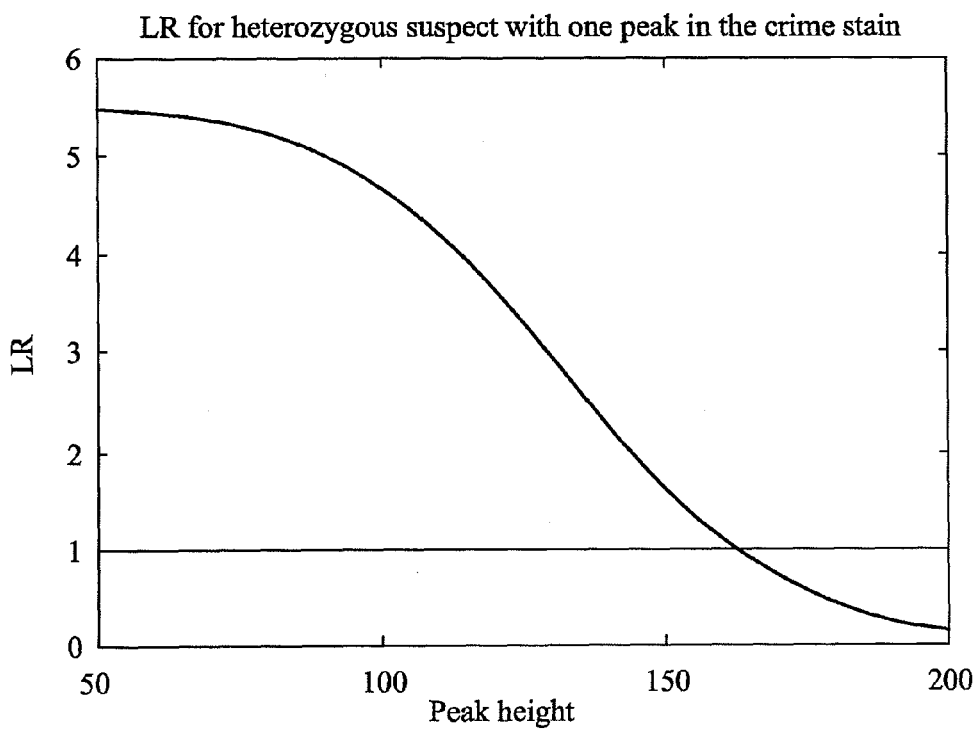
FIG. 17 shows the variation in LR, for locus D2 where the suspect is heterozygous and there is only one peak in the crime stain, with peak height.

The numerator then becomes, $$f(h_a < t, h_b \mid S = \{a, b\}, H_p) = f_{het}(h_a < t, h_b) = \int_0^t f_{het}(h_a, h_b) dh_a \tag{1.2}$$

where $h_a$ is a peak height smaller than the threshold and so is not observed in the results. This is the type of situation illustrated in FIG. 17, with $h_a$ corresponding to the situation for PK1.

The term in the right-hand-side of Equation (1.2) is a pdf in two-dimensions of the type discussed above in the pdf's for heterozygote sections.

The denominator in equation (1.1) is given by, $$f(h_b|H_d)=f(h_b|U=\{b,b\},H_d)Pr(U=\{b,b\}|S=\{a,b\}),H_d+ \\ f(h_a<t,h_b|U=\{b,Q\},H_d)Pr(U=\{b,Q\}|S=\{a,b\}) \\ H_d. \tag{1.3}$$

where Q is any other allele identity than a.

The second factors in the right-hand side of equation (1.3), $Pr(U=\{b,b\}|S=\{a,b\})H_d$ and $Pr(U=\{b,Q\}|S=\{a,b\})H_d$ can be computed using methods described in Balding (2005) and Buckleton et al. (2005) which includes cases where the suspect and the unknown contributors are from the same and different ethnic groups, and cases when the suspect and unknown contributor are related.

The first factors of the right-hand side of equation 1.3 will now be described in more detail.

The second factor is computed as follows:

$$f(h_b|U=\{b,b\},H_d)=f_{hom}(h_b). \tag{1.4}$$

where $f_{hom}$ is the one-dimensional pdf as discussed above. The third factor is computed with the formula:

$$f(h_b, h_a < t \mid U = \{b, Q\}, H_d) = \\ f_{het}(h_b, h_Q < t) = \int_0^t f_{het}(h_b, h_a) dh_Q \tag{1.6}$$

where $h_Q$ is smaller than the threshold.

This provides a determinable value for the likelihood ratio for the situation of, suspect is heterozygous and crime profile has one peak.

Suspect is Heterozygous and Crime Profile has Two Peaks

In this situation, $C=\{h_a,h_b\}$ and $S=\{a,b\}$. The LR is given by:

$$LR = \frac{f(C = \{h_a, h_b\} \mid S = \{a, b\}, H_p)}{f(C = \{h_a, h_b\} \mid S = \{a, b\}, H_d)}. \tag{2.1}$$

The numerator is given by:

$$f(C=\{h_a,h_b\}|S=\{a,b\},H_d)=f_{het}(h_a,h_b). \tag{2.2}$$

The denominator is given by:

$$f(C=\{h_a,h_b\}|S=\{a,b\},H_d)=f_{het}(h_a,h_b)Pr(U=\{a,b\}|S=\{a,b\},H_d) \tag{2.3}$$

The second term in the right hand side of Equation 2.3 can be computed using methods described in Balding (2005) and Buckleton et al. (2005) which includes cases where the suspect and the unknown contributors are from the same and different ethnic groups, and cases when the suspect and unknown contributor are related. The first term is calculated from a two-dimensional pdf for peak heights.

The LR is then given by:

$$LR = \frac{1}{Pr(U = \{a, b\} \mid S = \{a, b\})}. \tag{2.4}$$

This provides a determinable value for the likelihood ratio for the situation of suspect is heterozygous and crime profile has two peaks. This assumes that different contributors having the same genotype will have the same peak height distributions.

Suspect is Homozygous and the Crime Profile Contains One Allele

In this situation, $C=\{h_b\}$ and $S=\{b,b\}$. The LR is given by:

$$LR = \frac{f(h_b \mid S = \{b, b\}, H_p)}{f(h_b \mid S = \{b, b\}, H_d)}. \tag{3.1}$$

The numerator is given by:

$$f(h_b|S=\{b,b\},H_p)=f_{hom}(h_b) \quad (3.2)$$

a density function estimated for homozygous contributors.

The denominator is given by:

$$f(h_b | S = \{b, b\}, H_d) = \quad (3.3)$$
$$f(h_b | U = \{b, b\}, H_d)Pr(U = \{b, b\} | S = \{b, b\}, H_d) +$$
$$f(h_b, h_a < t | U = \{b, Q\}, H_d)Pr(U = \{b, Q\} | S = \{b, b\}H_d).$$

The term:

$$f(h_b|U=\{b,b\},S=\{b,b\},H_d)=f_{hom}(h_b). \quad (3.4)$$

is the same as the numerator. The term:

$$f(h_b, h_Q < t | U = \{b, Q\}, H_d) = \quad (3.5)$$
$$f_{het}(h_b, h_Q < t) = \int_0^t f_{het}(h_b, h_a) dh_Q.$$

can be obtained by estimating a pdf for the peak heights.

This provides a determinable value for the likelihood ratio for the situation of suspect is heterozygous and the crime profile has one allele.

As previously mentioned, the homozygous situation starts out relating to a 1D pdf and has to be converted to a 2D pdf for compatibility in approaches. This 2D approach extends to the likelihood calculation too. The approach stems from the observation that a homozygous sample with height $h_1$ is similar to observing a heterozygous sample with approximate heights $0.5h_1$ and $0.5h_1$.

The likelihood for a homozygous donor is then given by $$f(C = \{h_1\} | G = \{1, 1\}) = \quad (46)$$
$$\int_0^1 f(C = \{\alpha h_1, (1-\alpha)h_1\} | G = \{1, 1\}) f(\alpha) d\alpha$$

where $f(C=\{\alpha h_1,(1-\alpha)h_1\}|G=\{1,1\})$ is a likelihood function computed in a two-dimensional likelihood for a heterozygote and $f(\alpha)$ is a probability density function for $\alpha$, where $\alpha$ is the proportion of the sample. Alternatively we can approximate this quantity by:

$$f(C = \{h_1\} | G = \{1, 1\}) = f(C = \{\alpha h_1, (1-\alpha)h_1\} | G = \{1, 1\}) \quad (47)$$

for an $\alpha$ close to 0.5.

In this section, the approach has been provided without consideration as to the DNA quantity involved; the next section conditions on DNA quantity. For ease of presentation, however, the above mentioned approach extended to when we condition to DNA quantity, $\chi$, is mentioned here. The formulae remain valid, and they become:

$$f(C = \{h_1\} | G = \{1, 1\}, \chi_i) = \quad (48)$$
$$\int_0^1 f(C = \{\alpha h_1, (1-\alpha)h_1\} | G = \{1, 1\}, \chi_i) f(\alpha) d\alpha$$

where $f(C=\{\alpha h_1,(1-\alpha)h_1\}|G=\{1,1\},\chi_i)$ is a likelihood function for a heterozygote contributor estimated from data obtained with targeted DNA quantity $\chi_i$.

Alternatively:

$$f(C = \{h_1\} | G = \{1, 1\}, \chi_i) = f(C = \{\alpha h_1, (1-\alpha)h_1\} | G = \{1, 1\}, \chi_i) \quad (49)$$

for an $\alpha$ close to 0.5.

Situation 2—An Evidential Context—A Single Source Sample—With Conditioning on DNA Quantity In situation 1, above, we discussed how the calculation is simplified as:

$$f(C|G) \quad (50)$$

where G denotes the supposed donor and that this general form of the likelihood is key to the operation of the invention and its benefits.

In the extension of the approach that now follows, the likelihood can also be computed by conditioning on DNA quantity, in the form:

$$f(C|G) = \sum_j f(C|G, \chi_j) Pr(\chi_j | I(h)) \quad (51)$$

where $Pr(\chi_j|I(h))$ is a probability distribution of DNA quantity given peak height information, $I(h)$.

The calculation of $f(C|G)$ can be done for each different DNA quantity considered through the control samples. In effect, for each quantity of DNA a dataset is generated using the general approaches previously described. This data is stored for future use. The relevant distribution to the DNA quantity in the analysis situation is then selected from these and used.

The probability distribution for $Pr(\chi_j|I(h))$ relates to a list of discrete probabilities for $\chi_1$ to $\chi_j$, where $$\sum_j Pr(\chi_j | I(h)) = 1.$$

The distribution can be obtained by considering an observed distribution from the control samples. There are various ways of combining the control sample results to achieve this.

It is possible to considering all the heights, h, observed for each locus in a control sample. This gives a mean h for a control sample across all its loci. The mean h's for repeats at the same quantity $\chi$ can then be grouped together across multiple control samples. Hence, $\{\bar{h}_j\}$, j=1,2, . . . ,m. This allows the estimation of a distribution $f(\bar{h}|\chi_i)$ and the fitting of a distribution to that. The estimation can be provided by various approached for estimating probability distributions in 1D. For example, this distribution can be estimated using mixtures of 1D normal distributions using EM-algorithm, see for instance, A. Dempster, N. Laird, and D. Rubin (1977). "Maximum likelihood from incomplete data via the EM algorithm". Journal of the Royal Statistical Society, Series B, 39(1):1-38.

Other approaches could consider the position locus by locus, with the process of obtain a mean height at each $\chi$ and providing the distribution being performed separately for the different loci.

Both the sets of information for equation 5 (which equation) can be obtained for one or more loci, preferably, but not necessarily including the locus on which the approach is being used.

It is possible for the calculation of $Pr(X=\chi_i|I(h))$ for a locus to be performed in a sequential fashion based on an ordering $L_1, L_2, \ldots, L_n$ of the loci. In that instance, the process starts by setting $Pr(X=\chi_i|I(h))$ for $L_1$ to a uniform distribution. This is in part because there is no information available as to I(h). It is then possible to compute $Pr(X=\chi_i|I(h))$ for $L_2$ based on the assumption for I(h) from $L_1$. The prior knowledge of I(h) for $L_1$ is of benefit. The process then computes $Pr(X=\chi_i|I(h))$ for $L_3$ based on I(h) from $L_1$ and $L_2$, with the process continuing in this manner until $Pr(X=\chi_i|I(h))$ for $L_n$ is computed based on I(h) from $L_1, L_2, \ldots, L_{n-1}$. This provides the best use of the prior knowledge to compute the various Pr's, but without generating a circularity issue in the processing.

To compute $Pr(X=\chi_i|I(h))$ that function can be equated to:

$$Pr(X = \chi_i | \bar{h}) = \frac{f(\bar{h} | X = \chi_i) Pr(X = \chi_i)}{\sum_j f(\bar{h} | X = \chi_j) Pr(X = \chi_j)}$$

where:

$f(\bar{h}|X=\chi_i)$ is a 1D distribution calculated for data for DNA only, $\chi=\chi_i$.

The likelihoods $f(C|G_i)$ and its version conditional on DNA quantity $f(C|G_i,\chi_i)$ are key to the invention. The estimation of $f(C|G_i,\chi_i)$ from experimentally derives data has not previously been envisaged or provided. Once again:

this can be provided from dilution data;

the estimation of $f(C|G_i,\chi_i)$ can be done by grouping data from all loci, potentially with the estimation rendering one $f(C|G,\chi_i)$ for all loci, but with a separate $f(C|G,\chi_i)$ for each DNA quantity $\chi_i$;

the estimation of $f(C|G,\chi_i)$ can be done once per locus, potentially with the estimation rendering one $f(C|G,\chi_i)$ for each locus and for each DNA quantity $\chi_i$;

the estimation of $f(C|G,\chi_i)$ can be done using any method for estimating a two-dimensional density estimation;

the estimation of $f(C|G,\chi_i)$ can be done using the method described in the heterozygous donors, method one and/or homozygous donors method one approaches.

Equally, the estimation of $Pr(X=\chi_i|I(h))$ from experimentally derived data has not previously been provided or envisaged. Again this could involve:

the estimation of $Pr(X=\chi_i|I(h))$ from dilution data;

the peak height information I(h) being any function of peak height, for example the mean of two peak heights or the sum of the heights;

the estimation of $Pr(X=\chi_i|I(h))$ for a locus being based on I(h) from the same locus or from one or more other loci.

Situation 3—An Intelligence Context—A Single Source Sample—Without Conditioning on DNA Quantity In an intelligence context, a different issue is under consideration to that approached in an evidential context. The intelligence context seeks to find links between a DNA profile from a crime scene sample and profiles stored in a database, such as The National DNA Databases®, which is used in the UK. The process is interested in the genotype given the collected profile.

Thus in this context, the process starts with a crime profile C and is interested in proposing an ordered list of suspect's profiles, where the first profile in the list is the genotype of the most likely donor. This task is usually done by proposing a list of genotypes $\{G_1, G_2, \ldots, G_m\}$ which is then rank according the posterior probability of the genotype given the crime stain.

The list of genotypes is generated from the crime scene C. For example if $C=\{h_1, h_2\}$, where both $h_1$ and $h_2$ are greater than the dropout threshold, t, then the only potential donor genotype is $G=\{1,2\}$. If $C=\{h_1\}$, then the potential donors are $G_1=\{1,1\}$ and $G_2=\{1,Q\}$, where Q represent any other allele different than allele 1, present in the DNA, but not observed in the results for the crime profile C.

The posterior probability of a supposed genotype given the crime profile is given by the formula:

$$Pr(G_i | C) = \frac{f(C | G_i) \pi(G_i)}{\sum_i f(C | G_i) \pi(G_i)} \tag{52}$$

where the $G_i$ are assumed to be the various members of an exhaustive list of potential donor genotypes, and $\pi(G_i)$ is a prior distribution for genotype $G_i$ computed from the population in question.

In a similar manner to the evidential context and equation 4 described above, the term:

$f(C|G_i)$ is key to the process, and this term can be estimated successfully using the various approaches for quantifying the pdf discussed above.

In general, the estimation is the same as with evidential assessment discussed elsewhere.

Situation 4—An Intelligence Context—A Single Source Sample—With Conditioning on DNA Quantity It is possible to extend the approach in situation 3 to consider the quantity of DNA involved, in a similar manner to the extension of situation 1 to situation 2.

The posterior probability in this situation is computed using the formula:

$$Pr(G_i | C) = \frac{\left[\sum_j f(C | G_i, \chi_j) Pr(\chi_j | I(h))\right] \times Pr(G_i)}{\sum_i \left[\sum_j f(C | G_i, \chi_j) Pr(\chi_j | I(h))\right] \times Pr(G_i)} \tag{53}$$

where $Pr(\chi_j|I(h))$ is a probability distribution of DNA quantity given information on peak heights. The possibilities for establishing this probability distribution in respect of the same loci and/or across one or more other loci, and possibly including the locus where the formula will applied in practice, exist.

Situation 5)—An Evidential Context—A Mixed Source Sample—Without Conditioning on DNA Quantity In a variety of situations, the DNA sample encountered is not from a single source, but rather from a mixed source. A mixed source arises from two, three or more contributors. The approach is detailed in respect of one such mixed source situation, but the approach is valid for other types of mixed source sample too.

In the evidential context for a mixed source sample arising from two contributors, the prosecution and defence will both have hypotheses. The hypotheses may be, for the example:

i) the prosecution hypothesis, $H_p$: The suspect and someone else are the donors to the stain at the scene of crime;

ii) the defence hypothesis, $H_d$: Two unknown people are the donors to the stain at the scene of crime.

The LR is given by the formula:

$$LR = \frac{Pr(C|S, H_p)}{Pr(C|S, H_d)}. \quad (54)$$

The crime profile can contain from zero to four heights depending upon the alleles contributed by the two sources and the extent to which they are reflected in the analysis results. The LR formula can be written as:

$$LR = \frac{\sum_i f(C|S, U_i, H_p) Pr(U_i | S)}{\sum_j \sum_k f(C|U_j, U_k, S, H_d) Pr(U_j, U_k | S)}. \quad (55)$$

where $f(C|S,U_i,H_p)$ is a density function of C given S and $U_i$ and $f(C|U_j,U_k,S,H_d)$ is a density function of C given $U_j$, $U_k$ and S.

Equation 10 is a ratio of likelihoods and, therefore, the Pr's have changed to f's.

There are a number of ways in which the factors $Pr(U_i|S)$ and $Pr(U_j,U_k|S)$ can be computed using the formula introduced by Balding et al. (1996) also described in Balding (2005) and Buckleton (2005) which may include considerations of relatedness.

The factors $f(C|S,U_i,H_p)$ and $f(C|U_j,U_k,S,H_d)$ state the same type of calculation: the likelihood of the crime profile C given two supposed donors. We denote this calculation by the term:

$$f(C|G_1,G_2) \quad (56)$$

where $G_1$ and $G_2$ are the genotypes of the supposed donors. Hence, the situation is reduced to a factor of an equivalent general nature to that in the previous situations. This can be evaluated using the control sample approach previously described.

In the following sections a more detailed application of the approach to evidential contexts is provided for the two scenarios:

a) Suspect and victim are heterozygous, with no overlapping alleles between them and only three peaks in the crime profile; and b) Suspect and victim are heterozygous, with one overlapping allele between them and only three peaks in the crime profile.

In both scenarios, where we are considering LR's for a locus, in respect of a sample from two sources, there are two basic hypotheses to consider:

$H_p$: The suspect (S) and the victim (V) are the originators of the crime profile, the hypothesis of the prosecution; and $H_d$: The victim (V) and an unknown (U) are the originators of the crime profile, the hypothesis of the defence.

Heterozygous Suspect and Victim With no Overlapping Alleles and Three Peaks in the Crime Profile In this situation, $H_p$: V+S, $H_d$: V+U, $C=\{h_a,h_b,h_c\}$, $V=\{a,b\}$ and $S=\{c,d\}$. The LR is given by:

$$LR = \frac{f(C = \{h_a, h_b, h_c\} | V = \{a, b\}, S = \{c, d\}, H_p)}{f(C = \{h_a, h_b, h_c\} | V = \{a, b\}, S = \{c, d\}, H_d)}. \quad (4.1)$$

The numerator is given by:

$$f(C=\{h_a,h_b,h_c\}|V=\{a,b\},S=\{c,d\},H_p)=f_{het}(h_a,h_b)\times f_{het}(h_c,h_d) \quad (4.2)$$

The independence assumption in equation 2.2 is also made for a simulation method.

The unknown contributors for the denominators can be $\{a,c\}$, $\{b,c\}$, $\{c,Q\}$. The denominator is given by:

$$f(C = \{h_a, h_b, h_c\} | V = \{a, b\}, S = \{c, d\}, H_d) = \quad (4.3)$$
$$f(C = \{h_a, h_b, h_c\} | V = \{a, b\}, S = \{c, d\}, U = \{a, c\}, H_d)$$
$$Pr(U = \{a, c\} | S = \{a, b\}) +$$
$$f(C = \{h_a, h_b, h_c\} | V = \{a, b\}, S = \{c, d\}, U = \{b, c\}, H_d)$$
$$Pr(U = \{b, c\} | S = \{a, b\}) +$$
$$f(C = \{h_a, h_b, h_c\} | V = \{a, b\}, S = \{c, d\}, U = \{c, Q\}, H_d)$$
$$Pr(U = \{a, c\} | S = \{a, b\}).$$

The factor for $U=\{a,c\}$ is computed with the formula:

$$f(C=\{h_a,h_b,h_c\}|V=\{a,b\},U=\{a,c\},H_d)=f_{het}(m_x h_a,h_b)\times f_{het}((1-m_x)h_a,h_c). \quad (4.4)$$

The factor for $U=\{b,c\}$ is computed with the formula:

$$f(C=\{h_a,h_b,h_c\}|V=\{a,b\},U=\{b,c\},H_d)=f_{het}(h_a,m_x h_b)\times f_{het}(h_a,(1-m_x)h_c). \quad (4.5)$$

The factor for $U=\{c,Q\}$ is computed with the formula:

$$f(C=\{h_a,h_b,h_c\}|V=\{a,b\},U=\{c,Q\},H_d)=f_{het}(h_a,h_b)\times f_{het}(h_c,h_Q). \quad (4.6)$$

Heterozygous Suspect and Victim With One Overlapping Allele and Three Peaks in the Crime Profile In this situation, $H_p$: V+S, $H_d$: V+U, $C=\{h_a,h_b,h_c\}$, $V=\{a,b\}$ and $S=\{b,c\}$. The likelihood ratio is given by:

$$LR = \frac{f(C = \{h_a, h_b, h_c\} | V = \{a, b\}, S = \{b, c\}, H_p)}{f(C = \{h_a, h_b, h_c\} | V = \{a, b\}, S = \{b, c\}, H_d)}. \quad (5.1)$$

For the numerator we have:

$$f(C=\{h_a,h_b,h_c\}|V=\{a,b\},S=\{b,c\},H_p)=f_{het}(h_a,m_x h_b) f_{het}((1-m_x)h_b,h_c). \quad (5.2)$$

For the denominator we consider the following potential unknown contributors:

$$U \in \{\{a,c\},\{b,c\},\{c,c\},\{c,Q\}\}.$$

We look at the formulae per unknown contributor. We start with $U=\{a,c\}$:

$$f(C=\{h_a,h_b,h_c\}|V=\{a,b\},S=\{b,c\},U=\{a,c\},H_d)=f_{het}(m_x h_a,h_b) f_{het}((1-m_x)h_a,h_c) \quad (5.3)$$

For $U=\{b,c\}$:

$$f(C=\{h_a,h_b,h_c\}|V=\{a,b\},U=\{b,c\},H_d)=f_{het}(h_a,m_x h_b) f_{het}((1-m_x)h_b,h_c). \quad (5.4)$$

For $U=\{c,c\}$:

$$f(C=\{h_a,h_b,h_c\}|V=\{a,b\},U=\{c,c\},H_d)=f_{het}(h_a,h_b) f_{het}(0.5h_c,0.5h_c) \quad (5.5)$$

For $U=\{c,Q\}$:

$$f(C=\{h_a,h_b,h_c\}|V=\{a,b\},U=\{c,Q\},H_d)=f_{het}(h_a,h_b) f_{het}(h_c,h_Q). \quad (5.6)$$

At the core for evidential situations, and in the intelligence situations discussed below, is the calculation of the likelihood $f(C|G_1,G_2)$.

Situation 6—An Evidential Context—A Mixed Source Sample—With Conditioning on DNA Quantity This situation is dealt with in an equivalent manner to that described above for situation 5. The formulae can be modified to use the conditioning of DNA quantity.

Situation 7—An Intelligence Context—A Mixed Source Sample—Without Conditioning on DNA Quantity In the intelligence context, the task is to propose an ordered list of pairs of genotypes $G_1$ and $G_2$ per locus so that the first pair in the list in the most likely donor of the crime stain.

The starting point is the crime stain profile C. For example $C=\{h_1,h_2,h_3\}$. From this, an exhaustive list $\{G_{1,i},G_{2,i}\}$ of pairs of potential donors is generated. For each of theses pairs, a probability distribution for the genotypes is calculated using the formula:

$$Pr(G_{1,i}, G_{2,i} | C) = \frac{f(C | G_{1,i}, G_{2,i})Pr(G_{1,i}, G_{2,i})}{\sum_i f(C | G_{1,i}, G_{2,i})Pr(G_{1,i}, G_{2,i})} \quad (57)$$

where $Pr(G_{1,i},G_{2,i})$ is a prior distribution for the pair of genotypes inside the brackets that can be set to a uniform distribution or computed using the formulae introduced by Balding et al. (1996).

As with the situations 5 and 6 in the previous sections, at the core for evidential evaluation and intelligence is the calculation of the likelihood $f(C|G_1,G_2)$.

Situation 8—An Intelligence Context—A Mixed Source Sample—With Conditioning on DNA Quantity Situation 8 can be handled using the approach of situation 7, but with the term $f_{het}$ is conditioned on DNA quantity.

Additional Information for Mixed Source Situations

As previously mentioned, at the core of the mixed source approach for evidential intelligence contexts is the calculation of the likelihood $f(C|G_1,G_2)$. The description which follows provides for the calculation of $f(C|G_1,G_2)$ via a factorisation that reduces it to a calculation of likelihood for single profiles. That approach is also extended to $f(C|G_1,G_2,\chi_i)$ to allow conditioning on DNA quantity. Furthermore, the estimation of $Pr(\chi_i|I(h))$ from experimental data and its use in conjunction with these formula is detailed.

The way in which these terms are computed depends on the alleles that the genotypes share. They are described case-by-case, starting with a method where the factorisation of likelihoods is based on conditioning on a mixing proportion. A method in which conditioning on DNA quantity, $\chi$, as well as conditioning on mixing proportion $m_x$ is then provided.

Calculation of Likelihoods Via Conditioning on $m_x$

Scenario 1—Where the Donors do not Share Any Alleles

In this case we do not need the assistance of a mixing proportion $m_x$ to factorise the likelihood of a two-person mixture to two likelihoods of single profiles. For example if the two donors are heterozygous then:

$$f(C=\{h_1,h_2,h_3,h_4\}|G_1=\{1,2\},G_2=\{3,4\})=f(C=\{h_1,h_2\}|G_1=\{1,2\})f(C=\{h_3,h_4\}|G_2=\{3,4\}) \quad (58)$$

If the one donor is homozygous:

$$f(C=\{h_1,h_2,h_3\}|G_1=\{1,2\},G_2=\{3,3\})=f(C=\{h_1,h_2\}|G_1=\{1,2\})f(C=\{h_3\}|G_2=\{3,3\}). \quad (59)$$

If both donors are homozygotes:

$$f(C=\{h_1,h_2\}|G_1=\{1,1\},G_2=\{2,2\})=f(C=\{h_1\}|G_1=\{1,1\})f(C=\{h_2\}|G_2=\{2,2\}). \quad (60)$$

Scenario 2—Where the Donors Share One Allele

If the donors share one-allele, then the peak height in common, the largest peak, is split according to a mixing proportion $m_x$. If both donors are heterozygous:

$$f(C = \{h_1, h_2, h_3\} | G_1 = \{1, 2\}, G_2 = \{2, 3\}) = \quad (61)$$

$$\sum_{m_x} f(C = \{h_1, h_2, h_3\} | G_1 = \{1, 2\}, G_2 = \{2, 3\}, m_x)Pr(m_x) =$$

$$\sum_{m_x} f(C = \{h_1, m_x h_2\} | G_1 = \{1, 2\}, m_x)$$

$$f(C = \{(1 - m_x)h_2, h_3\} | G_2 = \{2, 3\}, m_x)Pr(m_x)$$

where $Pr(m_x)$ is a discrete probability distribution for the mixing proportion.

If one of the donors is homozygous:

$$f(C = \{h_1, h_2\} | G_1 = \{1, 2\}, G_2 = \{2, 2\}) = \quad (62)$$

$$\sum_{m_x} f(C = \{h_1, h_2\} | G_1 = \{1, 2\}, G_2 = \{2, 3\}, m_x)Pr(m_x) =$$

$$\sum_{m_x} f(C = \{h_1, m_x h_2\} | G_1 = \{1, 2\}, m_x)$$

$$f(C = \{(1 - m_x)h_2\} | G_2 = \{2, 2\}, m_x)Pr(m_x)$$

Scenario 3—Where the Donors Share Two-Alleles

As with scenario 2, the mixing proportion is used for factorising a two-person-mixture likelihood into two single-profile likelihoods. Both peaks are split. More specifically:

$$f(C = \{h_1, h_2\} | G_1 = \{1, 2\}, G_2 = \{1, 2\}) = \quad (63)$$

$$\sum_{m_x} f(C = \{h_1, h_2\} | G_1 = \{1, 2\}, G_2 = \{1, 2\}, m_x)Pr(m_x) =$$

$$\sum_{m_x} \begin{bmatrix} f(C = \{m_x h_1, m_x h_2\} | G_1 = \{1, 2\}, m_x) \times \\ f(C = \{(1 - m_x)h_1, (1 - m_x)h_2\} | G_2 = \{1, 2\}, m_x)Pr(m_x) \end{bmatrix}.$$

Calculation of Likelihoods Via Conditioning on DNA Quantity $\chi$ and mx

Scenario 1—Where the Donors do not Share Any Alleles

If the two donors are heterozygotes then:

$$f(C = \{h_1, h_2, h_3, h_4\} | G_1 = \{1, 2\}, G_2 = \{3, 4\}) = \quad (64)$$

$$\sum_{m_x} \sum_{\chi_i} \begin{bmatrix} f(C = \{h_1, h_2\} | G_1 = \{1, 2\}, m_x \chi_i) \times \\ f(C = \{h_3, h_4\} | G_2 = \{3, 4\}, (1 - m_x)\chi_i) \times \\ Pr(m_x)Pr(\chi_i | I(h)) \end{bmatrix}$$

where $m_x\chi_i$ is the proportion of the DNA quantity assign to donor 1 and $(1-m_x)\chi_i$ is the DNA quantity assign to donor 2. $Pr(\chi_i|I(h))$ is a probability distribution on DNA quantity based on peak height information.

If one donor is homozygous:

$$f(C = \{h_1, h_2, h_3\} \mid G_1 = \{1, 2\}, G_2 = \{3, 3\}) = \quad (65)$$

$$\sum_{m_x} \sum_{\chi_i} \begin{bmatrix} f(C = \{h_1, h_2\} \mid G_1 = \{1, 2\}, m_x \chi_i) \times \\ f(C = \{h_3\} \mid G_2 = \{3, 3\}, (1-m_x)\chi_i) \times \\ Pr(m_x) Pr(\chi_i \mid I(h)) \end{bmatrix}.$$

If both donors are homozygotes:

$$f(C = \{h_1, h_2\} \mid G_1 = \{1, 1\}, G_2 = \{2, 2\}) = \quad (66)$$

$$\sum_{m_x} \sum_{\chi_i} \begin{bmatrix} f(C = \{h_1\} \mid G_1 = \{1, 1\}, m_x \chi_i) \times \\ f(C = \{h_2\} \mid G_2 = \{2, 2\}, (1-m_x)\chi_i) \times \\ Pr(m_x) Pr(\chi_i \mid I(h)) \end{bmatrix}$$

Scenario 2—Where the Donors Share One Allele

If the donors share one-allele, then the peak height in common is split according to a mixing proportion $m_x$. If both donors are heterozygous:

$$f(C = \{h_1, h_2, h_3\} \mid G_1 = \{1, 2\}, G_2 = \{2, 3\}) = \quad (67)$$

$$\sum_{m_x} \sum_{\chi_i} f(C = \{h_1, h_2, h_3\} \mid G_1 = \{1, 2\}, G_2 = \{2, 3\}, \chi_i, m_x)$$

$$Pr(m_x) Pr(\chi_i \mid I(h)) =$$

$$\sum_{m_x} \sum_{\chi_i} \begin{bmatrix} f(C = \{h_1, m_x h_2\} \mid G_1 = \{1, 2\}, m_x \chi_i) \times \\ f(C = \{(1-m_x)h_2, h_3\} \mid G_2 = \{2, 3\}, (1-m_x)\chi_i) \times \\ Pr(m_x) Pr(\chi_i \mid I(h)) \end{bmatrix}$$

where $Pr(m_x)$ is a discrete probability distribution for the mixing proportion and $Pr(\chi_i \mid I(h))$ is a probability distribution of DNA quantity given peak information from the one more loci, possibly including the locus for which the formula will be used.

If one of the donors is homozygous:

$$f(C = \{h_1, h_2\} \mid G_1 = \{1, 2\}, G_2 = \{2, 2\}) = \quad (68)$$

$$\sum_{m_x} \sum_{\chi_i} f(C = \{h_1, h_2\} \mid G_1 = \{1, 2\}, G_2 = \{2, 2\}, m_x) Pr(m_x) Pr(\chi_i) =$$

$$\sum_{m_x} \sum_{\chi_i} \begin{bmatrix} f(C = \{h_1, m_x h_2\} \mid G_1 = \{1, 2\}, m_x \chi_i) \times \\ f(C = \{(1-m_x)h_2\} \mid G_2 = \{2, 2\}, (1-m_x)\chi_i) \times \\ Pr(m_x) Pr(\chi_i) \end{bmatrix}$$

Scenario 3—Where the Donors Share Two-alleles

As with previous cases, the mixing proportion is used for factorising a two-person-mixture likelihood into two single-profile likelihoods. More specifically:

$$f(C = \{h_1, h_2\} \mid G_1 = \{1, 2\}, G_2 = \{1, 2\}) = \quad (69)$$

$$\sum_{m_x} \sum_{\chi_i} f(C = \{h_1, h_2\} \mid G_1 = \{1, 2\}, G_2 = \{1, 2\}, m_x)$$

$$Pr(m_x) Pr(\chi_i \mid I(h)) =$$

$$\sum_{m_x} \sum_{\chi_i} \begin{bmatrix} f(C = \{m_x h_1, m_x h_2\} \mid G_1 = \{1, 2\}, m_x \chi_i) \times \\ f(C = \{(1-m_x)h_1, (1-m_x)h_2\} \mid G_2 = \\ \{1, 2\}, (1-m_x)\chi_i) \times Pr(m_x) Pr(\chi_i \mid I(h)) \end{bmatrix}.$$

General Observations

By making use of 2D pdf's, the present invention provides a number of advantages and allows a variety of situations and hypotheses to be considered.

Figure 16:
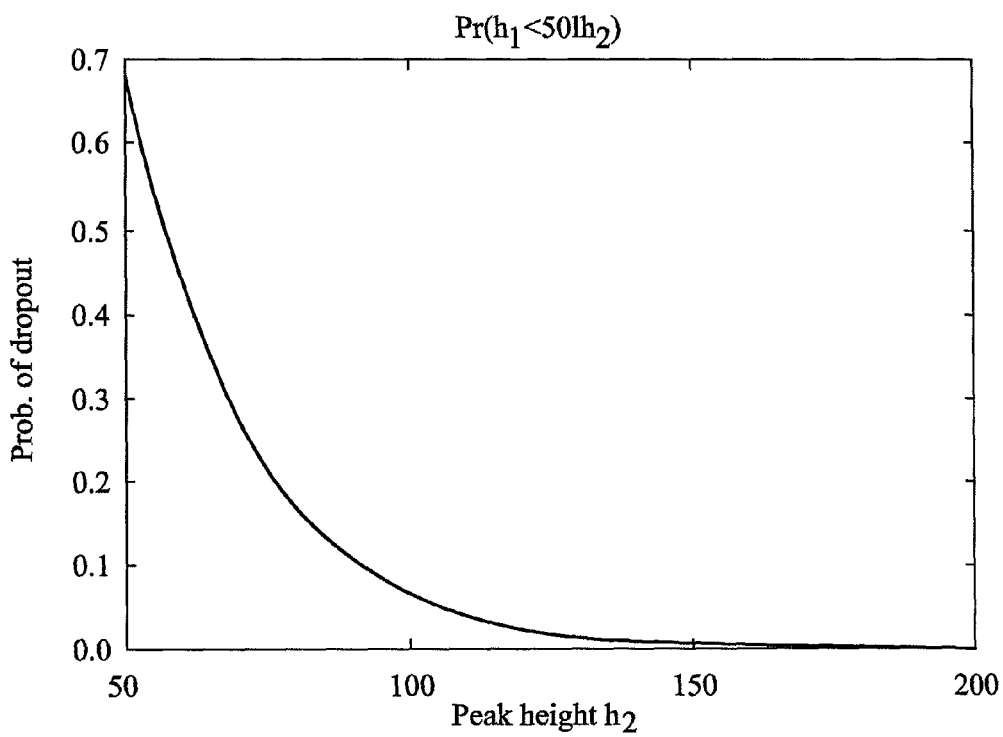
FIG. 16 is an illustration of the probability of dropout as a function of peak height of the remaining allele.

For instance, the situation of FIG. 16 could arise due to the sample source being homozygous or due to the sample source being heterozygous and allele dropout occurring. Both of these possibilities are fully considered in the present invention.

In the context of the mixtures consideration, the principle of comparing pdf's having the same number of dimensions is also used. In this case, there are a number of 3D pdf's (such as those in equations 4.4, 4.5, 5.3, 5.4) to compare with 2D pdf's (such as those in equations 4.6, 5.5, 5.6). The 3D pdf's are moved to be 2D pdf's by deconvoluting for each allele, taking into account the mixing proportions.

Modelling according to the present invention offers a number of advantages:

1) the model can deal with allelic dropout as dropout events are considered in the estimation of the 2D pdf.
2) the model can deal with preferential amplification automatically and as a function of mean peak height. At present, reporting officers involved in the analysis process need to select which combinations of donors to choose according to preferential amplification thresholds.
3) the model can deal with degradation. The preferential amplification distribution implicit in the 2D pdf changes according to mean peak height.
4) the model will render a system that will give larger likelihood ratios for a larger number of cases and can help ranking profiles obtained from a database search.
5) the above mentioned approach could be extended to provide for scoring the results of the mixture analysis.
6) the approach allows for searches against a database to be prioritised and so give a reduced number of searches which are needed. A reduced number of searches gives an increase in search speed.

The following documents, and their contents, are incorporated herein by reference, with particular emphasis on their teachings as reference at specific locations within this documents:

D. J. Balding, M. Greenhalgh, R. A. Nichols (1996). Population genetics of STR loci in Caucasians. 108:300-305.

D. J. Balding (2005). Weight-of-evidence for forensic DNA profiles. John Wiley & Sons Ltd.

J. Buckleton, C. M. Triggs, S. J. Walsh (2005). Forensic DNA evidence interpretation. CRC press.

A. Dempster, N. Laird, and D. Rubin (1977). "Maximum likelihood from incomplete data via the EM algorithm". Journal of the Royal Statistical Society, Series B, 39(1):1-38.

The invention claimed is:

1. A computer implemented method of comparing a test sample result set with another sample result set, the method including:
   obtaining a test sample and analysing the test sample to provide a test sample result;
   providing information for the test sample result set on the one or more identities detected for a variable characteristic of DNA;

providing information for the another sample result set on the one or more identities detected for a variable characteristic of DNA, the another sample result having been obtained from another test sample by analysis;

establishing a likelihood ratio for one hypothesis relative to an alternative hypothesis, wherein the likelihood ratio is defined as:

$$LR = \frac{Pr(C \mid S, H_p)}{\sum_i Pr(C \mid U_i, S, H_d)Pr(U_i \mid S, H_d)}$$

where: C is the test result set from a test sample, S is the another sample result set, $H_p$ is one hypothesis, $H_d$ is an alternative hypothesis, $U_i$ is one of the supposed sources stated in $H_d$;

wherein the likelihood ratio is conditioned on quantity of DNA in the test sample and/or another sample result set;

wherein the likelihood ratio is displayed to the user by the computer; and wherein the method provides evidence as to the likelihood ratio of one hypothesis to another hypothesis, the one hypothesis being that advanced by the prosecution in the legal proceedings and the another hypothesis being that advanced by the defence in the legal proceedings.

2. The computer implemented method according to claim 1 in which the likelihood ratio includes a definition of the likelihood of observing the set of peak heights in C given a supposed source.

3. The computer implemented method according to claim 2 in which the likelihood ratio is defined as:

$$LR = \frac{f(C \mid S, H_p)}{\sum_i f(C \mid U_i, S, H_d)Pr(U_i \mid S, H_d)}$$

where the f terms are factors that are likelihoods.

4. The computer implemented method according to claim 3 in which the factors $f(C|S,H_p)$ and/or $f(C|U_i,S,H_d)$ are definitions of the likelihood of observing the set of peak heights in C given a supposed source.

5. The computer implemented method according to claim 1 in which the comparison includes the consideration of the term: f(C|G), where G denotes the supposed source genotype.

6. The computer implemented method according to claim 5 in which the likelihood is computed by conditioning on DNA quantity, in the form:

$$f(C \mid G) = \sum_j f(C \mid G, \chi_j)Pr(\chi_j \mid I(h)) \quad (1)$$

where $Pr(\chi_j|I(h))$ is a probability distribution of DNA quantity, $\chi_j$, given peak height information, I(h).

7. The computer implemented method according to claim 5 in which the term f(C|G) is an estimation.

8. The computer implemented method according to claim 5 in which the term f(C|G) is derived from experimental data.

9. The computer implemented method according to claim 8 in which the term f(C|G) includes one or more probability distribution functions.

10. The computer implemented method according to claim 9 in which the probability distribution for $Pr(\chi_j|I(h))$ relates to a list of discrete probabilities for DNA quantities $\chi_1$ to $\chi_j$, where $$\sum_j Pr(\chi_j \mid I(h)) = 1.$$

11. The computer implemented method according to claim 10 in which the probability distribution is obtained by considering an observed distribution from the analysis of control samples of DNA.

12. The computer implemented method according to claim 9 in which the probability distribution function is provided by estimating a two dimensional pdf for a pair of heights $h_1$ and $h_2$, in the space defined by mean heights, m, and heterozygote imbalance, r.

13. The computer implemented method according to claim 12, wherein each pair of heights is transformed by $$(h_1, h_2) \mapsto \left(m = \frac{h_1 + h_2}{2}, r = \frac{h_1}{h_2}\right).$$

14. The computer implemented method according to claim 13, wherein given a pdf $f_{M,R}$, a pdf in the space of pairs of heights is obtained with the formula:

$$f_{H_1,H_2}(h_1, h_2) = \frac{1}{h_2^2}\left(\frac{h_1 + h_2}{2}\right) \times f_{M,R}(m, r).$$

15. The computer implemented method according to claim 14 in which the factor $$\frac{1}{h_2^2}\left(\frac{h_1 + h_2}{2}\right)$$

is the Jacobian of the transformation.

16. The computer implemented method according to claim 14 in which the factor $f_{M,R}(m,r)$ is estimated from experimental data.

17. A computer implemented method of comparing a test sample result set with another sample result set, the method including:

providing information for the test sample result set on the one or more identities detected for a variable characteristic of DNA;

providing information for the another sample result set on the one or more identities detected for a variable characteristic of DNA;

establishing a likelihood ratio for one hypothesis relative to an alternative hypothesis, wherein the likelihood ratio is defined as:

$$LR = \frac{Pr(C \mid S, H_p)}{\sum_i Pr(C \mid U_i, S, H_d)Pr(U_i \mid S, H_d)}$$

where: C is the test result set from a test sample, S is the another sample result set, $H_p$ is one hypothesis, $H_d$ is an alternative hypothesis, $U_i$ is one of the supposed sources stated in $H_d$; and wherein the likelihood ratio is conditioned on quantity of DNA in the test sample and/or another sample result set.

18. The computer implemented method according to claim 17 in which the likelihood ratio includes a definition of the likelihood of observing the set of peak heights in C given a supposed source.

19. The computer implemented method according to claim 17 in which the likelihood ratio is defined as:

$$LR = \frac{f(C \mid S, H_p)}{\sum_i f(C \mid U_i, S, H_d) Pr(U_i \mid S, H_d)}$$

where the f terms are factors that are likelihoods.

20. The computer implemented method according to claim 19 in which the factors $f(C|S,H_p)$ and/or $f(C|U_i,S,H_d)$ are definitions of the likelihood of observing the set of peak heights in C given a supposed source.

21. The computer implemented method according to claim 17 in which the comparison includes the consideration of the term: $f(C|G)$, where G denotes the supposed source genotype.

22. The computer implemented method according to claim 21 in which the likelihood is computed by conditioning on DNA quantity, in the form:

$$f(C \mid G) = \sum_j f(C \mid G, \chi_j) Pr(\chi_j \mid I(h)) \qquad (2)$$

where $Pr(\chi_j|I(h))$ is a probability distribution of DNA quantity, $\chi_j$, given peak height information, $I(h)$.

23. The computer implemented method according to claim 21 in which the term $f(C|G)$ is an estimation.

24. The computer implemented method according to claim 21 in which the term $f(C|G)$ is derived from experimental data.

25. The computer implemented method according to claim 24 in which the term $f(C|G)$ includes one or more probability distribution functions.

26. The computer implemented method according to claim 25 in which the probability distribution for $Pr(\chi_j|I(h))$ relates to a list of discrete probabilities for DNA quantities $\chi_1$ to $\chi_j$, where $$\sum_j Pr(\chi_j \mid I(h)) = 1.$$

27. A method according to claim 25 in which the probability distribution is obtained by considering an observed distribution from the analysis of control samples of DNA.

28. The computer implemented method according to claim 25 in which the probability distribution function is provided by estimating a two dimensional pdf for a pair of heights $h_1$ and $h_2$, in the space defined by mean heights, m, and heterozygote imbalance, r.

29. The computer implemented method according to claim 28, wherein each pair of heights is transformed by $$(h_1, h_2) \mapsto \left( m = \frac{h_1 + h_2}{2}, r = \frac{h_1}{h_2} \right).$$

30. The computer implemented method according to claim 29, wherein given a pdf $f_{M,R}$, a pdf in the space of pairs of heights is obtained with the formula:

$$f_{H_1,H_2}(h_1, h_2) = \frac{1}{h_2^2}\left(\frac{h_1 + h_2}{2}\right) \times f_{M,R}(m, r).$$

31. The computer implemented method according to claim 30 in which the factor $$\frac{1}{h_2^2}\left(\frac{h_1 + h_2}{2}\right)$$

is the Jacobian of the transformation.

32. The computer implemented method according to claim 30 in which the factor $f_{M,R}(m,r)$ is estimated from experimental data.

* * * * *